(12) United States Patent
Lee et al.

(10) Patent No.: US 8,309,584 B2
(45) Date of Patent: Nov. 13, 2012

(54) SULFUR CONTAINING PYRAZOLE-HETEROCYCLE DERIVATIVES AS CANNABINOID CB1 RECEPTOR ANTAGONISTS

(75) Inventors: Jinhwa Lee, Yongin-si (KR); Hee Jeong Seo, Yongin-si (KR); Min-Ah Kim, Yongin-si (KR); Jeongmin Kim, Yongin-si (KR); Sung-Han Lee, Yongin-si (KR); Myung Eun Jung, Yongin-si (KR); Mi-Soon Kim, Guri-si (KR)

(73) Assignee: Green Cross Corporation, Yongin-si (KR)

( * ) Notice: Subject to any disclaimer, the term of this patent is extended or adjusted under 35 U.S.C. 154(b) by 72 days.

(21) Appl. No.: 13/120,026

(22) PCT Filed: Sep. 25, 2008

(86) PCT No.: PCT/KR2008/005689
§ 371 (c)(1),
(2), (4) Date: Mar. 21, 2011

(87) PCT Pub. No.: WO2010/035915
PCT Pub. Date: Apr. 1, 2010

(65) Prior Publication Data
US 2011/0178140 A1    Jul. 21, 2011

(51) Int. Cl.
*A61K 31/433*    (2006.01)
*A61K 31/4245*   (2006.01)
*A61P 3/04*      (2006.01)
*C07D 413/04*    (2006.01)
*C07D 417/04*    (2006.01)

(52) U.S. Cl. ......... 514/361; 514/364; 548/128; 548/131
(58) Field of Classification Search ......... 514/361, 514/364; 548/128, 131
See application file for complete search history.

(56) References Cited

U.S. PATENT DOCUMENTS

2008/0039510 A1*  2/2008  Barth et al. ............ 514/364
2008/0081815 A1   4/2008  Lee et al.

FOREIGN PATENT DOCUMENTS

WO     2006/114400 A1   11/2006

OTHER PUBLICATIONS

International Search Report for International Application No. PCT/KR2008/005689 dated Jun. 23, 2009.
Written Opinion for International Application No. PCT/KR2008/005689 dated Jun. 23, 2009.
Kang SY, et al., "Tetrazole-biarylpyrazole derivatives as cannabinoid CB1 receptor antagonists", Bioorg Med Chem Lett, 2008, pp. 2385-2389, vol. 18, No. 7.
Cheng-Ming Chu, et al., "Bioisosteric replacement of the pyrazole 3-carboxamide moiety of rimonabant. A novel series of oxadiazoles as CB1 cannabinoid receptor antagonists", Org. Biomol. Chem., 2008, pp. 3399-3407, vol. 6.

* cited by examiner

*Primary Examiner* — Yong Chu
(74) *Attorney, Agent, or Firm* — Sughrue Mion, PLLC

(57) ABSTRACT

A novel sulfur containing heteroaryl-pyrazole compound of formula (I) or a pharmaceutically acceptable salt thereof is effective as a cannabinoid $CB_1$ receptor inverse agonist or antagonist, which is useful for preventing or treating obesity and obesity-related metabolic disorders. The prevention also provide a method for preparing same, a pharmaceutical composition containing same, and a method for preventing or treating obesity and obesity-related metabolic disorders.

7 Claims, No Drawings

SULFUR CONTAINING PYRAZOLE-HETEROCYCLE DERIVATIVES AS CANNABINOID CB1 RECEPTOR ANTAGONISTS

FIELD OF THE INVENTION

The present invention relates to a novel sulfur containing pyrazole-heterocycle derivative which is effective as a cannabinoid $CB_1$ receptor inverse agonist or receptor antagonist.

BACKGROUND OF THE INVENTION

The World Health Organization (WHO) recently reported that obesity has become a global epidemic, posing a serious threat to public health because of the increased risk of associated health problems (See *Report of a WHO Consultation on Obesity: Obesity-Preventing and Managing a Global Epidemic*; World Health Organization: Geneva, 1997). Obesity is characterized by excess body fat, especially visceral fat, and constitutes a pro-inflammatory state eventually leading to serious health consequences. There are growing evidences that obesity as a chronic disease cannot be cured by short-term dieting or exercise alone, but additional pharmacological treatments would lead to higher success rates.

$CB_1$ cannabinoid receptor belongs to G-protein-coupled receptor (GPCR) type and is coupled to inhibitory G proteins (G(i/o)) to inhibit certain adenylyl cyclase isozymes, leading to decreased cAMP production, decreased $Ca^{2+}$ conductance, increased $K^+$ conductance, and increased mitogen-activated protein kinase activity (See Di Marzo et al., *Nat. Rev. Drug Discovery* 2004, 3, 771-784; Rhee, M. H. et al., *J. Neurochem.* 1998, 71, 1525-1534). The major physiological effect of cannabinoids (in the central nervous system (CNS) and neuronal tissues) is the modulation of neurotransmitter release via activation of presynaptic $CB_1$ receptors located on distinct types of axon terminals throughout the brain (See Howlett, A. C. et al., *Neuropharmacology* 2004, 47 (Suppl. 1), 345-358).

The $CB_1$ receptor is mainly expressed in several brain areas including the limbic system (amygdala, hippocampus), hypothalamus, cerebral cortex, cerebellum, and basal ganglia. In the cerebellum and basal ganglia cannabinoids modulate the locomotor activity. In the limbic system, cannabinoids influence learning, memory, emotion, and motivation, and through activation of $CB_1$ receptors in the limbic system-hypothalamus axis, cannabinoids have an important role in the control of appetite. Moreover, lower levels of $CB_1$ receptors can also be found in peripheral tissues including urinary bladder, testis, prostate, GI tract, heart, lung, adrenal gland, parotid gland, bone marrow, uterus, ovary, and adipose tissue (See Cota, D. et al., *J. Clin. Invest.* 2003, 112, 423-431; Ravinet Trillou, C. et al., *Int. J. Obes. Relat. Metab. Disord.* 2004, 28, 640-648; Galiegue, S. et al., *Eur. J. Biochem.* 1995, 232, 54-61; Howlett, A. C. et al., *Pharmacol. Rev.* 2002, 54, 161-202).

Many preclinical in vitro and in vivo experiments have been shown that $CB_1$ receptor antagonists can influence energy homeostasis by central and peripheral mechanisms and may represent promising targets to treat diseases that are characterized by impaired energy balance. Already the first published studies with rimonabant (SR141716) in both rodents (See Arnone, M. et al., *Psychopharmacology (Berlin)* 1997, 132, 104-106) and primates (See Simiand, J.; Keane, M.; Keane, P. E.; Soubrie, P. *Behav. Pharmacol.* 1998, 9, 179-181) showed clear differentiation, i.e., marked effects on sweet food intake versus marginal effects on regular chow intake or water drinking. Many other preclinical "proof of concept" studies have been performed in the meantime with several CB agonists and antagonists to further uncover the amount and mode of contribution of cannabinergic system modulators to energy homeostasis. Almost all of those studies have been recently reviewed (See Smith, R. A. et al., *IDrugs* 2005, 8, 53-66).

Considering the important impact of obesity on public health and the lack of any efficient and viable drug to cure it, it is no surprise that $CB_1$ antagonists are currently the subject of intense studies, which were published in several reviews (See Adam, J. et al., *Expert Opin. Ther. Patents*, 2002, 12(10), 1475-1489; Hertzog, D. L. *Expert Opin. Ther. Patents*, 2004, 14(10), 1435-1452; Lange, J. H. M. et al., *Drug Discov. Today*, 2005, 10, 693-702; Bishop, M. J. *J Med. Chem.*, 2006, 49(14), 4008-4016).

SUMMARY OF THE INVENTION

It is a primary object of the present invention to provide a novel sulfur containing pyrazole-heterocycle compound of formula (I) or a pharmaceutically acceptable salt thereof, which is effective as a cannabinoid $CB_1$ receptor inverse agonist or antagonist, useful for preventing or treating obesity and obesity-related metabolic disorders.

It is another object of the present invention to provide a method for preparing the inventive compound.

It is another object of the present invention to provide a pharmaceutical composition for preventing or treating obesity and obesity-related metabolic disorders, comprising the inventive compound as an active ingredient.

DETAILED DESCRIPTION OF THE INVENTION

In accordance with one aspect of the present invention, there is provided a compound of formula (I) or a pharmaceutically acceptable salt thereof and a method for preparing same:

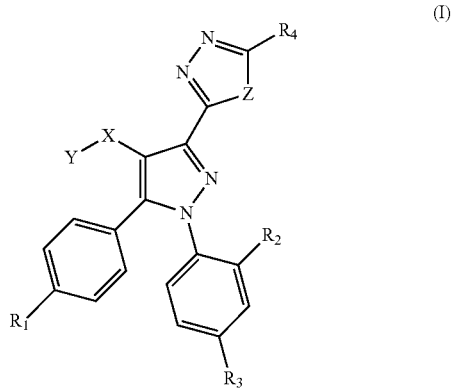

wherein:
R$_1$ is halogen, C$_{1-3}$ alkyl, C$_{1-3}$ alkoxy or trifluoromethyl;
R$_2$ is halogen, C$_{1-3}$ alkyl, C$_{1-3}$ alkoxy or trifluoromethyl;
R$_3$ is hydrogen or halogen;
R$_4$ is hydrogen, NR$_5$R$_6$, carbocycle, substituted carbocycle, aryl, substituted aryl, heteroaryl, substituted heteroaryl, heterocycle, substituted heterocycle, C$_{1-8}$ alkyl optionally substituted by alkoxy or halogen, C$_{2-6}$ alkenyl optionally substituted by alkoxy or halogen, (CH$_2$)$_m$—C$_{3-6}$ carbocycle optionally substituted by alkoxy or halogen, or (CH$_2$)$_m$—R$_7$, m being 1 or 2;

$R_5$ and $R_6$ are each independently hydrogen, $C_{1-6}$ alkyl, substituted $C_{1-6}$ alkyl, $C_{2-6}$ alkenyl, substituted $C_{2-6}$ alkenyl, $C_{3-7}$ cycloalkyl, substituted $C_{3-7}$ cycloalkyl, aryl, substituted aryl, heteroaryl, substituted heteroaryl, heterocycloalkyl, substituted heterocycloalkyl; or $R_5$ and $R_6$, together with the nitrogen atom to which they are bonded, form a 4- to 10-membered saturated or unsaturated heterocyclic ring which is optionally substituted by one or more $C_{1-3}$ alkyl, benzyl, phenyl, $C_{1-3}$ alkoxy or halogen;

$R_7$ is phenyl, furanyl, benzofuranyl, thienyl, benzothienyl, pyridinyl, pyrimidinyl, pyrazinyl, pyridizinyl, tetrahydrofuranyl, tetrahydropyranyl, dioxanyl, 1,4-benzodioxanyl or benzo[1,3]dioxolyl, each being optionally substituted by one or more groups consisting of halogen, $C_{1-3}$ alkyl and $C_{1-2}$ alkoxy, each optionally having one to three fluorine substitutes;

X is a sulfur atom, a sulfoxide (S=O) or a sulfone (SO$_2$) moiety;

Y is methyl or ethyl; and

Z is O or S.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five-to seven-membered rings may contain a double bond in the ring structure. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, SO$_2$, O, N, or N-oxide, or refers to such an aromatic ring fused to one or more rings such as heteroaryl rings, aryl rings, heterocyclic rings, or carbocycle rings (e. g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, SO$_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —OR$_a$, where R$_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein the term "aralkoxy" refers to the group —OR$_a$R$_b$, wherein R$_a$ is alkyl and R$_b$ is aryl as defined above.

As used herein the term "aryloxy" refers to the group —OR$_b$, wherein R$_b$ is aryl as defined above.

As used herein, the term "mercapto" refers to the group —SH.

As used herein, the term "sulfanyl" refers to the group —SR$_c$, wherein R$_c$ is substituted alkyl, substituted carbocycle, aryl, heteroaryl or heterocyclic, as defined above.

As used herein, the term "sulfinyl" refers to the group —S—(O)R$_c$, wherein R$_c$ is substituted alkyl, substituted carbocycle, aryl, heteroaryl or heterocyclic, as defined above.

As used herein, the term "sulfonyl" refers to the group —S(O)$_2$R$_c$, wherein R$_c$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —NH$_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —S(O)$_2$NH$_2$. The aminosulfonyl group is optionally substituted by substituted alkyl, substituted carbocycle, aryl, heteroaryl or heterocyclic, as defined above.

As used herein, the term "sulfonylamino" refers to the group —NHS(O)$_2$R$_c$ wherein R$_c$ is substituted alkyl, substituted carbocycle, aryl, heteroaryl or heterocyclic, as defined above.

As used herein, the term "carboxyamide" refers to the group —NHC(O)R$_c$ wherein R$_c$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —C(O)NH$_2$. The aminocarbonyl group is optionally substituted by substituted alkyl, substituted carbocycle, aryl, heteroaryl or heterocyclic, as defined above.

As used herein, the term "ureido" refers to the group —NHC(O)NHR$_c$ wherein R$_c$ is hydrogen, alkyl, carbocycle or aryl as defined above.

As used herein, the term "guanidino" refers to the group —NHC(=NH)NH$_2$.

As used herein, the term "acyl" refers to the group —C(O)R$_c$, wherein R$_c$ is alkyl, carbocycle, or heterocyclic as defined herein.

As used herein, the term "aroyl" refers to the group —C(O)R$_b$, wherein R$_b$ is aryl as defined herein.

As used herein, the term "heteroaroyl" refers to the group —C(O)R$_d$, wherein R$_d$ is heteroaryl as defined herein.

As used herein, the term "acyloxy" refers to the group —OC(O)R$_c$, wherein R$_c$ is alkyl, carbocycle, or heterocyclic as defined herein.

As used herein, the term "aroyloxy" refers to the group —OC(O)R$_b$, wherein R$_b$ is aryl as defined herein.

As used herein, the term "heteroaroyloxy" refers to the group —OC(O)R$_d$, wherein R$_d$ is heteroaryl as defined herein.

It is to be understood that the present invention also includes a pharmaceutically acceptable salt and an addition salt of the inventive compound, such as a hydrochloride, hydrobromide or trifluoroacetate addition salt and a sodium, potassium and magnesium salt.

The compounds of the present invention may contain one or more asymmetric carbon atoms and may exist in racemic and optically active forms. All of these compounds and diastereomers are incorporated within the scope of the present invention.

One embodiment of the present invention is to provide a compound of formula (Ia) or a pharmaceutically acceptable salt thereof:

(Ia)

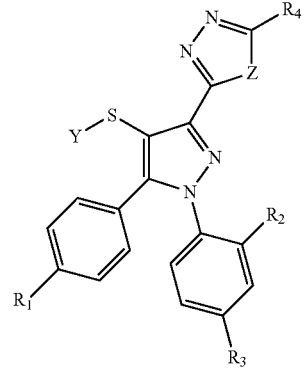

wherein, R$_1$, R$_2$, R$_3$, R$_4$, Y and Z have the same meanings as defined above.

Another embodiment of the present invention is to provide a compound of formula (Ib) or a pharmaceutically acceptable salt thereof:

(Ib)

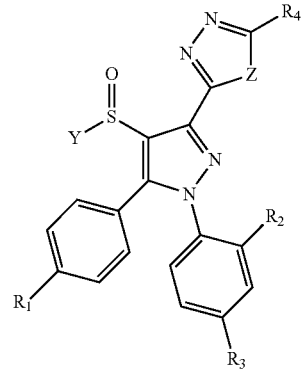

wherein, $R_1$, $R_2$, $R_3$, $R_4$, Y and Z have the same meanings as defined above.

A still another embodiment of the present invention is to provide a compound of formula (Ic) or a pharmaceutically acceptable salt thereof:

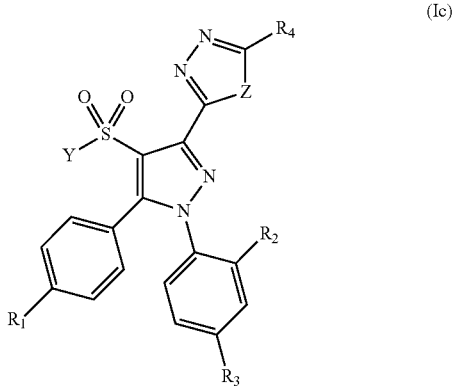

(Ic)

wherein, $R_1$, $R_2$, $R_3$, $R_4$, Y and Z have the same meanings as defined above.

Preferred compounds useful in the present invention are selected from the group consisting of:

2-tert-butyl-5-(5-(4-chlorophenyl)-1-(2,4-dichlorophenyl)-4-(methylthio)-1H-pyrazol-3-yl)-1,3,4-oxadiazole;

2-(5-(4-chlorophenyl)-1-(2,4-dichlorophenyl)-4-(methylthio)-1H-pyrazol-3-yl)-5-(1-(trifluoromethyl)cyclopropyl)-1,3,4-oxadiazole;

2-(5-(4-chlorophenyl)-1-(2,4-dichlorophenyl)-4-(methylthio)-1H-pyrazol-3-yl)-5-(1-(trifluoromethyl)cyclobutyl)-1,3,4-oxadiazole;

2-(5-(4-chlorophenyl)-1-(2,4-dichlorophenyl)-4-(methylthio)-1H-pyrazol-3-yl)-5-(1-(4-chlorophenyl)cyclopropyl)-1,3,4-oxadiazole;

2-tert-butyl-5-(1-(2-chlorophenyl)-5-(4-chlorophenyl)-4-(methylthio)-1H-pyrazol-3-yl)-1,3,4-oxadiazole;

2-(1-(2-chlorophenyl)-5-(4-chlorophenyl)-4-(methylthio)-1H-pyrazol-3-yl)-5-(1-(trifluoromethyl)cyclopropyl)-1,3,4-oxadiazole;

2-(1-(2-chlorophenyl)-5-(4-chlorophenyl)-4-(methylthio)-1H-pyrazol-3-yl)-5-(1-(trifluoromethyl)cyclobutyl)-1,3,4-oxadiazole;

2-(1-(2-chlorophenyl)-5-(4-chlorophenyl)-4-(methylthio)-1H-pyrazol-3-yl)-5-(1-(4-chlorophenyl)cyclopropyl)-1,3,4-oxadiazole;

2-(5-(4-cromophenyl)-1-(2,4-dichlorophenyl)-4-(methylthio)-1H-pyrazol-3-yl)-5-tert-butyl-1,3,4-oxadiazole;

2-(5-(4-bromophenyl)-1-(2,4-dichlorophenyl)-4-(methylthio)-1H-pyrazol-3-yl)-5-(1-(trifluoromethyl)cyclopropyl)-1,3,4-oxadiazole;

2-(5-(4-bromophenyl)-1-(2,4-dichlorophenyl)-4-(methylthio)-1H-pyrazol-3-yl)-5-(1-(trifluoromethyl)cyclobutyl)-1,3,4-oxadiazole;

2-(5-(4-bromophenyl)-1-(2,4-dichlorophenyl)-4-(methylthio)-1H-pyrazol-3-yl)-5-(1-(4-chlorophenyl)cyclopropyl)-1,3,4-oxadiazole;

2-(5-(4-bromophenyl)-1-(2-chlorophenyl)-4-(methylthio)-1H-pyrazol-3-yl)-5-tert-butyl-1,3,4-oxadiazole;

2-(5-(4-bromophenyl)-1-(2-chlorophenyl)-4-(methylthio)-1H-pyrazol-3-yl)-5-(1-(trifluoromethyl)cyclopropyl)-1,3,4-oxadiazole;

2-(5-(4-bromophenyl)-1-(2-chlorophenyl)-4-(methylthio)-1H-pyrazol-3-yl)-5-(1-(trifluoromethyl)cyclobutyl)-1,3,4-oxadiazole;

2-(5-(4-bromophenyl)-1-(2-chlorophenyl)-4-(methylthio)-1H-pyrazol-3-yl)-5-(1-(4-chlorophenyl)cyclopropyl)-1,3,4-oxadiazole;

2-tert-butyl-5-(5-(4-chlorophenyl)-1-(2,4-dichlorophenyl)-4-(ethylthio)-1H-pyrazol-3-yl)-1,3,4-oxadiazole;

2-(5-(4-chlorophenyl)-1-(2,4-dichlorophenyl)-4-(ethylthio)-1H-pyrazol-3-yl)-5-(1-(trifluoromethyl)cyclopropyl)-1,3,4-oxadiazole;

2-(5-(4-chlorophenyl)-1-(2,4-dichlorophenyl)-4-(ethylthio)-1H-pyrazol-3-yl)-5-(1-(trifluoromethyl)cyclobutyl)-1,3,4-oxadiazole;

2-(5-(4-chlorophenyl)-1-(2,4-dichlorophenyl)-4-(ethylthio)-1H-pyrazol-3-yl)-5-(1-(4-chlorophenyl)cyclopropyl)-1,3,4-oxadiazole;

2-tert-butyl-5-(5-(4-chlorophenyl)-1-(2,4-dichlorophenyl)-4-(methylthio)-1H-pyrazol-3-yl)-1,3,4-thiadiazole;

2-(5-(4-chlorophenyl)-1-(2,4-dichlorophenyl)-4-(methylthio)-1H-pyrazol-3-yl)-5-(1-(trifluoromethyl)cyclopropyl)-1,3,4-thiadiazole;

2-(5-(4-chlorophenyl)-1-(2,4-dichlorophenyl)-4-(methylthio)-1H-pyrazol-3-yl)-5-(1-(trifluoromethyl)cyclobutyl)-1,3,4-thiadiazole;

2-(5-(4-chlorophenyl)-1-(2,4-dichlorophenyl)-4-(methylthio)-1H-pyrazol-3-yl)-5-(1-(4-chlorophenyl)cyclopropyl)-1,3,4-thiadiazole;

2-tert-butyl-5-(1-(2-chlorophenyl)-5-(4-chlorophenyl)-4-(methylthio)-1H-pyrazol-3-yl)-1,3,4-thiadiazole;

2-(1-(2-chlorophenyl)-5-(4-chlorophenyl)-4-(methylthio)-1H-pyrazol-3-yl)-5-(1-(trifluoromethyl)cyclopropyl)-1,3,4-thiadiazole;

2-(1-(2-chlorophenyl)-5-(4-chlorophenyl)-4-(methylthio)-1H-pyrazol-3-yl)-5-(1-(trifluoromethyl)cyclobutyl)-1,3,4-thiadiazole;

2-(1-(2-chlorophenyl)-5-(4-chlorophenyl)-4-(methylthio)-1H-pyrazol-3-yl)-5-(1-(4-chlorophenyl)cyclopropyl)-1,3,4-thiadiazole;

2-(5-(4-bromophenyl)-1-(2,4-dichlorophenyl)-4-(methylthio)-1H-pyrazol-3-yl)-5-tert-butyl-1,3,4-thiadiazole;

2-(5-(4-bromophenyl)-1-(2,4-dichlorophenyl)-4-(methylthio)-1H-pyrazol-3-yl)-5-(1-(trifluoromethyl)cyclopropyl)-1,3,4-thiadiazole;

2-(5-(4-bromophenyl)-1-(2,4-dichlorophenyl)-4-(methylthio)-1H-pyrazol-3-yl)-5-(1-(trifluoromethyl)cyclobutyl)-1,3,4-thiadiazole;

2-(5-(4-bromophenyl)-1-(2,4-dichlorophenyl)-4-(methylthio)-1H-pyrazol-3-yl)-5-(1-(4-chlorophenyl)cyclopropyl)-1,3,4-thiadiazole;

2-(5-(4-bromophenyl)-1-(2-chlorophenyl)-4-(methylthio)-1H-pyrazol-3-yl)-5-tert-butyl-1,3,4-thiadiazole;

2-(5-(4-bromophenyl)-1-(2-chlorophenyl)-4-(methylthio)-1H-pyrazol-3-yl)-5-(1-(trifluoromethyl)cyclopropyl)-1,3,4-thiadiazole;

2-(5-(4-bromophenyl)-1-(2-chlorophenyl)-4-(methylthio)-1H-pyrazol-3-yl)-5-(1-(trifluoromethyl)cyclobutyl)-1,3,4-thiadiazole;

2-(5-(4-bromophenyl)-1-(2-chlorophenyl)-4-(methylthio)-1H-pyrazol-3-yl)-5-(1-(4-chlorophenyl)cyclopropyl)-1,3,4-thiadiazole;

2-tert-butyl-5-(5-(4-chlorophenyl)-1-(2,4-dichlorophenyl)-4-(ethylthio)-1H-pyrazol-3-yl)-1,3,4-thiadiazole;

2-(5-(4-chlorophenyl)-1-(2,4-dichlorophenyl)-4-(ethylthio)-1H-pyrazol-3-yl)-5-(1-(trifluoromethyl)cyclopropyl)-1,3,4-thiadiazole;

2-(5-(4-chlorophenyl)-1-(2,4-dichlorophenyl)-4-(ethylthio)-1H-pyrazol-3-yl)-5-(1-(trifluoromethyl)cyclobutyl)-1,3,4-thiadiazole;
2-(5-(4-chlorophenyl)-1-(2,4-dichlorophenyl)-4-(ethylthio)-1H-pyrazol-3-yl)-5-(1-(4-chlorophenyl)cyclopropyl)-1,3,4-thiadiazole;
2-tert-butyl-5-(5-(4-chlorophenyl)-1-(2,4-dichlorophenyl)-4-(methylsulfinyl)-1H-pyrazol-3-yl)-1,3,4-oxadiazole;
2-(5-(4-chlorophenyl)-1-(2,4-dichlorophenyl)-4-(methylsulfinyl)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(methylsulfinyl)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(methylsulfinyl)-1H-pyrazol-3-yl)-5-(1-(4-chlorophenyl)cyclopropyl)-1,3,4-oxadiazole;
2-tert-butyl-5-(1-(2-chlorophenyl)-5-(4-chlorophenyl)-4-(methylsulfinyl)-1H-pyrazol-3-yl)-1,3,4-oxadiazole;
2-(1-(2-chlorophenyl)-5-(4-chlorophenyl)-4-(methylsulfinyl)-1H-pyrazol-3-yl)-5-(1-(trifluoromethyl)cyclopropyl)-1,3,4-oxadiazole;
2-(1-(2-chlorophenyl)-5-(4-chlorophenyl)-4-(methylsulfinyl)-1H-pyrazol-3-yl)-5-(1-(trifluoromethyl)cyclobutyl)-1,3,4-oxadiazole;
2-(1-(2-chlorophenyl)-5-(4-chlorophenyl)-4-(methylsulfinyl)-1H-pyrazol-3-yl)-5-(1-(4-chlorophenyl)cyclopropyl)-1,3,4-oxadiazole;
2-(5-(4-bromophenyl)-1-(2,4-dichlorophenyl)-4-(methylsulfinyl)-1H-pyrazol-3-yl)-5-tert-butyl-1,3,4-oxadiazole;
2-(5-(4-bromophenyl)-1-(2,4-dichlorophenyl)-4-(methylsulfinyl)-1H-pyrazol-3-yl)-5-(1-(trifluoromethyl)cyclopropyl)-1,3,4-oxadiazole;
2-(5-(4-bromophenyl)-1-(2,4-dichlorophenyl)-4-(methylsulfinyl)-1H-pyrazol-3-yl)-5-(1-(trifluoromethyl)cyclobutyl)-1,3,4-oxadiazole;
2-(5-(4-bromophenyl)-1-(2,4-dichlorophenyl)-4-(methylsulfinyl)-1H-pyrazol-3-yl)-5-(1-(4-chlorophenyl)cyclopropyl)-1,3,4-oxadiazole;
2-(5-(4-bromophenyl)-1-(2-chlorophenyl)-4-(methylsulfinyl)-1H-pyrazol-3-yl)-5-tert-butyl-1,3,4-oxadiazole;
2-(5-(4-bromophenyl)-1-(2-chlorophenyl)-4-(methylsulfinyl)-1H-pyrazol-3-yl)-5-(1-(trifluoromethyl)cyclopropyl)-1,3,4-oxadiazole;
2-(5-(4-bromophenyl)-1-(2-chlorophenyl)-4-(methylsulfinyl)-1H-pyrazol-3-yl)-5-(1-(trifluoromethyl)cyclobutyl)-1,3,4-oxadiazole;
2-tert-butyl-5-(5-(4-chlorophenyl)-1-(2,4-dichlorophenyl)-4-(ethylsulfinyl)-1H-pyrazol-3-yl)-1,3,4-oxadiazole;
2-(5-(4-chlorophenyl)-1-(2,4-dichlorophenyl)-4-(ethylsulfinyl)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(ethylsulfinyl)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(ethylsulfinyl)-1H-pyrazol-3-yl)-5-(1-(4-chlorophenyl)cyclopropyl)-1,3,4-oxadiazole;
2-tert-butyl-5-(5-(4-chlorophenyl)-1-(2,4-dichlorophenyl)-4-(methylsulfinyl)-1H-pyrazol-3-yl)-1,3,4-thiadiazole;
2-(5-(4-chlorophenyl)-1-(2,4-dichlorophenyl)-4-(methylsulfinyl)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(methylsulfinyl)-1H-pyrazol-3-yl)-5-(1-(trifluoromethyl)cyclobutyl)-1,3,4-thiadiazole;
2-(5-(4-chlorophenyl)-1-(2,4-dichlorophenyl)-4-(methylsulfinyl)-1H-pyrazol-3-yl)-5-(1-(4-chlorophenyl)cyclopropyl)-1,3,4-thiadiazole;
2-tert-butyl-5-(1-(2-chlorophenyl)-5-(4-chlorophenyl)-4-(methylsulfinyl)-1H-pyrazol-3-yl)-1,3,4-thiadiazole;
2-(1-(2-chlorophenyl)-5-(4-chlorophenyl)-4-(methylsulfinyl)-1H-pyrazol-3-yl)-5-(1-(trifluoromethyl)cyclopropyl)-1,3,4-thiadiazole;
2-(1-(2-chlorophenyl)-5-(4-chlorophenyl)-4-(methylsulfinyl)-1H-pyrazol-3-yl)-5-(1-(trifluoromethyl)cyclobutyl)-1,3,4-thiadiazole;
2-(1-(2-chlorophenyl)-5-(4-chlorophenyl)-4-(methylsulfinyl)-1H-pyrazol-3-yl)-5-(1-(4-chlorophenyl)cyclopropyl)-1,3,4-thiadiazole;
2-(5-(4-bromophenyl)-1-(2,4-dichlorophenyl)-4-(methylsulfinyl)-1H-pyrazol-3-yl)-5-tert-butyl-1,3,4-thiadiazole;
2-(5-(4-bromophenyl)-1-(2,4-dichlorophenyl)-4-(methylsulfinyl)-1H-pyrazol-3-yl)-5-(1-(trifluoromethyl)cyclopropyl)-1,3,4-thiadiazole;
2-(5-(4-bromophenyl)-1-(2,4-dichlorophenyl)-4-(methylsulfinyl)-1H-pyrazol-3-yl)-5-(1-(trifluoromethyl)cyclobutyl)-1,3,4-thiadiazole;
2-(5-(4-bromophenyl)-1-(2,4-dichlorophenyl)-4-(methylsulfinyl)-1H-pyrazol-3-yl)-5-(1-(4-chlorophenyl)cyclopropyl)-1,3,4-thiadiazole;
2-(5-(4-bromophenyl)-1-(2-chlorophenyl)-4-(methylsulfinyl)-1H-pyrazol-3-yl)-5-tert-butyl-1,3,4-thiadiazole;
2-(5-(4-bromophenyl)-1-(2-chlorophenyl)-4-(methylsulfinyl)-1H-pyrazol-3-yl)-5-(1-(trifluoromethyl)cyclopropyl)-1,3,4-thiadiazole;
2-(5-(4-bromophenyl)-1-(2-chlorophenyl)-4-(methylsulfinyl)-1H-pyrazol-3-yl)-5-(1-(trifluoromethyl)cyclobutyl)-1,3,4-thiadiazole;
2-(5-(4-bromophenyl)-1-(2-chlorophenyl)-4-(methylsulfinyl)-1H-pyrazol-3-yl)-5-(1-(4-chlorophenyl)cyclopropyl)-1,3,4-thiadiazole;
2-tert-butyl-5-(5-(4-chlorophenyl)-1-(2,4-dichlorophenyl)-4-(ethylsulfinyl)-1H-pyrazol-3-yl)-1,3,4-thiadiazole;
2-(5-(4-chlorophenyl)-1-(2,4-dichlorophenyl)-4-(ethylsulfinyl)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(ethylsulfinyl)-1H-pyrazol-3-yl)-5-(1-(trifluoromethyl)cyclobutyl)-1,3,4-thiadiazole;
2-(5-(4-chlorophenyl)-1-(2,4-dichlorophenyl)-4-(ethylsulfinyl)-1H-pyrazol-3-yl)-5-(1-(4-chlorophenyl)cyclopropyl)-1,3,4-thiadiazole;
2-tert-butyl-5-(5-(4-chlorophenyl)-1-(2,4-dichlorophenyl)-4-(methylsulfonyl)-1H-pyrazol-3-yl)-1,3,4-oxadiazole;
2-(5-(4-chlorophenyl)-1-(2,4-dichlorophenyl)-4-(methylsulfonyl)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(methylsulfonyl)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(methylsulfonyl)-1H-pyrazol-3-yl)-5-(1-(4-chlorophenyl)cyclopropyl)-1,3,4-oxadiazole;
2-tert-butyl-5-(1-(2-chlorophenyl)-5-(4-chlorophenyl)-4-(methylsulfonyl)-1H-pyrazol-3-yl)-1,3,4-oxadiazole;
2-(1-(2-chlorophenyl)-5-(4-chlorophenyl)-4-(methylsulfonyl)-1H-pyrazol-3-yl)-5-(1-(trifluoromethyl)cyclopropyl)-1,3,4-oxadiazole;
2-(1-(2-chlorophenyl)-5-(4-chlorophenyl)-4-(methylsulfonyl)-1H-pyrazol-3-yl)-5-(1-(trifluoromethyl)cyclobutyl)-1,3,4-oxadiazole;

2-(1-(2-chlorophenyl)-5-(4-chlorophenyl)-4-(methylsulfonyl)-1H-pyrazol-3-yl)-5-(1-(4-chlorophenyl)cyclopropyl)-1,3,4-oxadiazole;
2-(5-(4-bromophenyl)-1-(2,4-dichlorophenyl)-4-(methylsulfonyl)-1H-pyrazol-3-yl)-5-tert-butyl-1,3,4-oxadiazole;
2-(5-(4-bromophenyl)-1-(2,4-dichlorophenyl)-4-(methylsulfonyl)-1H-pyrazol-3-yl)-5-(1-(trifluoromethyl)cyclopropyl)-1,3,4-oxadiazole;
2-(5-(4-bromophenyl)-1-(2,4-dichlorophenyl)-4-(methylsulfonyl)-1H-pyrazol-3-yl)-5-(1-(trifluoromethyl)cyclobutyl)-1,3,4-oxadiazole;
2-(5-(4-bromophenyl)-1-(2,4-dichlorophenyl)-4-(methylsulfonyl)-1H-pyrazol-3-yl)-5-(1-(4-chlorophenyl)cyclopropyl)-1,3,4-oxadiazole;
2-(5-(4-bromophenyl)-1-(2-chlorophenyl)-4-(methylsulfonyl)-1H-pyrazol-3-yl)-5-tert-butyl-1,3,4-oxadiazole;
2-(5-(4-bromophenyl)-1-(2-chlorophenyl)-4-(methylsulfonyl)-1H-pyrazol-3-yl)-5-(1-(trifluoromethyl)cyclopropyl)-1,3,4-oxadiazole;
2-(5-(4-bromophenyl)-1-(2-chlorophenyl)-4-(methylsulfonyl)-1H-pyrazol-3-yl)-5-(1-(trifluoromethyl)cyclobutyl)-1,3,4-oxadiazole;
2-(5-(4-bromophenyl)-1-(2-chlorophenyl)-4-(methylsulfonyl)-1H-pyrazol-3-yl)-5-(1-(4-chlorophenyl)cyclopropyl)-1,3,4-oxadiazole;
2-tert-butyl-5-(5-(4-chlorophenyl)-1-(2,4-dichlorophenyl)-4-(ethylsulfonyl)-1H-pyrazol-3-yl)-1,3,4-oxadiazole;
2-(5-(4-chlorophenyl)-1-(2,4-dichlorophenyl)-4-(ethylsulfonyl)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(ethylsulfonyl)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(ethylsulfonyl)-1H-pyrazol-3-yl)-5-(1-(4-chlorophenyl)cyclopropyl)-1,3,4-oxadiazole;
2-tert-butyl-5-(5-(4-chlorophenyl)-1-(2,4-dichlorophenyl)-4-(methylsulfonyl)-1H-pyrazol-3-yl)-1,3,4-thiadiazole;
2-(5-(4-chlorophenyl)-1-(2,4-dichlorophenyl)-4-(methylsulfonyl)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(methylsulfonyl)-1H-pyrazol-3-yl)-5-(1-(trifluoromethyl)cyclobutyl)-1,3,4-thiadiazole;
2-(5-(4-chlorophenyl)-1-(2,4-dichlorophenyl)-4-(methylsulfonyl)-1H-pyrazol-3-yl)-5-(1-(4-chlorophenyl)cyclopropyl)-1,3,4-thiadiazole;
2-tert-butyl-5-(1-(2-chlorophenyl)-5-(4-chlorophenyl)-4-(methylsulfonyl)-1H-pyrazol-3-yl)-1,3,4-thiadiazole;
2-(1-(2-chlorophenyl)-5-(4-chlorophenyl)-4-(methylsulfonyl)-1H-pyrazol-3-yl)-5-(1-(trifluoromethyl)cyclopropyl)-1,3,4-thiadiazole;
2-(1-(2-chlorophenyl)-5-(4-chlorophenyl)-4-(methylsulfonyl)-1H-pyrazol-3-yl)-5-(1-(trifluoromethyl)cyclobutyl)-1,3,4-thiadiazole;
2-(1-(2-chlorophenyl)-5-(4-chlorophenyl)-4-(methylsulfonyl)-1H-pyrazol-3-yl)-5-(1-(4-chlorophenyl)cyclopropyl)-1,3,4-thiadiazole;
2-(5-(4-bromophenyl)-1-(2,4-dichlorophenyl)-4-(methylsulfonyl)-1H-pyrazol-3-yl)-5-tert-butyl-1,3,4-thiadiazole;
2-(5-(4-bromophenyl)-1-(2,4-dichlorophenyl)-4-(methylsulfonyl)-1H-pyrazol-3-yl)-5-(1-(trifluoromethyl)cyclopropyl)-1,3,4-thiadiazole;
2-(5-(4-bromophenyl)-1-(2,4-dichlorophenyl)-4-(methylsulfonyl)-1H-pyrazol-3-yl)-5-(1-(trifluoromethyl)cyclobutyl)-1,3,4-thiadiazole;
2-(5-(4-bromophenyl)-1-(2,4-dichlorophenyl)-4-(methylsulfonyl)-1H-pyrazol-3-yl)-5-(1-(4-chlorophenyl)cyclopropyl)-1,3,4-thiadiazole;
2-(5-(4-bromophenyl)-1-(2-chlorophenyl)-4-(methylsulfonyl)-1H-pyrazol-3-yl)-5-tert-butyl-1,3,4-thiadiazole;
2-(5-(4-bromophenyl)-1-(2-chlorophenyl)-4-(methylsulfonyl)-1H-pyrazol-3-yl)-5-(1-(trifluoromethyl)cyclopropyl)-1,3,4-thiadiazole;
2-(5-(4-bromophenyl)-1-(2-chlorophenyl)-4-(methylsulfonyl)-1H-pyrazol-3-yl)-5-(1-(trifluoromethyl)cyclobutyl)-1,3,4-thiadiazole;
2-(5-(4-bromophenyl)-1-(2-chlorophenyl)-4-(methylsulfonyl)-1H-pyrazol-3-yl)-5-(1-(4-chlorophenyl)cyclopropyl)-1,3,4-thiadiazole;
2-tert-butyl-5-(5-(4-chlorophenyl)-1-(2,4-dichlorophenyl)-4-(ethylsulfonyl)-1H-pyrazol-3-yl)-1,3,4-thiadiazole;
2-(5-(4-chlorophenyl)-1-(2,4-dichlorophenyl)-4-(ethylsulfonyl)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(ethylsulfonyl)-1H-pyrazol-3-yl)-5-(1-(trifluoromethyl)cyclobutyl)-1,3,4-thiadiazole; and
2-(5-(4-chlorophenyl)-1-(2,4-dichlorophenyl)-4-(ethylsulfonyl)-1H-pyrazol-3-yl)-5-(1-(4-chlorophenyl)cyclopropyl)-1,3,4-thiadiazole.

General Synthesis of the Compounds of Formula (I)

The following synthetic schemes are merely illustrative of the methods by which the compounds of the invention may be prepared and are not intended to limit the scope of the invention as defined in the appended claims.

The compound of formula (Ia) may be prepared by (i) reacting a compound of formula (7) with a compound of formula (8) in the presence of a coupling reagent in a solvent to obtain a compound of formula (9); and (ii) cyclizing the compound of formula (9) using a dehydrating agent or sulfurating agent to obtain the compound of formula (Ia):

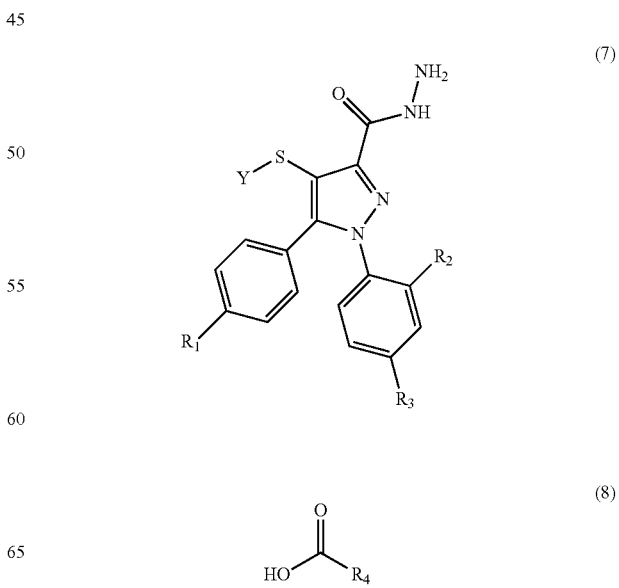

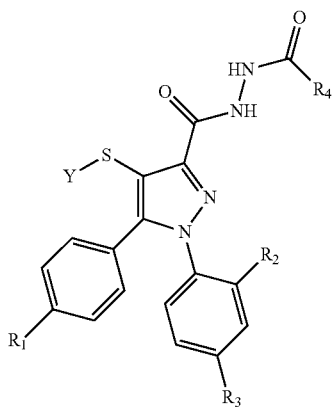

(9)

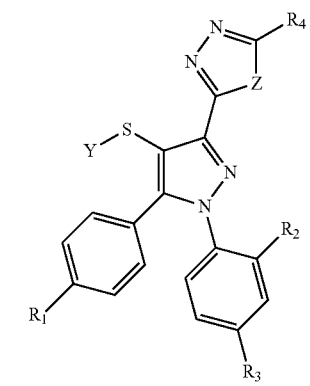

(Ia)

wherein, $R_1$, $R_2$, $R_3$, $R_4$, Y and Z have the same meanings as defined above.

The inventive method for preparing the compound of formula (Ia) is shown in Reaction Scheme 1.

Reaction Scheme 1

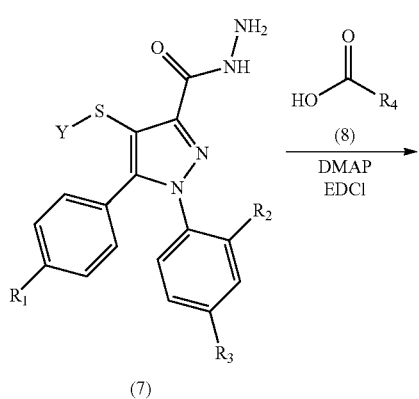

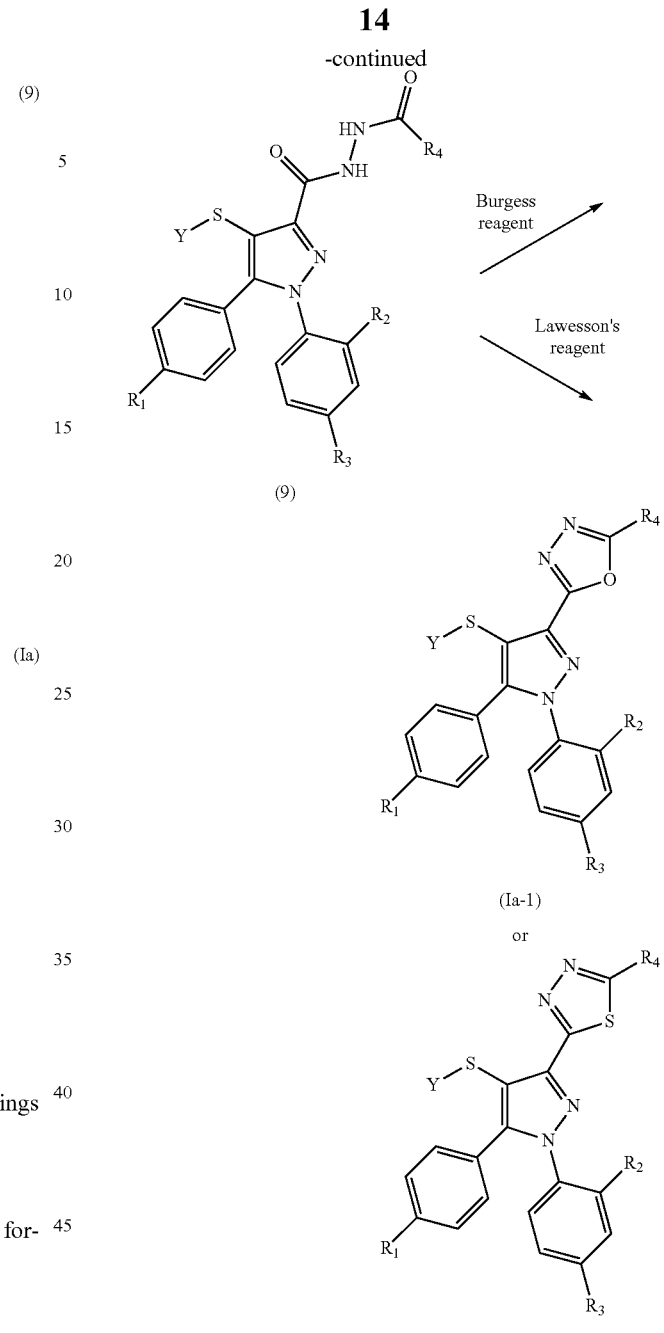

wherein, $R_1$, $R_2$, $R_3$, $R_4$ and Y have the same meanings as defined above.

As shown in Reaction Scheme 1, the compound of formula (Ia-1) may be prepared by (i) reacting a hydrazide compound of formula (7) with an acid compound of formula (8) in the presence of coupling agents, e.g., 1-ethyl-3-[3-dimethylaminopropyl]carbodiimide hydrochloride (EDCI), 4-dimethylaminopyridine (DMAP) in a solvent, e.g., $CH_2Cl_2$, N,N-dimethylformamide (DMF), to obtain a compound of formula (9), and (ii) cyclizing the compound of formula (9) using a Burgess reagent as a dehydrating agent, which can be conducted with microwave irradiation (See Leber, J. D. et al., WO 2005/032550).

The compound of formula (Ia-2) may be prepared by the cyclizing the compound of formula (9) using a Lawesson's reagent as a sulfurating agent, which can be conducted with microwave irradiation (See Kiryanov, A. A., Sampson, P., Seed, A. J., *J. Org. Chem.* 2001, 665, 7925-7929).

The hydrazide compound of formula (7) used as a starting material in preparing the compound of formula (Ia-1) or (Ia-2) may be prepared by a conventional method as shown in Reaction Scheme 2. The bromoacetophenone derivative of formula (1) may be reacted with NaS—Y in a suitable solvent such as THF to provide a corresponding (alkylsulfanyl)ethanone derivative of formula (2). This (alkylsulfanyl)ethanone derivative of formula (2) can be reacted with an oxalic ester derivative of formula (3) in the presence of base such as lithium hexamethyldisilazide (LiHMDS) in an appropriate inert solvent such as methyl t-butyl ether (MTBE) to provide an ethyl 3-(alkylthio)-2,4-dioxo-4-aryllbutanoate of formula (4) (See Mosher, H. S. et al *J. Org. Chem.* 1981, 46, 211-213; Barth, F. et al 2002, U.S. Pat. No. 6,432,984). Alternatively, the compound of formula (4) can be synthesized by treating a sulfanyl compound of formula (2) with diethyl oxalate in the presence of sodium and ethyl alcohol. The compound of formula (4) thus obtained can be reacted with an arylhydrazine compound of formula (5) to provide an ester compound of formula (6). The ester compound of formula (6) can be treated with hydrazine to produce the corresponding hydrazide compound of formula (7).

Reaction Scheme 2

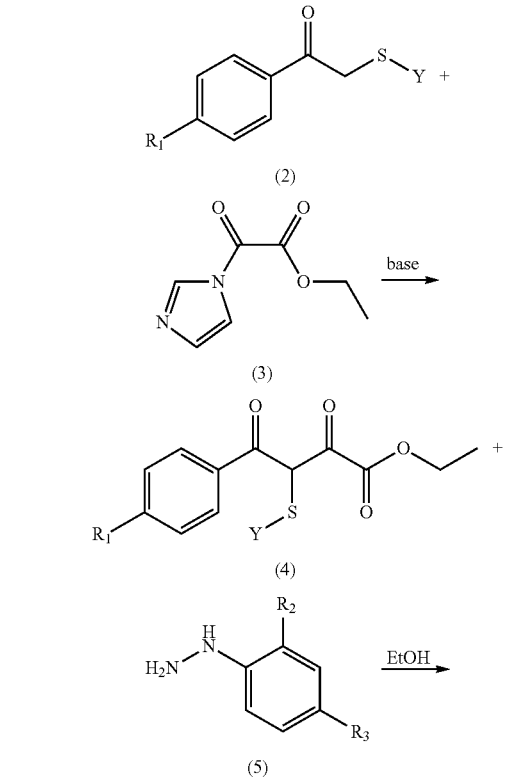

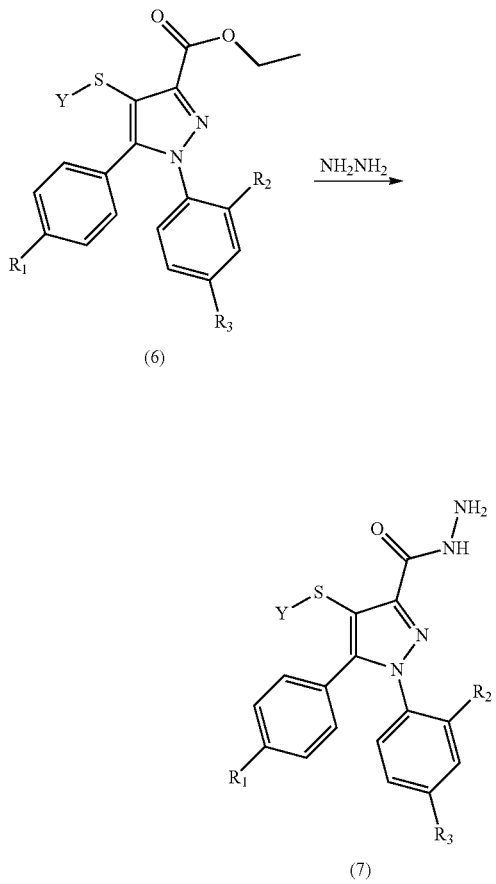

wherein, $R_1$, $R_2$, $R_3$ and Y have the same meanings as defined above.

The compound of formula (Ib) can be prepared by oxidizing the compound of formula (Ia) with 1 to 1.5 equivalents of meta-chloroperbenzoic acid (m-CPBA) in a solvent, e.g., $CH_2Cl_2$, as shown in Reaction Scheme 3:

Reaction Scheme 3

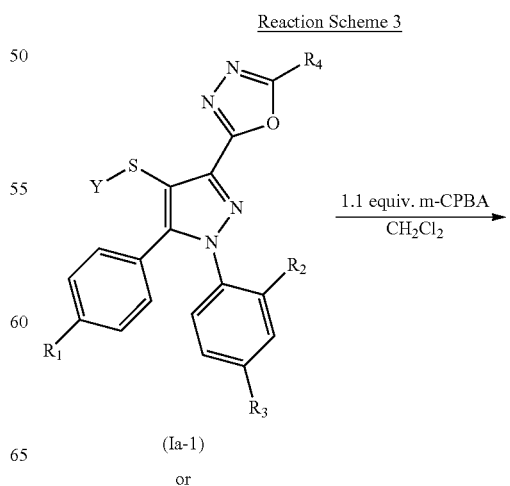

(Ia-1)

or

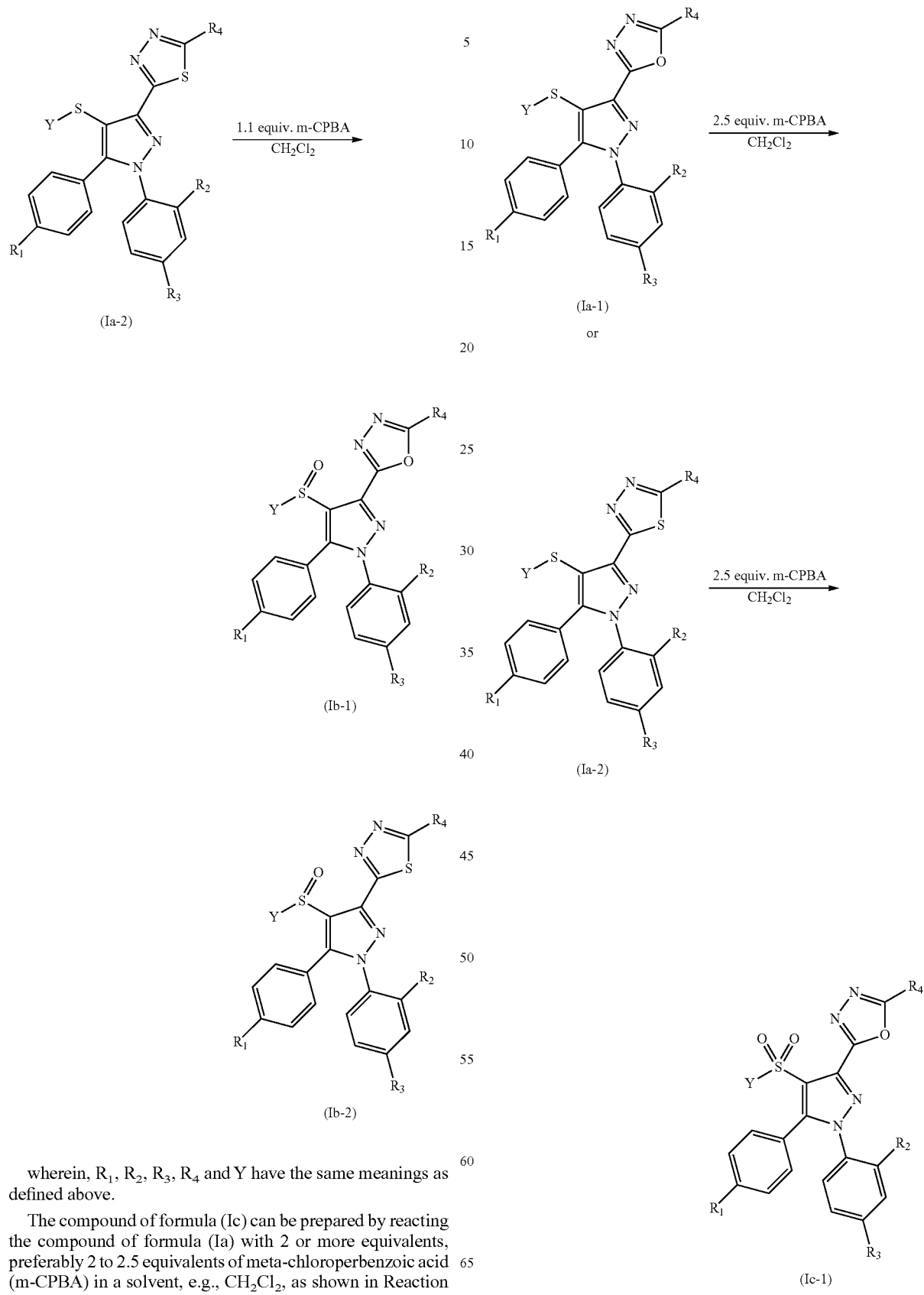
wherein, $R_1$, $R_2$, $R_3$, $R_4$ and Y have the same meanings as defined above.
The compound of formula (Ic) can be prepared by reacting the compound of formula (Ia) with 2 or more equivalents, preferably 2 to 2.5 equivalents of meta-chloroperbenzoic acid (m-CPBA) in a solvent, e.g., $CH_2Cl_2$, as shown in Reaction Scheme 4:

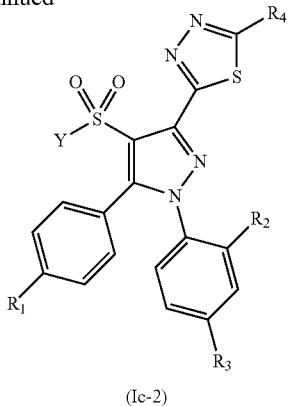

(Ic-2)

wherein, $R_1$, $R_2$, $R_3$, $R_4$ and Y have the same meanings as defined above.

The inventive sulfur containing pyrazole-heterocycle compound of formula (I) is effective as a cannabinoid $CB_1$ receptor inverse agonist or antagonist, thereby preventing or treating obesity and obesity-related metabolic disorders.

Accordingly, the present invention provides a pharmaceutical composition for preventing or treating obesity and obesity-related metabolic disorders, which comprises the compound of formula (I) or a pharmaceutically acceptable salt thereof as an active ingredient and a pharmaceutically acceptable carrier.

Further, the present invention provides a method for preventing or treating obesity and obesity-related metabolic disorders in a mammal, which comprises administering the compound of formula (I) to the mammal.

Also, the present invention provides a method for inhibiting cannabinoid $CB_1$ receptor in a mammal, which comprises administering the compound of formula (I) to the mammal.

As used herein, the term "obesity-related metabolic disorders" refers to chronic diseases that require treatment to reduce the excessive health risks associated with obesity and exemplary disorders include type 2 diabetes mellitus, cardiovascular and hypertension, hyperlipidaemia, fibrinolytic abnormalities.

The pharmaceutical composition may be administered orally, intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg/Kg, and preferably from 1 mg to 100 mg/Kg of the compound of Formula (I) or its pharmaceutically acceptable salt.

The suitable daily dosage for oral administration is about 0.01 mg/Kg to 40 mg/Kg of the compound of Formula (I) or its pharmaceutically acceptable salt, may be administered 1 to 6 times a day, depending on the patient's condition.

The present invention is further described and illustrated in Examples provided below, which are, however, not intended to limit the scope of the present invention.

Experimental Section

As used herein the symbols and conventions used describing the processes, schemes and examples of the present invention are consistent with those used in the contemporary scientific literature, for example, the *Journal of the American Chemical Society* or the *Journal of Biological Chemistry*. Unless otherwise noted, all starting materials were obtained from commercial suppliers and used without further purification.

Hz (Hertz) TLC (thin layer chromatography)
$T_r$ (retention time) RP (reverse phase)
MeOH (methanol) i-PrOH (isopropanol)
TFA (trifluoroacetic acid) TEA (triethylamine)
EtOH (ethanol) THF (tetrahydrofuran)
DMSO (dimethylsulfoxide) EtOAc (ethyl acetate)
DCM (dichlromethane) HOAc (acetic acid)
DMF (N,N-dimethylformamide) Ac (acetyl)
CDI (1,1-carbnyldiimidazole) Bn (benzyl)
HOSu (N-hydroxysuccinimide)
HOBT (1-hydroxybenzotriazole)
Boc (tert-butyloxycarbonyl)
m-CPBA (meta-chloroperbenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)phosphinic chloride);
EDCI (1-ethyl-3-[3-dimethylaminopropyl]carbodiimide hydrochloride)
HBTU (O-Benzotriazolel-yl-N,N,N',N'-tetramethyluronium hexafluoro phosphate)
MTBE (methyl t-butyl ether)

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are of the highest available purity unless otherwise indicated.

Microwave reaction was conducted with a Biotage Initiator™ microwave synthesizer.

$^1$H NMR spectra were recorded on either a Jeol ECX-400, or a Jeol JNM-LA300 spectrometer. Chemical shifts were expressed in parts per million (ppm, δ units). Coupling constants are in units of hertz (Hz). Splitting patterns describe apparent multiplicities and are designated as s (singlet), d(doublet), t (triplet), q (quartet), quint (quintet), m (multiplet), br (broad).

Mass spectra were obtained with either a Micromass, Quattro LC Triple Quadruple Tandem Mass Spectometer, ESI or Agilent, 1100LC/MSD, ESI.

For preparative HPLC, ca 100 mg of a product was injected in 1 mL of DMSO onto a SunFire™ Prep C18 OBD 5 μm 19×100 mm Column with a 10 min gradient from 10% CH₃CN to 90% CH₃CN in H₂O (purification systems from Gilson, Inc). Flash chromatography was carried using Merck silica gel 60 (230-400 mesh). Biotage SP1™ FLASH Purification System and Biotage Isolera™ FLASH Purification System were used for normal phase column chromatography with ethyl acetate and hexane. Most of the reactions were monitored by thin-layer chromatography on 0.25 mm E. Merck silica gel plates (60F-254), visualized with UV light using a 5% ethanolic phosphomolybdic acid or p-anisaldehyde solution.

The following synthetic schemes are merely illustrative of the methods by which the compounds of the invention may be prepared and are not intended to limit the scope of the invention as defined in the appended claims.

Preparation of ethyl 5-(4-chlorophenol)-1-(2,4-dichlorophenyl)-4-(methylthio)-1H-pyrazole-3-carboxylate (formula (6))

Step 1: 1-(4-chlorophenyl)-2-(methylthio)ethanone (2)

To a suspension of 2-bromo-1-(4-chlorophenyl)ethanone (1, 20 g, 86 mmol) in tetrahydrofuran (250 ml) was added sodium methanethiolate (7.2 g, 103 mmol) in tetrahydrofuran (250 ml) at −40° C. and the mixture was stirred for 1 hour. The mixture was diluted with diethyl ether and filtered off, and the filtrate was washed with brine. The solvent was evaporated off under the reduced pressure, and the residue was subjected to silica gel column chromatography (Biotage) to obtain 15 g of the title compound.

¹H NMR (400 MHz, CDCl₃) δ 7.93-7.88 (m, 2H), 7.45-7.42 (m, 2H), 3.71 (s, 2H), 2.12 (s, 3H).

Step 2: ethyl 2-(1H-imidazol-1-yl)-2-oxoacetate (3)

To a suspension of imidazole (12.2 g, 175 mmol) in tetrahydrofuran (250 ml) was added ethyl chlorooxoacetate (10 mL, 90 mmol) in tetrahydrofuran (250 ml) at 0° C., and the mixture was stirred for 1 hour and then filtered off and washed with cold tetrahydarofuran (100 mL). The solvent was evaporated off under the reduced pressure to obtain 14.4 g of the title compound.

Step 3: ethyl 4-(4-chlorophenyl)-3-(methylthio)-2,4-dioxobutanoate (4)

To a solution of 15 g of 1-(4-chlorophenyl)-2-(methylthio) ethanone (2) in 70 mL of MTBE is added a solution of 86 mL of lithium hexamethyldisilazide (LiHMDS) under nitrogen gas, while keeping the temperature at −40° C. After stirring for 1.5 hours at this temperature, 14.4 g of ethyl 2-(1H-imidazol-1-yl)-2-oxoacetate (3) in 50 mL MTBE are added at 0° C., and the mixture is left stirring overnight at room temperature. The reaction solution was filtered off and the filtrate was suspended in 80 mL of MTBE. 50 mL of 6N HCl are added to the suspension. After separation of the phase by settling, the ether phase is washed 4 times with water and then concentrated under reduced pressure to obtain 22 g (73 mmol) of the title compound.

Step 4: ethyl 5-(4-chlorophenyl)-1-(2,4-dichlorophenyl)-4-(methylthio)-1H-pyrazole-3-carboxylate (6)

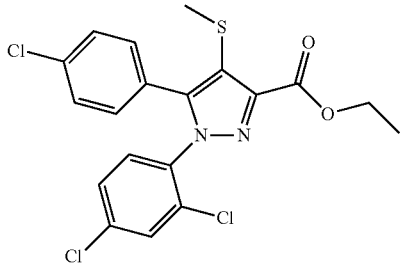

To a solution of 15.6 g of 2,4-dichlorophenylhydrazine hydrochloride (5) in mL of ethanol was added 22 g of ethyl 4-(4-chlorophenyl)-3-(methylthio)-2,4-dioxobutanoate (4) in 120 mL of ethanol at room temperature. After 2 hours, the mixture was refluxed for 15 hours and then cooled to the room temperature. The mixture was filtered off and the filtrate was evaporated off under the reduced pressure, and the residue was subjected to silica gel column chromatography (eluent: hexane/EtOAc mixture (80/20; v/v) to obtain 25 g of the title compound as pale orange color solid.

¹H NMR (400 MHz, CDCl₃) δ 7.40 (m, 1H), 7.38-7.36 (m, 1H), 7.33-7.30 (m, 3H), 7.19-7.17 (m, 2H), 4.49 (q, 2H, J=7.2 Hz), 2.33 (s, 3H), 1.45 (t, 3H, J=7.0 Hz).

MH+441.

Preparation of 1,3,4-oxadiazole (formula (Ia-1))

Example 1

2-tert-butyl-5-(5-(4-chlorophenyl)-1-(2,4-dichlorophenyl)-4-(methylthio)-1H-pyrazol-3-yl)-1,3,4-oxadiazole (Ia-1)

Step 1: 5-(4-chlorophenyl)-1-(2,4-dichlorophenyl)-4-(methylthio)-1H-pyrazole-3-carbohydrazide (7)

To a solution of ethyl 5-(4-chlorophenyl)-1-(2,4-dichlorophenyl)-4-(methylthio)-1H-pyrazole-3-carboxylate (6) (300 mg, 0.68 mmol) in EtOH (5 mL) was added hydrazine monohydrate (1 mL). The reaction mixture was refluxed for 2 h at 90° C. Reaction mixture was diluted with EtOAc and washed with saturated NaCl. The organic layer was dried over anhydrous MgSO₄, filtered, and concentrated in vacuo to obtain 200 mg (70%) of the title compound as a white solid. The obtained compound was used for the next step without further purification.

MH+427.

Step 2: 5-(4-chlorophenyl)-1-(2,4-dichlorophenyl)-4-(methylthio)-N'-pivaloyl-1H-pyrazole-3-carbohydrazide (9)

To a solution of 5-(4-chlorophenyl)-1-(2,4-dichlorophenyl)-4-(methylthio)-1H-pyrazole-3-carbohydrazide (7) (200 mg, 0.47 mmol), pivalic acid (8) (57 mg, 0.56 mmol) and EDCI (134 mg, 0.70 mmol) dissolved in CH₂Cl₂ (30 ml) was added DMAP (114 mg, 0.93 mmol) in one portion at room temperature. The reaction mixture was stirred at room temperature for 12 hrs, and then treated with 1N—HCl solution. The organic layer was collected, and evaporated under a vacuum. The crude mixture was further purified by preparative HPLC, to obtain 150 mg (63%) of the title compound as a white solid.

MH+511.

Step 3: 2-tert-butyl-5-(5-(4-chlorophenyl)-1-(2,4-dichlorophenyl)-4-(methylthio)-1H-pyrazol-3-yl)-1,3,4-oxadiazole (Ia-1)

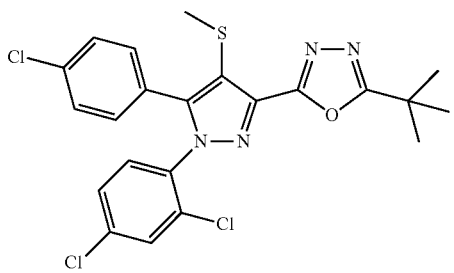

To a solution of 5-(4-chlorophenyl)-1-(2,4-dichlorophenyl)-4-(methylthio)-N'-pivaloyl-1H-pyrazole-3-carbohydrazide (9) (80 mg, 0.156 mmol) and Burgess reagent (111 mg, 0.468 mmol) in THF (5 mL) was irradiated in a microwave reactor (Biotage Initiator™) for 50 minutes at 155° C. The organic extract was dried over anhydrous MgSO$_4$, filtered, and concentrated in vacuo. The residue was subjected to flash column chromatography (Biotage SP1™) to obtain 38 mg (50%) of the title compound as a white solid.

$^1$H NMR (400 MHz, CDCl$_3$) δ 7.42-7.39 (m, 2H), 7.35-7.30 (m, 3H), 7.22-7.19 (m, 2H), 2.39 (s, 3H), 1.50 (s, 9H).

MH+493.

The following compounds of Examples 2 to 20 were obtained by using corresponding starting materials and repeating the procedure of Example 1.

Example 2

2-(5-(4-chlorophenyl)-1-(2,4-dichlorophenyl)-4-(methylthio)-1H-pyrazol-3-yl)-5-(1-(trifluoromethyl)cyclopropyl)-1,3,4-oxadiazole

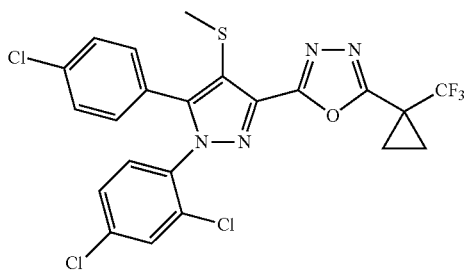

$^1$H NMR (400 MHz, CDCl$_3$) δ 7.44-7.40 (m, 2H), 7.36-7.34 (m, 3H), 7.22-7.21 (m, 2H), 2.39 (s, 3H), 1.70-1.62 (m, 4H).

MH+545.

Example 3

2-(5-(4-chlorophenyl)-1-(2,4-dichlorophenyl)-4-(methylthio)-1H-pyrazol-3-yl)-5-(1-(trifluoromethyl)cyclobutyl)-1,3,4-oxadiazole

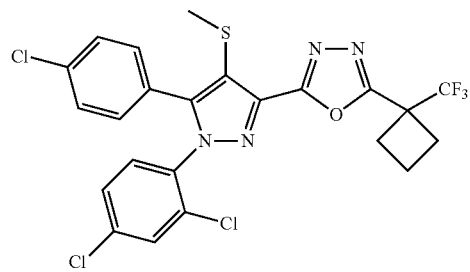

$^1$H NMR (400 MHz, CDCl$_3$) δ 7.44-7.41 (m, 2H), 7.37-7.34 (m, 3H), 7.24-7.21 (m, 2H), 2.90-2.77 (m, 4H), 2.40 (s, 3H), 2.22-2.14 (m, 2H).

MH+559.

Example 4

2-(5-(4-chlorophenyl)-1-(2,4-dichlorophenyl)-4-(methylthio)-1H-pyrazol-3-yl)-5-(1-(4-chlorophenyl)cyclopropyl)-1,3,4-oxadiazole

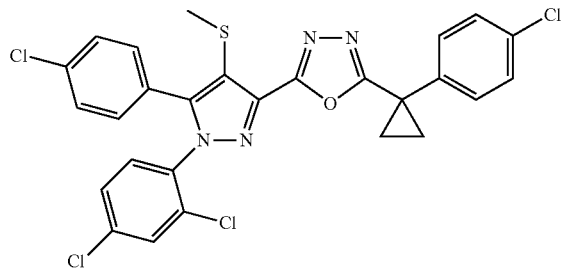

$^1$H NMR (400 MHz, CDCl$_3$) δ 7.44-7.42 (m, 3H), 7.39-7.37 (m, 1H), 7.34-7.32 (m, 5H), 7.20-7.18 (m, 2H), 2.31 (s, 3H), 1.83-1.80 (m, 2H), 1.49-1.46 (m, 2H).

MH+587.

Example 5

2-tert-butyl-5-(1-(2-chlorophenyl)-5-(4-chlorophenyl)-4-(methylthio)-1H-pyrazol-3-yl)-1,3,4-oxadiazole

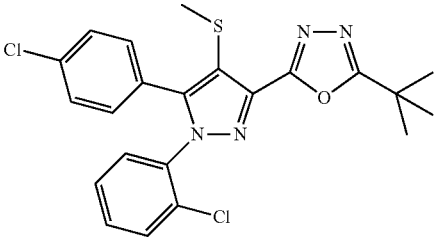

$^1$H NMR (400 MHz, CDCl$_3$) δ 7.48-7.46 (m, 1H), 7.43-7.33 (m, 3H), 7.32-7.30 (m, 2H), 7.27-7.22 (m, 2H), 2.41 (s, 3H), 1.51 (s, 9H).

MH+459.

Example 6

2-(1-(2-chlorophenyl)-5-(4-chlorophenyl)-4-(methylthio)-1H-pyrazol-3-yl)-5-(1-(trifluoromethyl)cyclopropyl)-1,3,4-oxadiazole

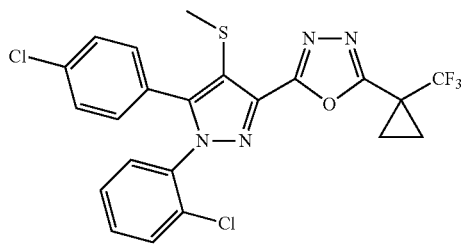

$^1$H NMR (400 MHz, CDCl$_3$) δ 7.47-7.45 (m, 1H), 7.43-7.34 (m, 3H), 7.33-7.30 (m, 2H), 7.24-7.22 (m, 2H), 2.40 (s, 3H), 1.70-1.61 (m, 4H).
MH+511.

Example 7

2-(1-(2-chlorophenyl)-5-(4-chlorophenyl)-4-(methylthio)-1H-pyrazol-3-yl)-5-(1-(trifluoromethyl)cyclobutyl)-1,3,4-oxadiazole

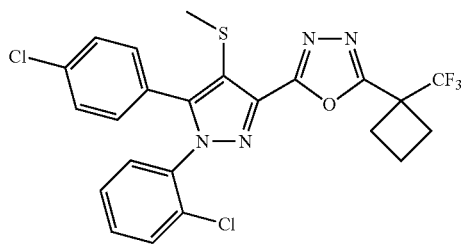

$^1$H NMR (400 MHz, CDCl$_3$) δ 7.48-7.46 (m, 1H), 7.43-7.36 (m, 3H), 7.33-7.31 (m, 2H), 7.24-7.22 (m, 2H), 2.90-2.77 (m, 4H), 2.41 (s, 3H), 2.24-2.14 (q, J=8 Hz, 2H).
MH+525.

Example 8

2-(1-(2-chlorophenyl)-5-(4-chlorophenyl)-4-(methylthio)-1H-pyrazol-3-yl)-5-(1-(4-chlorophenyl)cyclopropyl)-1,3,4-oxadiazole

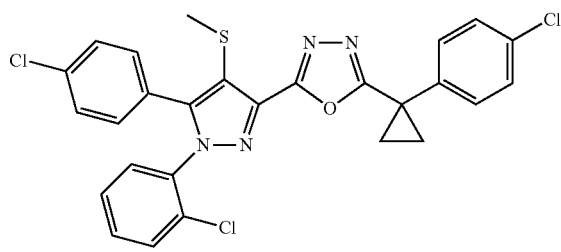

$^1$H NMR (400 MHz, CDCl$_3$) δ 7.45-7.36 (m, 6H), 7.35-7.29 (m, 4H), 7.22-7.20 (m, 2H), 2.33 (s, 3H), 1.84-1.77 (m, 2H), 1.49-1.46 (m, 2H).
MH+553.

Example 9

2-(5-(4-bromophenyl)-1-(2,4-dichlorophenyl)-4-(methylthio)-1H-pyrazol-3-yl)-5-tert-butyl-1,3,4-oxadiazole

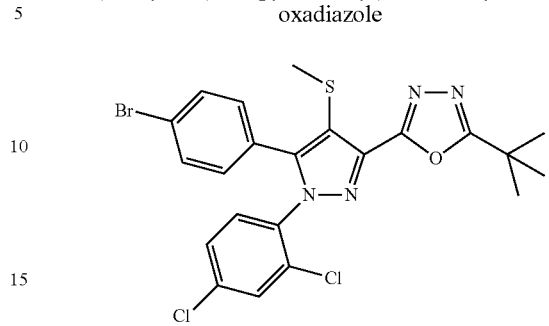

$^1$H NMR (400 MHz, CDCl$_3$) δ 7.51-7.48 (m, 2H), 7.43-7.42 (m, 1H), 7.40 (bs, 1H), 7.36-7.33 (m, 1H), 7.17-7.13 (m, 2H), 2.40 (s, 3H), 1.51 (s, 9H).
MH+537.

Example 10

2-(5-(4-bromophenyl)-1-(2,4-dichlorophenyl)-4-(methylthio)-1H-pyrazol-3-yl)-5-(1-(trifluoromethyl)cyclopropyl)-1,3,4-oxadiazole

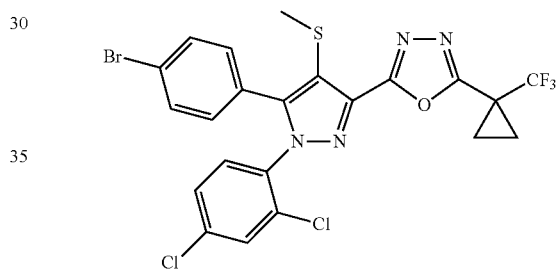

$^1$H NMR (400 MHz, CDCl$_3$) δ 7.51-7.49 (m, 2H), 7.44-7.32 (m, 3H), 7.18-7.14 (m, 2H), 2.39 (s, 3H), 1.67-1.60 (m, 4H).
MH+589.

Example 11

2-(5-(4-bromophenyl)-1-(2,4-dichlorophenyl)-4-(methylthio)-1H-pyrazol-3-yl)-5-(1-(trifluoromethyl)cyclobutyl)-1,3,4-oxadiazole

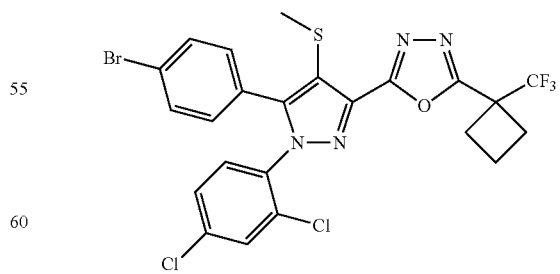

$^1$H NMR (400 MHz, CDCl$_3$) δ 7.52-7.49 (m, 2H), 7.44-7.40 (m, 2H), 7.36-7.34 (m, 1H), 7.16-7.14 (m, 2H), 2.89-2.77 (m, 4H), 2.39 (s, 3H), 2.22-2.14 (m, 2H).
MH+603.

Example 12

2-(5-(4-bromophenyl)-1-(2,4-dichlorophenyl)-4-(methylthio)-1H-pyrazol-3-yl)-5-(1-(4-chlorophenyl)cyclopropyl)-1,3,4-oxadiazole

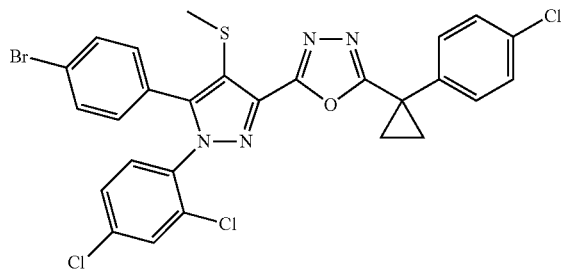

$^1$H NMR (400 MHz, CDCl$_3$) δ 7.50-7.48 (m, 2H), 7.44-7.38 (m, 3H), 7.37-7.32 (m, 4H), 7.13-7.11 (m, 2H), 2.30 (s, 3H), 1.83-1.80 (m, 2H), 1.49-1.46 (m, 2H).
MH+631.

Example 13

2-(5-(4-bromophenyl)-1-(2-chlorophenyl)-4-(methylthio)-1H-pyrazol-3-yl)-5-tert-butyl-1,3,4-oxadiazole

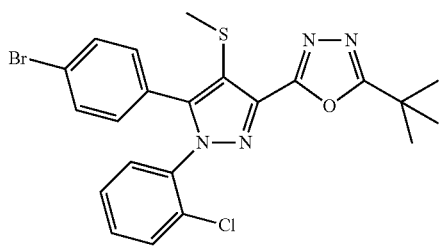

$^1$H NMR (400 MHz, CDCl$_3$) δ 7.48-7.45 (m, 3H), 7.43-7.35 (m, 3H), 7.17-7.15 (m, 2H), 2.41 (s, 3H), 1.51 (s, 9H).
MH+503.

Example 14

2-(5-(4-bromophenyl)-1-(2-chlorophenyl)-4-(methylthio)-1H-pyrazol-3-yl)-5-(1-(trifluoromethyl)cyclopropyl)-1,3,4-oxadiazole

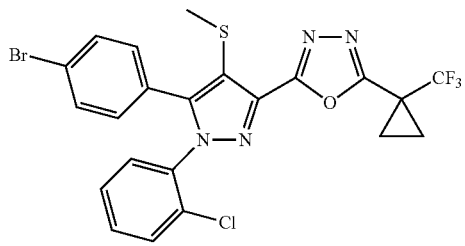

$^1$H NMR (400 MHz, CDCl$_3$) δ 7.48-7.43 (m, 3H), 7.42-7.36 (m, 3H), 7.18-7.16 (m, 2H), 2.40 (s, 3H), 1.67-1.65 (m, 4H).
MH+555.

Example 15

2-(5-(4-bromophenyl)-1-(2-chlorophenyl)-4-(methylthio)-1H-pyrazol-3-yl)-5-(1-(trifluoromethyl)cyclobutyl)-1,3,4-oxadiazole

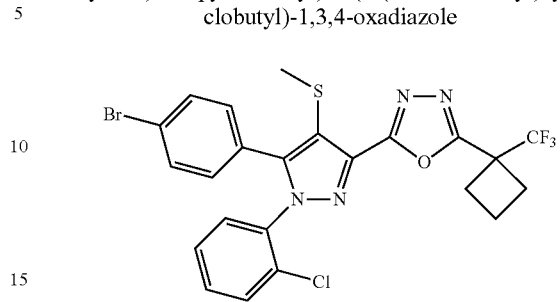

$^1$H NMR (400 MHz, CDCl$_3$) δ 7.50-7.46 (m, 3H), 7.44-7.34 (m, 3H), 7.18-7.16 (m, 2H), 2.90-2.77 (m, 4H), 2.41 (s, 3H), 2.22-2.14 (m, 2H).
MH+569.

Example 16

2-(5-(4-bromophenyl)-1-(2-chlorophenyl)-4-(methylthio)-1H-pyrazol-3-yl)-5-(1-(4-chlorophenyl)cyclopropyl)-1,3,4-oxadiazole

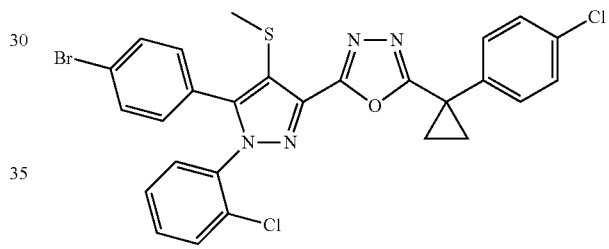

$^1$H NMR (400 MHz, CDCl$_3$) δ 7.46-7.31 (m, 10H), 7.15-7.13 (m, 2H), 2.32 (s, 3H), 1.83-1.80 (m, 2H), 1.48-1.45 (m, 2H).
MH+597.

Example 17

2-tert-butyl-5-(5-(4-chlorophenyl)-1-(2,4-dichlorophenyl)-4-(ethylthio)-1H-pyrazol-3-yl)-1,3,4-oxadiazole

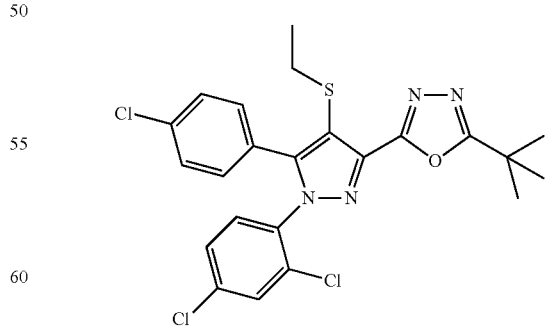

$^1$H NMR (400 MHz, CDCl$_3$) δ 7.44-7.39 (m, 2H), 7.35-7.32 (m, 3H), 7.23-7.21 (m, 2H), 2.86 (q, J=7.6 Hz, 2H), 1.51 (s, 9H), 1.09 (t, J=7.6 Hz, 3H).
MH+507.

Example 18

2-(5-(4-chlorophenyl)-1-(2,4-dichlorophenyl)-4-(ethylthio)-1H-pyrazol-3-yl)-5-(1-(trifluoromethyl)cyclopropyl)-1,3,4-oxadiazole

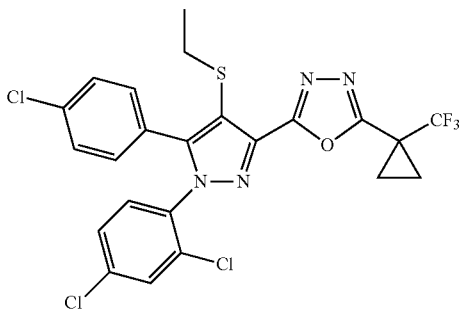

¹H NMR (400 MHz, CDCl₃) δ 7.45-7.39 (m, 2H), 7.36-7.33 (m, 3H), 7.25-7.22 (m, 2H), 2.85 (q, J=7.6 Hz, 2H), 1.68-1.65 (m, 4H), 1.09 (t, J=7.6 Hz, 3H).
MH+559.

Example 19

2-(5-(4-chlorophenyl)-1-(2,4-dichlorophenyl)-4-(ethylthio)-1H-pyrazol-3-yl)-5-(1-(trifluoromethyl)cyclobutyl)-1,3,4-oxadiazole

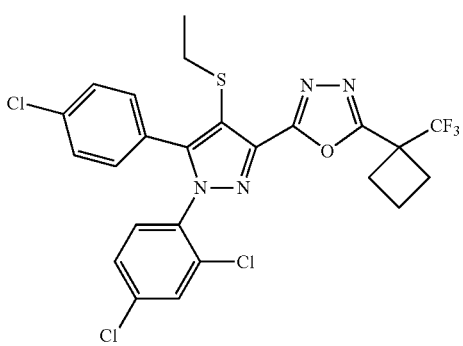

¹H NMR (400 MHz, CDCl₃) δ 7.44-7.43 (m, 1H), 7.41-7.39 (m, 1H), 7.35-7.33 (m, 3H), 7.23-7.21 (m, 2H), 2.89-2.77 (m, 6H), 2.23-2.14 (q, J=8 Hz, 2H), 1.09 (t, J=7.4 Hz, 3H).
MH+573.

Example 20

2-(5-(4-chlorophenyl)-1-(2,4-dichlorophenyl)-4-(ethylthio)-1H-pyrazol-3-yl)-5-(1-(4-chlorophenyl)cyclopropyl)-1,3,4-oxadiazole

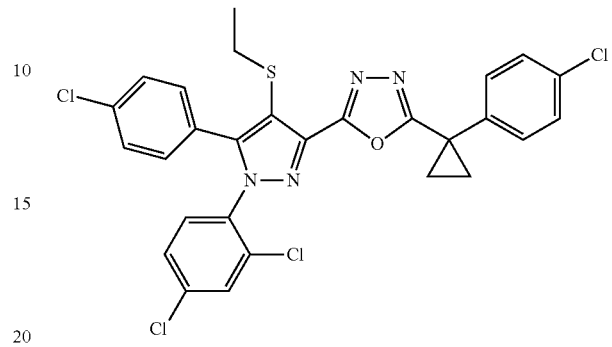

¹H NMR (400 MHz, CDCl₃) δ 7.43-7.41 (m, 3H), 7.38-7.31 (m, 6H), 7.20-7.18 (m, 2H), 2.76 (q, J=7.6 Hz, 2H), 1.83-1.80 (m, 2H), 1.49-1.46 (m, 2H), 1.02 (t, J=7.4 Hz, 3H).
MH+601.

Preparation of 1,3,4-thiadiazole (formula (Ia-2))

Example 21

2-tert-butyl-5-(5-(4-chlorophenyl)-1-(2,4-dichlorophenyl)-4-(methylthio)-1H-pyrazol-3-yl)-1,3,4-thiadiazole (Ia-2)

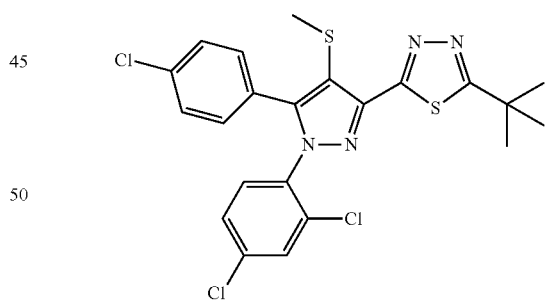

To a solution of hydrazide (9) (70 mg, 0.136 mmol) and Lawesson's reagent (137 mg, 0.339 mmol) in THF (5 mL) was irradiated in a microwave reactor (Biotage Initiator™) for 50 minutes at 155° C. The organic extract was dried over anhydrous MgSO₄, filtered, and concentrated in vacuo. The residue was subjected to silica gel column chromatography (eluent: hexane/EtOAc=4/1) to obtain 54 mg (78%) of the title compound as a solid.

¹H NMR (400 MHz, CDCl₃) δ 7.42-7.37 (m, 1H), 7.35-7.29 (m, 4H), 7.23-7.21 (m, 2H), 2.42 (s, 3H), 1.55 (s, 9H).
MH+509.

The following compounds of Examples 22 to 40 were obtained by using corresponding starting materials and repeating the procedure of Example 21.

Example 22

2-(5-(4-chlorophenyl)-1-(2,4-dichlorophenyl)-4-(methylthio)-1H-pyrazol-3-yl)-5-(1-(trifluoromethyl)cyclopropyl)-1,3,4-thiadiazole

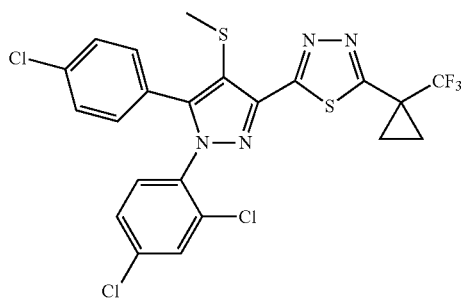

$^1$H NMR (400 MHz, CDCl$_3$) δ 7.44-7.43 (m, 1H), 7.39-7.32 (m, 4H), 7.24-7.22 (m, 2H), 2.39 (s, 3H), 1.78 (bs, 2H), 1.66-1.64 (m, 2H).
MH+561.

Example 23

2-(5-(4-chlorophenyl)-1-(2,4-dichlorophenyl)-4-(methylthio)-1H-pyrazol-3-yl)-5-(1-(trifluoromethyl)cyclobutyl)-1,3,4-thiadiazole

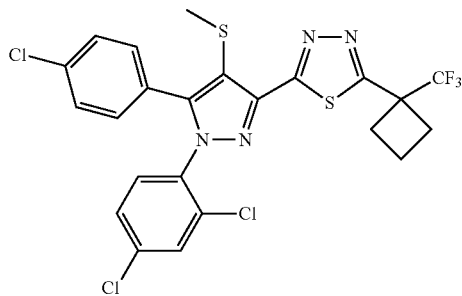

$^1$H NMR (400 MHz, CDCl$_3$) δ 7.44-7.40 (m, 1H), 7.37-7.33 (m, 4H), 7.25-7.23 (m, 2H), 2.92-2.80 (m, 4H), 2.42 (s, 3H), 2.22-2.14 (m, 2H).
MH+575.

Example 24

2-(5-(4-chlorophenyl)-1-(2,4-dichlorophenyl)-4-(methylthio)-1H-pyrazol-3-yl)-5-(1-(4-chlorophenyl)cyclopropyl)-1,3,4-thiadiazole

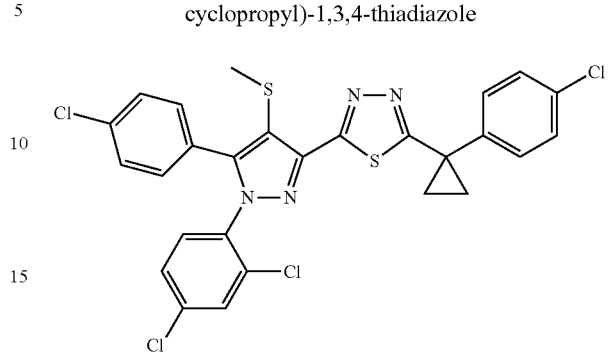

$^1$H NMR (400 MHz, CDCl$_3$) δ 7.45-7.40 (m, 3H), 7.35-7.30 (m, 6H), 7.21-7.19 (m, 2H), 2.38 (s, 3H), 1.99-1.96 (m, 2H), 1.53-1.50 (m, 2H).
MH+603.

Example 25

2-tert-butyl-5-(1-(2-chlorophenyl)-5-(4-chlorophenyl)-4-(methylthio)-1H-pyrazol-3-yl)-1,3,4-thiadiazole

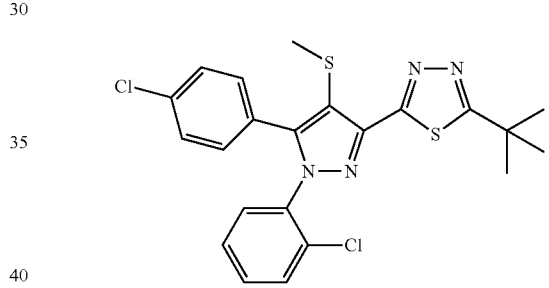

$^1$H NMR (400 MHz, CDCl$_3$) δ 7.44-7.30 (m, 6H), 7.27-7.24 (m, 2H), 2.45 (s, 3H), 1.55 (s, 9H).
MH+475.

Example 26

2-(1-(2-chlorophenyl)-5-(4-chlorophenyl)-4-(methylthio)-1H-pyrazol-3-yl)-5-(1-(trifluoromethyl)cyclopropyl)-1,3,4-thiadiazole

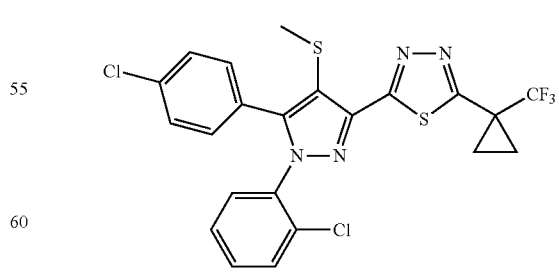

$^1$H NMR (400 MHz, CDCl$_3$) δ 7.45-7.41 (m, 2H), 7.39-7.35 (m, 1H), 7.32-7.30 (m, 2H), 7.26-7.24 (m, 3H), 2.40 (s, 3H), 1.78 (m, 2H), 1.65-1.62 (m, 2H).
MH+527.

Example 27

2-(1-(2-chlorophenyl)-5-(4-chlorophenyl)-4-(methylthio)-1H-pyrazol-3-yl)-5-(1-(trifluoromethyl)cyclobutyl)-1,3,4-thiadiazole

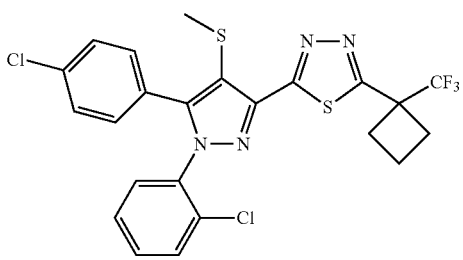

$^1$H NMR (400 MHz, CDCl$_3$) δ 7.45-7.40 (m, 2H), 7.39-7.35 (m, 2H), 7.33-7.31 (m, 2H), 7.26-7.24 (m, 2H), 2.92-2.80 (m, 4H), 2.43 (s, 3H), 2.24-2.14 (q, J=8 Hz, 2H).
MH+541.

Example 28

2-(1-(2-chlorophenyl)-5-(4-chlorophenyl)-4-(methylthio)-1H-pyrazol-3-yl)-5-(1-(4-chlorophenyl)cyclopropyl)-1,3,4-thiadiazole

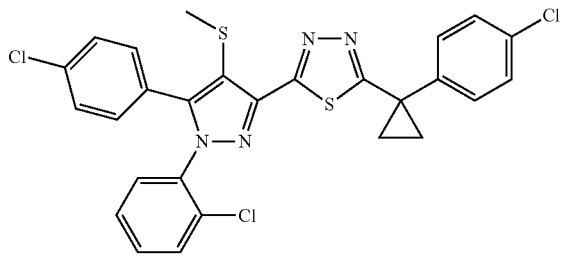

$^1$H NMR (400 MHz, CDCl$_3$) δ 7.45-7.42 (m, 2H), 7.40-7.34 (m, 5H), 7.33-7.27 (m, 3H), 7.23-7.20 (m, 2H), 2.40 (s, 3H), 1.99-1.96 (m, 2H), 1.53-1.50 (m, 2H).
MH+569.

Example 29

2-(5-(4-bromophenyl)-1-(2,4-dichlorophenyl)-4-(methylthio)-1H-pyrazol-3-yl)-5-tert-butyl-1,3,4-thiadiazole

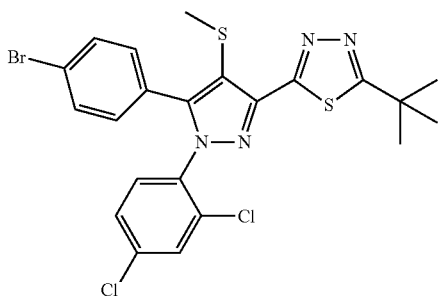

$^1$H NMR (400 MHz, CDCl$_3$) δ 7.52-7.48 (m, 2H), 7.45-7.44 (m, 1H), 7.39-7.32 (m, 2H), 7.19-7.15 (m, 2H), 2.44 (s, 3H), 1.55 (s, 9H).
MH+553.

Example 30

2-(5-(4-bromophenyl)-1-(2,4-dichlorophenyl)-4-(methylthio)-1H-pyrazol-3-yl)-5-(1-(trifluoromethyl)cyclopropyl)-1,3,4-thiadiazole

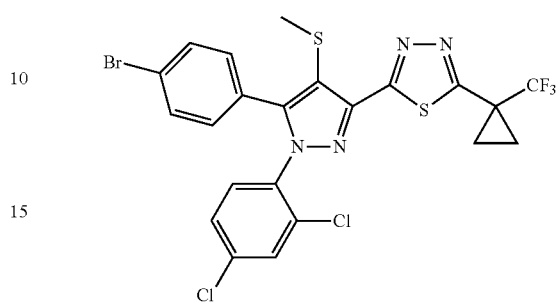

$^1$H NMR (400 MHz, CDCl$_3$) δ 7.51-7.49 (m, 2H), 7.44-7.43 (m, 1H), 7.39-7.32 (m, 2H), 7.18-7.16 (m, 2H), 2.38 (s, 3H), 1.80-1.78 (m, 2H), 1.66-1.64 (m, 2H).
MH+605.

Example 31

2-(5-(4-bromophenyl)-1-(2,4-dichlorophenyl)-4-(methylthio)-1H-pyrazol-3-yl)-5-(1-(trifluoromethyl)cyclobutyl)-1,3,4-thiadiazole

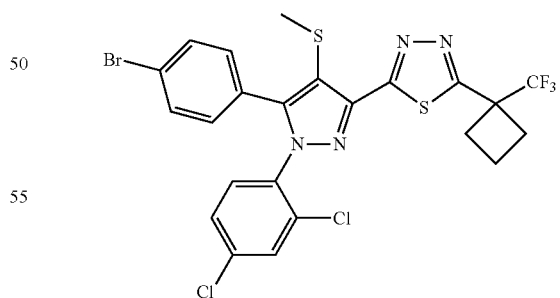

$^1$H NMR (400 MHz, CDCl$_3$) δ 7.52-7.50 (m, 2H), 7.45-7.44 (m, 1H), 7.39-7.32 (m, 2H), 7.19-7.16 (m, 2H), 2.88-2.83 (m, 4H), 2.42 (s, 3H), 2.20-2.16 (m, 2H).
H+619.

Example 32

2-(5-(4-bromophenyl)-1-(2,4-dichlorophenyl)-4-(methylthio)-1H-pyrazol-3-yl)-5-(1-(4-chlorophenyl)cyclopropyl)-1,3,4-thiadiazole

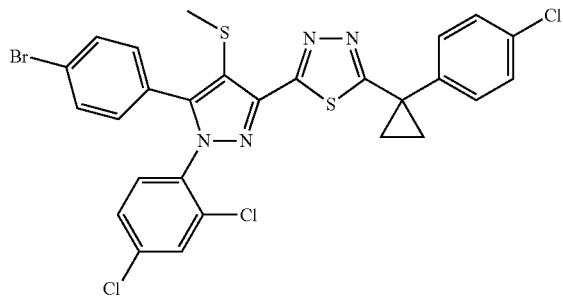

¹H NMR (400 MHz, CDCl₃) δ 7.49-7.40 (m, 5H), 7.35-7.30 (m, 4H), 7.14-7.12 (m, 2H), 2.38 (s, 3H), 1.98-1.97 (m, 2H), 1.52-1.51 (m, 2H).
MH+647.

Example 33

2-(5-(4-bromophenyl)-1-(2-chlorophenyl)-4-(methylthio)-1H-pyrazol-3-yl)-5-tert-butyl-1,3,4-thiadiazole

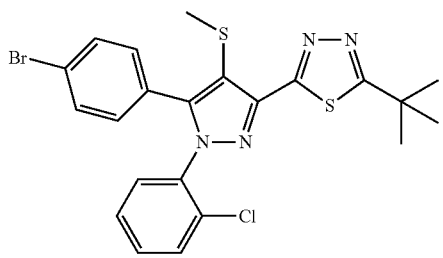

¹H NMR (400 MHz, CDCl₃) δ 7.52-7.32 (m, 6H), 7.19-7.17 (m, 2H), 2.44 (s, 3H), 1.55 (s, 9H).
MH+519.

Example 34

2-(5-(4-bromophenyl)-1-(2-chlorophenyl)-4-(methylthio)-1H-pyrazol-3-yl)-5-(1-(trifluoromethyl)cyclopropyl)-1,3,4-thiadiazole

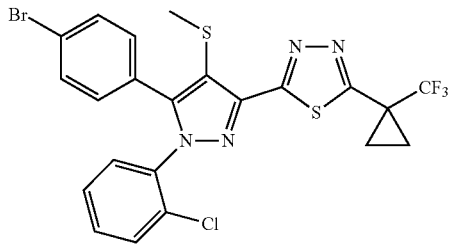

¹H NMR (400 MHz, CDCl₃) δ 7.48-7.35 (m, 6H), 7.19-7.17 (m, 2H), 2.39 (s, 3H), 1.78 (bs, 2H), 1.64-1.63 (m, 2H).
MH+571.

Example 35

2-(5-(4-bromophenyl)-1-(2-chlorophenyl)-4-(methylthio)-1H-pyrazol-3-yl)-5-(1-(trifluoromethyl)cyclobutyl)-1,3,4-thiadiazole

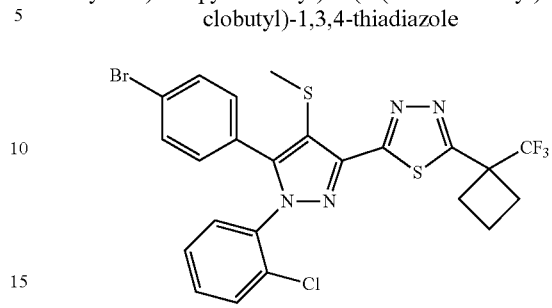

¹H NMR (400 MHz, CDCl₃) δ 7.48-7.33 (m, 6H), 7.20-7.17 (m, 2H), 2.88-2.82 (m, 4H), 2.43 (s, 3H), 2.20-2.16 (m, 2H).
MH+585.

Example 36

2-(5-(4-bromophenyl)-1-(2-chlorophenyl)-4-(methylthio)-1H-pyrazol-3-yl)-5-(1-(4-chlorophenyl)cyclopropyl)-1,3,4-thiadiazole

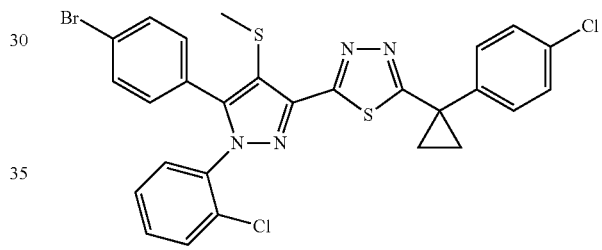

¹H NMR (400 MHz, CDCl₃) δ 7.49-7.46 (m, 4H), 7.43-7.29 (m, 6H), 7.19-7.17 (m, 2H), 2.43 (s, 3H), 2.02-1.99 (m, 2H), 1.55-1.53 (m, 2H).
MH+613.

Example 37

2-tert-butyl-5-(5-(4-chlorophenyl)-1-(2,4-dichlorophenyl)-4-(ethylthio)-1H-pyrazol-3-yl)-1,3,4-thiadiazole

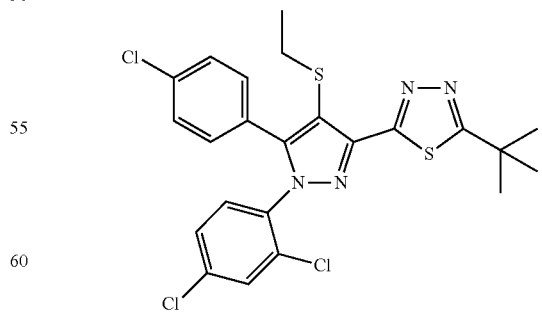

¹H NMR (400 MHz, CDCl₃) δ 7.44-7.43 (m, 1H), 7.38-7.36 (m, 1H), 7.34-7.31 (m, 3H), 7.25-7.21 (m, 2H), 2.91 (q, J=7.2 Hz, 2H), 1.55 (s, 9H), 1.08 (t, J=7.2 Hz, 3H).
MH+523.

Example 38

2-(5-(4-chlorophenyl)-1-(2,4-dichlorophenyl)-4-(ethylthio)-1H-pyrazol-3-yl)-5-(1-(trifluoromethyl)cyclopropyl)-1,3,4-thiadiazole

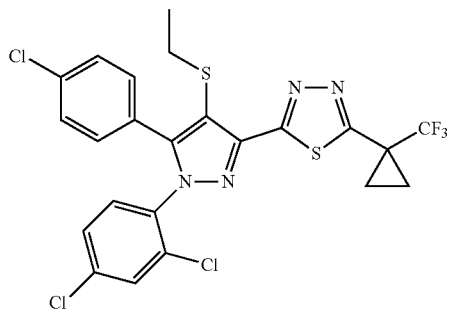

$^1$H NMR (400 MHz, CDCl$_3$) δ 7.45-7.44 (m, 1H), 7.40-7.33 (m, 4H), 7.27-7.23 (m, 2H), 2.84 (q, J=7.2 Hz, 2H), 1.78 (bs, 2H), 1.66-1.63 (m, 2H), 1.08 (t, J=7.2 Hz, 3H).
MH+575.

Example 40

2-(5-(4-chlorophenyl)-1-(2,4-dichlorophenyl)-4-(ethylthio)-1H-pyrazol-3-yl)-5-(1-(4-chlorophenyl)cyclopropyl)-1,3,4-thiadiazole

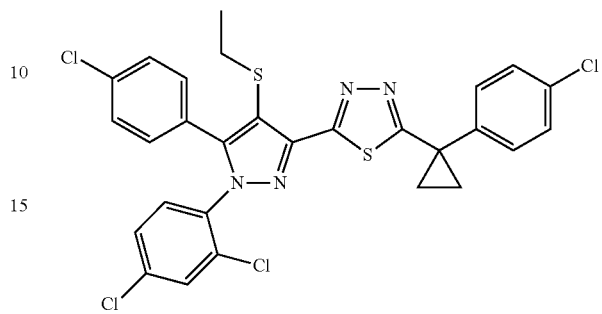

$^1$H NMR (400 MHz, CDCl$_3$) δ 7.45-7.40 (m, 3H), 7.35-7.30 (m, 5H), 7.28-7.26 (m, 1H), 7.23-7.18 (m, 2H), 2.84 (q, J=7.6 Hz, 2H), 1.99-1.96 (m, 2H), 1.53-1.50 (m, 2H), 1.05 (t, J=7.4 Hz, 3H).
MH+617.

Preparation of Sulfoxide Compound (Formula (Ib-1 and Ib-2))

Example 41

2-tert-butyl-5-(5-(4-chlorophenyl)-1-(2,4-dichlorophenyl)-4-(methylsulfinyl)-1H-pyrazol-3-yl)-1,3,4-oxadiazole (Ib-1)

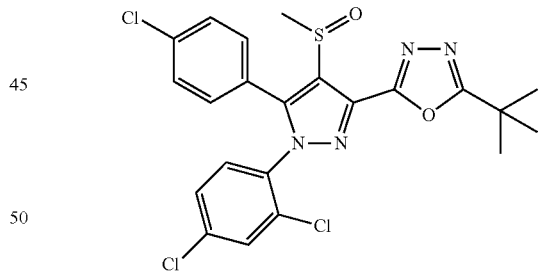

Example 39

2-(5-(4-chlorophenyl)-1-(2,4-dichlorophenyl)-4-(ethylthio)-1H-pyrazol-3-yl)-5-(1-(trifluoromethyl)cyclobutyl)-1,3,4-thiadiazole

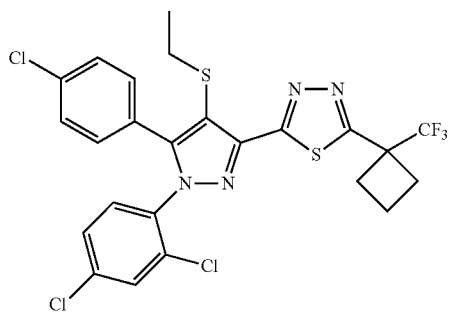

$^1$H NMR (400 MHz, CDCl$_3$) δ 7.45 (m, 1H), 7.40 (m, 1H), 7.35-7.32 (m, 3H), 7.25-7.23 (m, 2H), 2.91-2.80 (m, 6H), 2.18 (q, J=8 Hz, 2H), 1.09 (t, J=7.4 Hz, 3H).
MH+589.

To a solution of 2-tert-Butyl-5-(5-(4-chlorophenyl)-1-(2,4-dichlorophenyl)-4-(methylthio)-1H-pyrazol-3-yl)-1,3,4-oxadiazole (Ia-1) (150 mg, 0.30 mmol) in CH$_2$Cl$_2$ (5 mL) was added m-CPBA (77% Max, 74 mg, 0.33 mmol). The reaction mixture was stirred for 1 hr at room temperature. Saturated NaHCO$_3$ was added to the reaction mixture, and the organic extract was dried over anhydrous MgSO$_4$, filtered and concentrated in vacuo. The residue was subjected to silica gel column chromatography (eluent: hexane/EtOAc=½) to obtain 100 mg (65%) of the title compound as a white solid.

$^1$H NMR (400 MHz, CDCl$_3$) δ 7.46 (bs, 1H), 7.34-7.29 (m, 6H), 3.15 (s, 3H), 1.51 (s, 9H).
MH+509.

The following compounds of Examples 42 to 59 were obtained by using corresponding starting materials and repeating the procedure of Example 41.

Example 42

2-(5-(4-chlorophenyl)-1-(2,4-dichlorophenyl)-4-(methylsulfinyl)-1H-pyrazol-3-yl)-5-(1-(trifluoromethyl)cyclopropyl)-1,3,4-oxadiazole

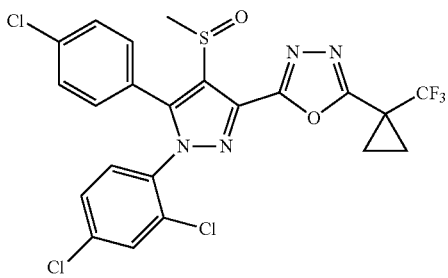

$^1$H NMR (400 MHz, CDCl$_3$). 7.46 (m, 1H), 7.34-7.32 (m, 4H), 7.28-7.26 (m, 2H), 3.13 (s, 3H), 1.66 (m, 4H).
MH+561.

Example 43

2-(5-(4-chlorophenyl)-1-(2,4-dichlorophenyl)-4-(methylsulfinyl)-1H-pyrazol-3-yl)-5-(1-(trifluoromethyl)cyclobutyl)-1,3,4-oxadiazole

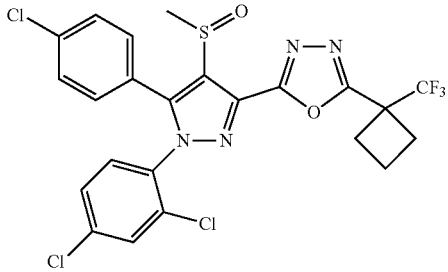

$^1$H NMR (400 MHz, CDCl$_3$) δ 7.46 (m, 1H), 7.35-7.33 (m, 4H), 7.28-7.26 (m, 2H), 3.15 (s, 3H), 2.86-2.80 (m, 4H), 2.21-2.16 (m, 2H).
MH+575.

Example 44

2-(5-(4-chlorophenyl)-1-(2,4-dichlorophenyl)-4-(methylsulfinyl)-1H-pyrazol-3-yl)-5-(1-(4-chlorophenyl)cyclopropyl)-1,3,4-oxadiazole

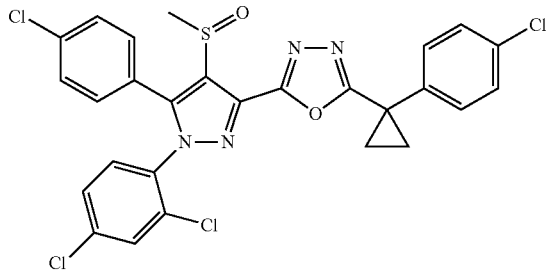

$^1$H NMR (400 MHz, CDCl$_3$) δ 7.44-7.41 (m, 3H), 7.34-7.30 (m, 5H), 7.26-7.23 (m, 3H), 3.07 (s, 3H), 1.83-1.80 (m, 2H), 1.49 (m, 2H).
MH+603.

Example 45

2-tert-butyl-5-(1-(2-chlorophenyl)-5-(4-chlorophenyl)-4-(methylsulfinyl)-1H-pyrazol-3-yl)-1,3,4-oxadiazole

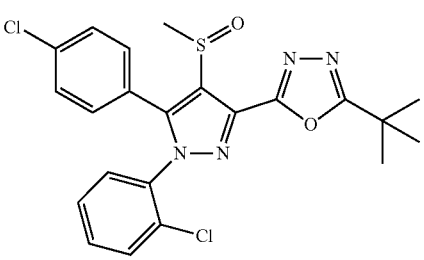

$^1$H NMR (400 MHz, CDCl$_3$) δ 7.45-7.33 (m, 4H), 7.29-7.27 (m, 4H), 3.15 (s, 3H), 1.51 (s, 9H).
MH+475.

Example 46

2-(1-(2-chlorophenyl)-5-(4-chlorophenyl)-4-(methylsulfinyl)-1H-pyrazol-3-yl)-5-(1-(trifluoromethyl)cyclopropyl)-1,3,4-oxadiazole

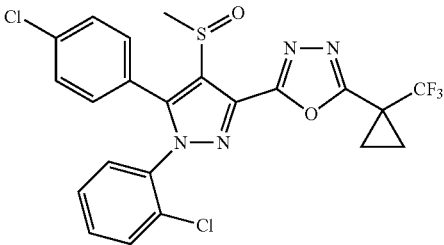

$^1$H NMR (400 MHz, CDCl$_3$) δ 7.44-7.34 (m, 4H), 7.32-7.30 (m, 4H), 3.15 (s, 3H), 1.67-1.63 (m, 4H).
MH+527.

Example 47

2-(1-(2-chlorophenyl)-5-(4-chlorophenyl)-4-(methylsulfinyl)-1H-pyrazol-3-yl)-5-(1-(trifluoromethyl)cyclobutyl)-1,3,4-oxadiazole

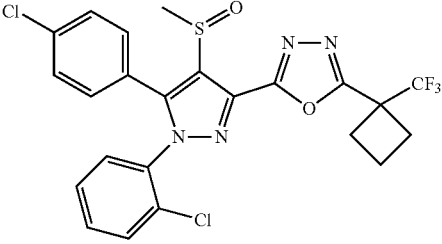

$^1$H NMR (400 MHz, CDCl$_3$) δ 7.45-7.34 (m, 4H), 7.32-7.27 (m, 4H), 3.16 (s, 3H), 2.89-2.76 (m, 4H), 2.24-2.14 (q, J=8 Hz, 2H).
MH+541.

Example 48

2-(1-(2-chlorophenyl)-5-(4-chlorophenyl)-4-(methyl-sulfinyl)-1H-pyrazol-3-yl)-5-(1-(4-chlorophenyl)cyclopropyl)-1,3,4-oxadiazole

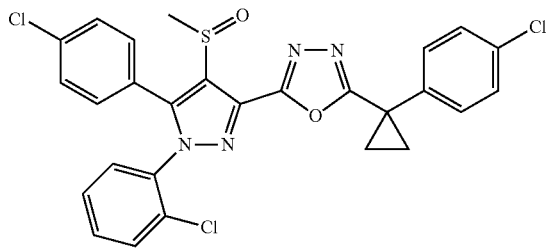

$^1$H NMR (400 MHz, CDCl$_3$) δ 7.43-7.40 (m, 4H), 7.38-7.29 (m, 4H), 7.27-7.24 (m, 4H), 3.08 (s, 3H), 1.83-1.80 (m, 2H), 1.50-1.47 (m, 2H).
MH+569.

Example 49

2-(5-(4-bromophenyl)-1-(2,4-dichlorophenyl)-4-(methylsulfinyl)-1H-pyrazol-3-yl)-5-tert-butyl-1,3,4-oxadiazole

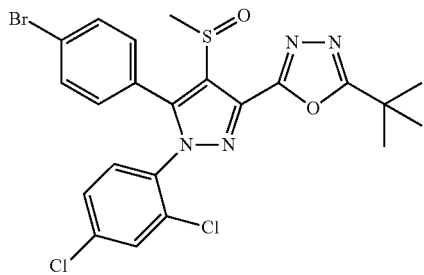

$^1$H NMR (400 MHz, CDCl$_3$) δ 7.50-7.45 (m, 3H), 7.34 (bs, 2H), 7.22-7.19 (m, 2H), 3.14 (s, 3H), 1.51 (s, 9H).
MH+553.

Example 50

2-(5-(4-bromophenyl)-1-(2,4-dichlorophenyl)-4-(methylsulfinyl)-1H-pyrazol-3-yl)-5-(1-(trifluoromethyl)cyclopropyl)-1,3,4-oxadiazole

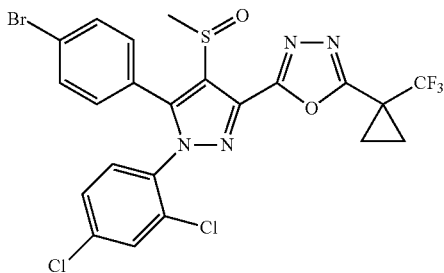

$^1$H NMR (400 MHz, CDCl$_3$) δ 7.50-7.46 (m, 3H), 7.35 (bs, 2H), 7.21-7.19 (m, 2H), 3.14 (s, 3H), 1.66 (bs, 4H).
MH+605.

Example 51

2-(5-(4-bromophenyl)-1-(2,4-dichlorophenyl)-4-(methylsulfinyl)-1H-pyrazol-3-yl)-5-(1-(trifluoromethyl)cyclobutyl)-1,3,4-oxadiazole

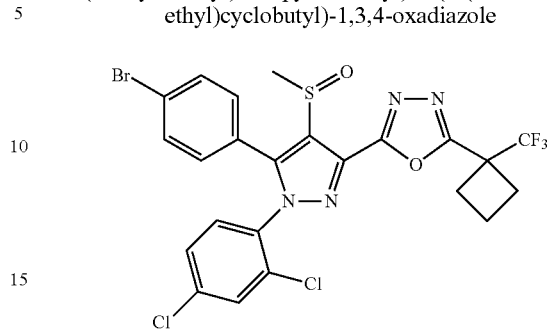

$^1$H NMR (400 MHz, CDCl$_3$) δ 7.50-7.45 (m, 3H), 7.35 (bs, 2H), 7.21-7.19 (m, 2H), 3.15 (s, 3H), 2.86-2.77 (m, 4H), 2.23-2.14 (m, 2H).
MH+619.

Example 52

2-(5-(4-bromophenyl)-1-(2,4-dichlorophenyl)-4-(methylsulfinyl)-1H-pyrazol-3-yl)-5-(1-(4-chlorophenyl)cyclopropyl)-1,3,4-oxadiazole

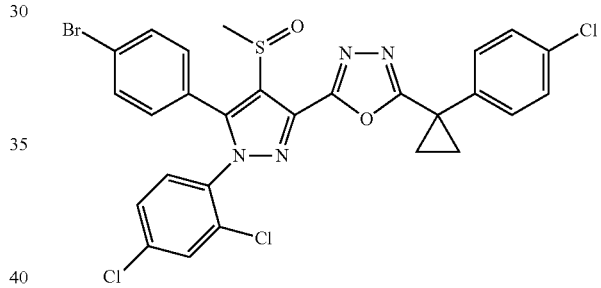

$^1$H NMR (400 MHz, CDCl$_3$) δ 7.49-7.41 (m, 5H), 7.35-7.32 (m, 4H), 7.18-7.16 (m, 2H), 3.07 (s, 3H), 1.83-1.80 (m, 2H), 1.51-1.48 (m, 2H).
MH+647.

Example 53

2-(5-(4-bromophenyl)-1-(2-chlorophenyl)-4-(methylsulfinyl)-1H-pyrazol-3-yl)-5-tert-butyl-1,3,4-oxadiazole

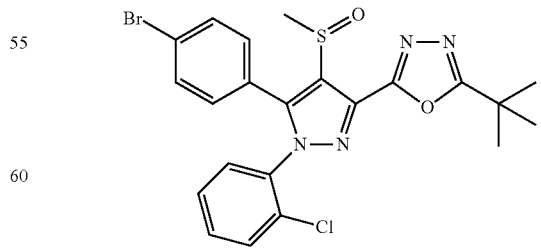

$^1$H NMR (400 MHz, CDCl$_3$) δ 7.46-7.34 (m, 6H), 7.23-7.21 (m, 2H), 3.15 (s, 3H), 1.51 (s, 9H).
MH+519.

Example 54

2-(5-(4-bromophenyl)-1-(2-chlorophenyl)-4-(methylsulfinyl)-1H-pyrazol-3-yl)-5-(1-(trifluoromethyl)cyclopropyl)-1,3,4-oxadiazole

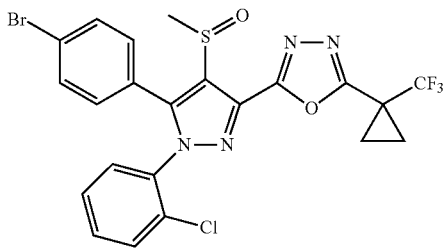

$^1$H NMR (400 MHz, CDCl$_3$) δ 7.47-7.34 (m, 6H), 7.23-7.20 (m, 2H), 3.15 (s, 3H), 1.67-1.65 (m, 4H).
MH+571.

Example 55

2-(5-(4-bromophenyl)-1-(2-chlorophenyl)-4-(methylsulfinyl)-1H-pyrazol-3-yl)-5-(1-(trifluoromethyl)cyclobutyl)-1,3,4-oxadiazole

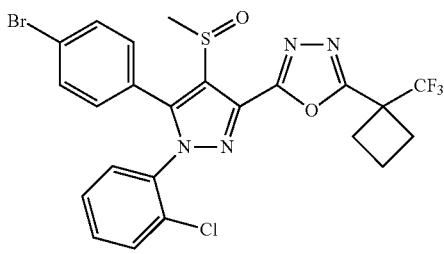

$^1$H NMR (400 MHz, CDCl$_3$) δ 7.47-7.34 (m, 6H), 7.23-7.21 (m, 2H), 3.16 (s, 3H), 2.89-2.76 (m, 4H), 2.25-2.14 (m, 2H).
MH+585.

Example 56

2-tert-butyl-5-(5-(4-chlorophenyl)-1-(2,4-dichlorophenyl)-4-(ethylsulfinyl)-1H-pyrazol-3-yl)-1,3,4-oxadiazole

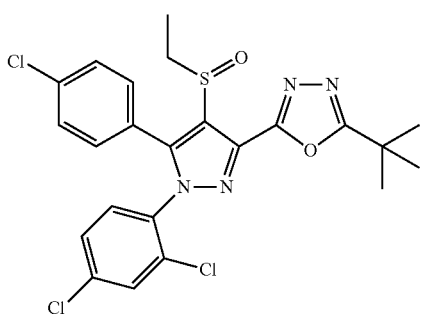

$^1$H NMR (400 MHz, CDCl$_3$) δ 7.45 (bs, 1H), 7.32-7.27 (m, 6H), 3.42-3.34 (m, 2H), 1.32-1.28 (m, 3H).
MH+523.

Example 57

2-(5-(4-chlorophenyl)-1-(2,4-dichlorophenyl)-4-(ethylsulfinyl)-1H-pyrazol-3-yl)-5-(1-(trifluoromethyl)cyclopropyl)-1,3,4-oxadiazole

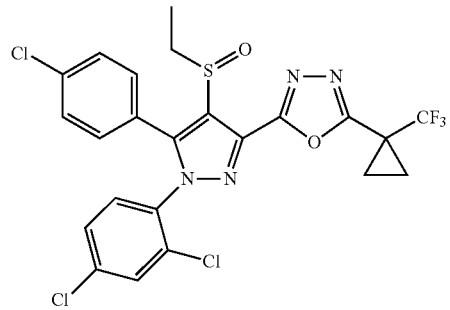

$^1$H NMR (400 MHz, CDCl$_3$) δ 7.46 (bs, 1H), 7.33-7.27 (m, 6H), 3.44-3.27 (m, 2H), 1.67-1.65 (m, 4H), 1.31-1.27 (m, 3H).
MH+575.

Example 58

2-(5-(4-chlorophenyl)-1-(2,4-dichlorophenyl)-4-(ethylsulfinyl)-1H-pyrazol-3-yl)-5-(1-(trifluoromethyl)cyclobutyl)-1,3,4-oxadiazole

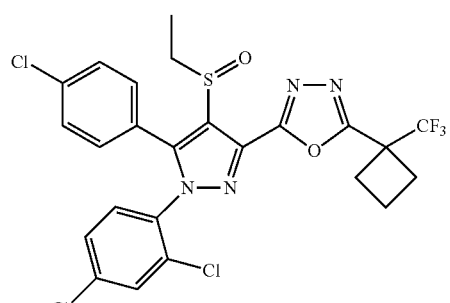

$^1$H NMR (400 MHz, CDCl$_3$) δ 7.46 (m, 1H), 7.33-7.31 (m, 3H), 7.29-7.26 (m, 3H), 3.47-3.29 (m, 2H), 2.85-2.76 (m, 4H), 2.18 (q, J=8 Hz, 2H), 1.30 (t, J=7.4 Hz, 3H).
MH+589.

Example 59

2-(5-(4-chlorophenyl)-1-(2,4-dichlorophenyl)-4-(ethylsulfinyl)-1H-pyrazol-3-yl)-5-(1-(4-chlorophenyl)cyclopropyl)-1,3,4-oxadiazole

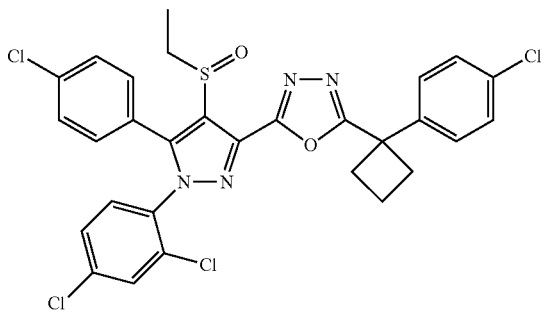

$^1$H NMR (400 MHz, CDCl$_3$) δ 7.44-7.41 (m, 3H), 7.34-7.21 (m, 8H), 3.37-3.23 (m, 2H), 1.82-1.80 (m, 2H), 1.50-1.47 (m, 2H), 1.24 (t, J=7.4 Hz, 3H).
MH+617.

Example 60

2-tert-butyl-5-(5-(4-chlorophenyl)-1-(2,4-dichlorophenyl)-4-(methylsulfinyl)-1H-pyrazol-3-yl)-1,3,4-thiadiazole (Ib-2)

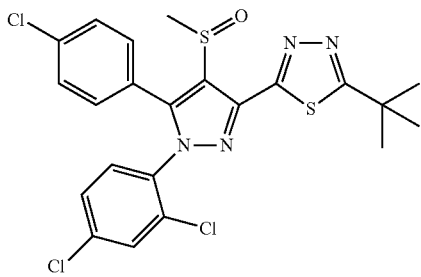

To a solution of 2-tert-Butyl-5-(5-(4-chlorophenyl)-1-(2,4-dichlorophenyl)-4-(methylthio)-1H-pyrazol-3-yl)-1,3,4-thiadiazole (Ia-2) (190 mg, 0.37 mmol) in CH$_2$Cl$_2$ (10 mL) was added m-CPBA (77% Max, 91 mg, 0.41 mmol). The reaction mixture was stirred for 1 hr at room temperature. Saturated NaHCO$_3$ was added to the reaction mixture, then the organic extract was dried over anhydrous MgSO$_4$, filtered, and concentrated in vacuo. The residue was subjected to silica gel column chromatography (eluent: hexane/EtOAc=1/2) to obtain 148 mg (76%) of the title compound as a white solid.

$^1$H NMR (400 MHz, CDCl$_3$) δ 7.46-7.45 (m, 1H), 7.34-7.27 (m, 6H), 3.20 (s, 3H), 1.54 (s, 9H).
MH+525.

The following compounds of Examples 61 to 79 were obtained by using corresponding starting materials and repeating the procedure of Example 60.

Example 61

2-(5-(4-chlorophenyl)-1-(2,4-dichlorophenyl)-4-(methylsulfinyl)-1H-pyrazol-3-yl)-5-(1-(trifluoromethyl)cyclopropyl)-1,3,4-thiadiazole

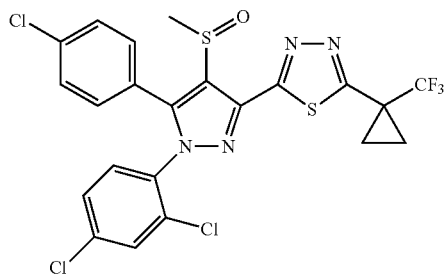

$^1$H NMR (400 MHz, CDCl$_3$) δ 7.47-7.46 (m, 1H), 7.34-7.29 (m, 6H), 3.17 (s, 3H), 1.78 (m, 2H), 1.68-1.65 (m, 2H).
MH+577.

Example 62

2-(5-(4-chlorophenyl)-1-(2,4-dichlorophenyl)-4-(methylsulfinyl)-1H-pyrazol-3-yl)-5-(1-(trifluoromethyl)cyclobutyl)-1,3,4-thiadiazole

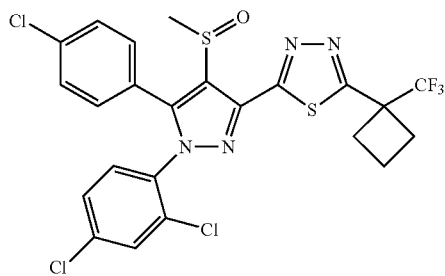

$^1$H NMR (400 MHz, CDCl$_3$) δ 7.47-7.46 (m, 1H), 7.34-7.30 (m, 5H), 7.29-7.26 (m, 1H), 3.21 (s, 3H), 2.87-2.83 (m, 4H), 2.23-2.15 (m, 2H).
MH+591.

Example 63

2-(5-(4-chlorophenyl)-1-(2,4-dichlorophenyl)-4-(methylsulfinyl)-1H-pyrazol-3-yl)-5-(1-(4-chlorophenyl)cyclopropyl)-1,3,4-thiadiazole

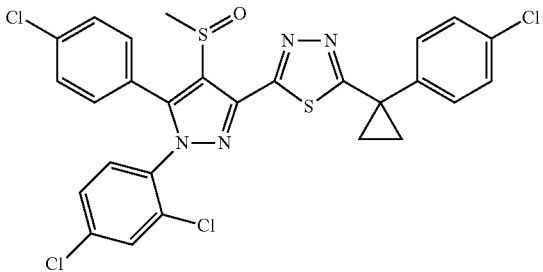

$^1$H NMR (400 MHz, CDCl$_3$) δ 7.44-7.42 (m, 3H), 7.36-7.33 (m, 2H), 7.30-7.21 (m, 6H), 3.16 (s, 3H), 1.98-1.96 (m, 2H), 1.55-1.52 (m, 2H).
MH+619.

Example 64

2-tert-butyl-5-(1-(2-chlorophenyl)-5-(4-chlorophenyl)-4-(methylsulfinyl)-1H-pyrazol-3-yl)-1,3,4-thiadiazole

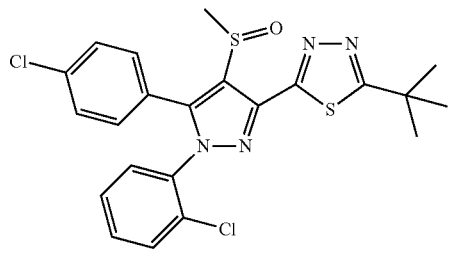

$^1$H NMR (400 MHz, CDCl$_3$) δ 7.45-7.43 (m, 1H), 7.41-7.34 (m, 2H), 7.33-7.31 (m, 1H), 7.30-7.27 (m, 3H), 7.26 (m, 1H), 3.20 (s, 3H), 1.54 (s, 9H).
MH+491.

Example 65

2-(1-(2-chlorophenyl)-5-(4-chlorophenyl)-4-(methylsulfinyl)-1H-pyrazol-3-yl)-5-(1-(trifluoromethyl)cyclopropyl)-1,3,4-thiadiazole

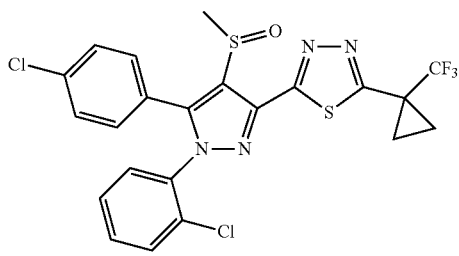

$^1$H NMR (400 MHz, CDCl$_3$) δ 7.45-7.44 (m, 2H), 7.36 (m, 2H), 7.30 (m, 4H), 3.19 (s, 3H), 1.78 (m, 2H), 1.67-1.66 (m, 2H).
MH+543.

Example 66

2-(1-(2-chlorophenyl)-5-(4-chlorophenyl)-4-(methylsulfinyl)-1H-pyrazol-3-yl)-5-(1-(trifluoromethyl)cyclobutyl)-1,3,4-thiadiazole

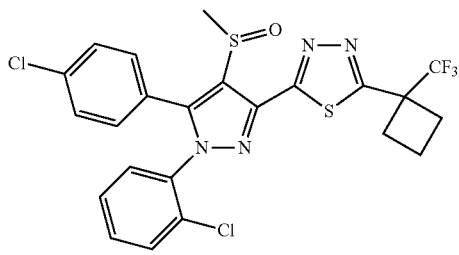

$^1$H NMR (400 MHz, CDCl$_3$) δ 7.46-7.37 (m, 2H), 7.36-7.31 (m, 2H), 7.30-7.27 (m, 4H), 3.22 (s, 3H), 2.87-2.82 (m, 4H), 2.24-2.15 (q, J=8 Hz, 2H).
MH+557.

Example 67

2-(1-(2-chlorophenyl)-5-(4-chlorophenyl)-4-(methylsulfinyl)-1H-pyrazol-3-yl)-5-(1-(4-chlorophenyl)cyclopropyl)-1,3,4-thiadiazole

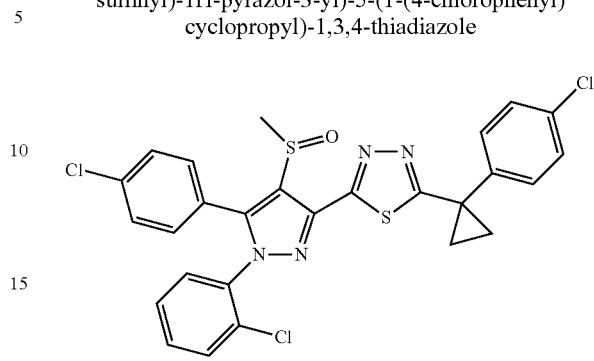

$^1$H NMR (400 MHz, CDCl$_3$) δ 7.44-7.41 (m, 2H), 7.39-7.32 (m, 4H), 7.30-7.28 (m, 2H), 7.26-7.24 (m, 4H), 3.17 (s, 3H), 2.00-1.96 (m, 2H), 1.55-1.52 (m, 2H).
MH+585.

Example 68

2-(5-(4-bromophenyl)-1-(2,4-dichlorophenyl)-4-(methylsulfinyl)-1H-pyrazol-3-yl)-5-tert-butyl-1,3,4-thiadiazole

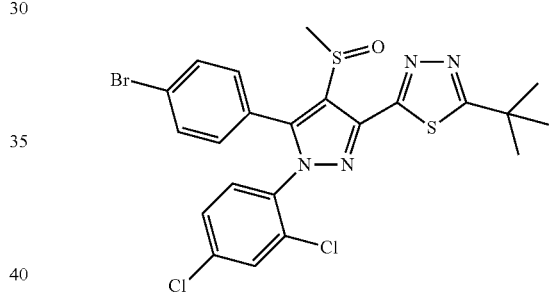

$^1$H NMR (400 MHz, CDCl$_3$) δ 7.47-7.45 (m, 3H), 7.33-7.27 (m, 2H), 7.22-7.20 (m, 2H), 3.19 (s, 3H), 1.54 (s, 9H).
MH+569.

Example 69

2-(5-(4-bromophenyl)-1-(2,4-dichlorophenyl)-4-(methylsulfinyl)-1H-pyrazol-3-yl)-5-(1-(trifluoromethyl)cyclopropyl)-1,3,4-thiadiazole

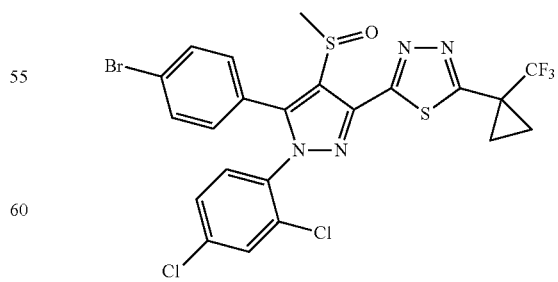

$^1$H NMR (400 MHz, CDCl$_3$) δ 7.48-7.45 (m, 3H), 7.34-7.28 (m, 2H), 7.22-7.20 (m, 2H), 3.18 (s, 3H), 1.78 (bs, 2H), 1.69-1.65 (m, 2H).
MH+621.

Example 70

2-(5-(4-bromophenyl)-1-(2,4-dichlorophenyl)-4-(methylsulfinyl)-1H-pyrazol-3-yl)-5-(1-(trifluoromethyl)cyclobutyl)-1,3,4-thiadiazole

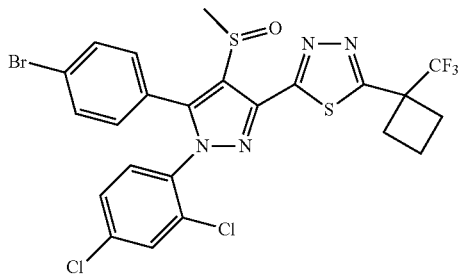

$^1$H NMR (400 MHz, CDCl$_3$) δ 7.50-7.47 (m, 3H), 7.35-7.29 (m, 2H), 7.24-7.21 (m, 2H), 3.22 (s, 3H), 2.88-2.84 (m, 4H), 2.24-2.15 (m, 2H).
MH+635.

Example 71

2-(5-(4-bromophenyl)-1-(2,4-dichlorophenyl)-4-(methylsulfinyl)-1H-pyrazol-3-yl)-5-(1-(4-chlorophenyl)cyclopropyl)-1,3,4-thiadiazole

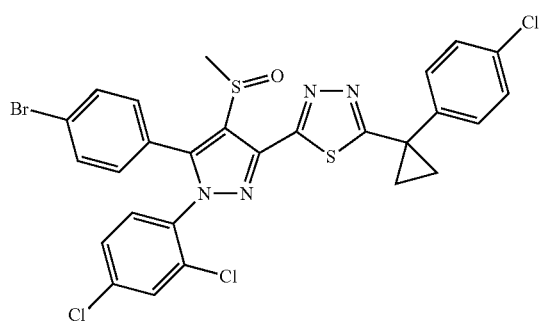

$^1$H NMR (400 MHz, CDCl$_3$) δ 7.46-7.42 (m, 5H), 7.36-7.34 (m, 2H), 7.30-7.22 (m, 2H), 7.19-7.17 (m, 2H), 3.16 (s, 3H), 1.99-1.96 (m, 2H), 1.56-1.53 (m, 2H).
MH+663.

Example 72

2-(5-(4-bromophenyl)-1-(2-chlorophenyl)-4-(methylsulfinyl)-1H-pyrazol-3-yl)-5-tert-butyl-1,3,4-thiadiazole

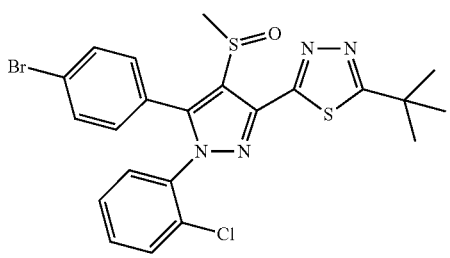

$^1$H NMR (400 MHz, CDCl$_3$) δ 7.46-7.31 (m, 6H), 7.25-7.22 (m, 2H), 3.21 (s, 3H), 1.54 (s, 9H).
MH+535.

Example 73

2-(5-(4-bromophenyl)-1-(2-chlorophenyl)-4-(methylsulfinyl)-1H-pyrazol-3-yl)-5-(1-(trifluoromethyl)cyclopropyl)-1,3,4-thiadiazole

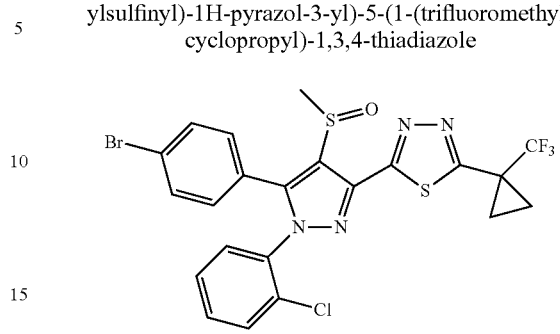

$^1$H NMR (400 MHz, CDCl$_3$) δ 7.46-7.32 (m, 6H), 7.24-7.21 (m, 2H), 3.19 (s, 3H), 1.78 (bs, 2H), 1.68-1.64 (m, 2H).
MH+587.

Example 74

2-(5-(4-bromophenyl)-1-(2-chlorophenyl)-4-(methylsulfinyl)-1H-pyrazol-3-yl)-5-(1-(trifluoromethyl)cyclobutyl)-1,3,4-thiadiazole

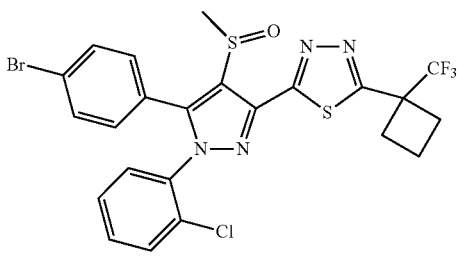

$^1$H NMR (400 MHz, CDCl$_3$) δ 7.46-7.33 (m, 6H), 7.25-7.18 (m, 2H), 3.22 (s, 3H), 2.87-2.83 (m, 4H), 2.23-2.14 (m, 2H).
MH+601.

Example 75

2-(5-(4-bromophenyl)-1-(2-chlorophenyl)-4-(methylsulfinyl)-1H-pyrazol-3-yl)-5-(1-(4-chlorophenyl)cyclopropyl)-1,3,4-thiadiazole

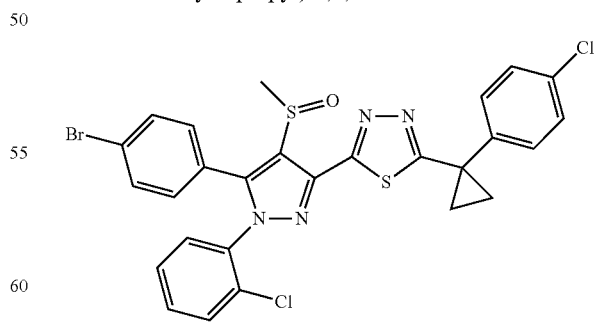

$^1$H NMR (400 MHz, CDCl$_3$) δ 7.44-7.32 (m, 8H), 7.30-7.29 (m, 2H), 7.21-7.18 (m, 2H), 3.17 (s, 3H), 1.99-1.96 (m, 2H), 1.55-1.52 (m, 2H).
MH+629.

Example 76

2-tert-butyl-5-(5-(4-chlorophenyl)-1-(2,4-dichlorophenyl)-4-(ethylsulfinyl)-1H-pyrazol-3-yl)-1,3,4-thiadiazole

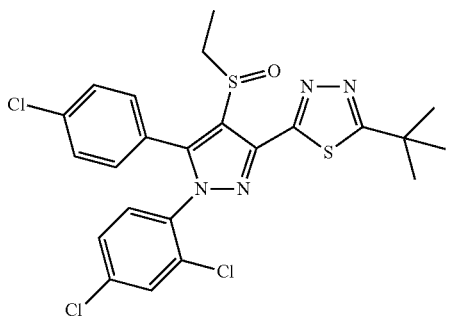

$^1$H NMR (400 MHz, CDCl$_3$) δ 7.46-7.45 (m, 1H), 7.32-7.27 (m, 6H), 3.46-3.40 (m, 2H), 1.54 (s, 9H), 1.34-1.31 (m, 3H).
MH+539.

Example 78

2-(5-(4-chlorophenyl)-1-(2,4-dichlorophenyl)-4-(ethylsulfinyl)-1H-pyrazol-3-yl)-5-(1-(trifluoromethyl)cyclobutyl)-1,3,4-thiadiazole

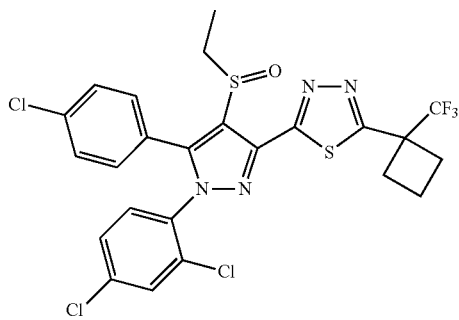

$^1$H NMR (400 MHz, CDCl$_3$) δ 7.47-7.45 (m, 1H), 7.33-7.30 (m, 5H), 7.26-7.24 (m, 1H), 3.49-3.40 (m, 2H), 2.85 (t, J=8 Hz, 4H), 2.22-2.16 (m, 2H), 1.33 (t, J=7.4 Hz, 3H).
MH+605.

Example 77

2-(5-(4-chlorophenyl)-1-(2,4-dichlorophenyl)-4-(ethylsulfinyl)-1H-pyrazol-3-yl)-5-(1-(trifluoromethyl)cyclopropyl)-1,3,4-thiadiazole

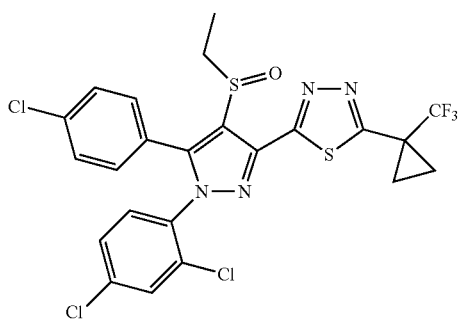

$^1$H NMR (400 MHz, CDCl$_3$) δ 7.47-7.46 (m, 1H), 7.33-7.27 (m, 6H), 3.46-3.38 (m, 2H), 1.77 (bs, 2H), 1.67-1.65 (m, 2H), 1.33-1.29 (m, 3H).
MH+591.

Example 79

2-(5-(4-chlorophenyl)-1-(2,4-dichlorophenyl)-4-(ethylsulfinyl)-1H-pyrazol-3-yl)-5-(1-(4-chlorophenyl)cyclopropyl)-1,3,4-thiadiazole

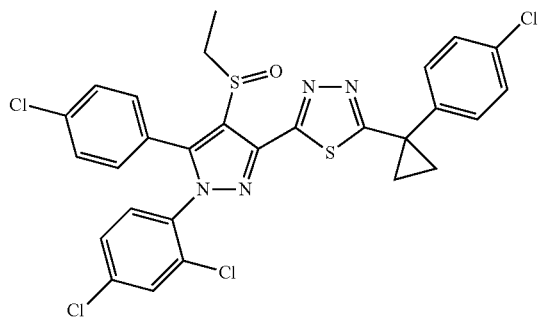

$^1$H NMR (400 MHz, CDCl$_3$) δ 7.44-7.42 (m, 3H), 7.35-7.33 (m, 2H), 7.29-7.20 (m, 6H), 3.43-3.37 (m, 2H), 1.99-1.96 (m, 2H), 1.55-1.52 (m, 2H), 1.28 (t, J=7.4 Hz, 3H).
MH+633.

Preparation of Sulfone Compound (Formula (Ic-1 and Ic-2))

Example 80

2-tert-butyl-5-(5-(4-chlorophenyl)-1-(2,4-dichlorophenyl)-4-(methylsulfonyl)-1H-pyrazol-3-yl)-1,3,4-oxadiazole (Ic-1)

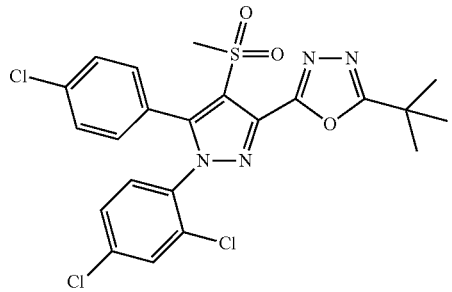

To a solution of 2-tert-Butyl-5-(5-(4-chlorophenyl)-1-(2,4-dichlorophenyl)-4-(methylthio)-1H-pyrazol-3-yl)-1,3,4-oxadiazole (Ia-1) (160 mg, 0.32 mmol) in $CH_2Cl_2$ (10 mL) was added m-CPBA (77% Max, 179 mg, 0.80 mmol). The reaction mixture was stirred for 1 hr at room temperature. Saturated $NaHCO_3$ was added to the reaction mixture, then the organic extract was dried over anhydrous $MgSO_4$, filtered, and concentrated in vacuo. The residue was subjected to silica gel column chromatography (eluent: hexane/EtOAc=2/1) to obtain 68 mg (41%) of the title compound as a white solid.

$^1$H NMR (400 MHz, $CDCl_3$) δ 7.45-7.44 (m, 1H), 7.34-7.32 (m, 4H), 7.25-7.23 (m, 2H), 3.53 (s, 3H), 1.51 (s, 9H).

MH+525.

The following compounds of Examples 81 to 99 were obtained by using corresponding starting materials and repeating the procedure of Example 80.

Example 81

2-(5-(4-chlorophenyl)-1-(2,4-dichlorophenyl)-4-(methylsulfonyl)-1H-pyrazol-3-yl)-5-(1-(trifluoromethyl)cyclopropyl)-1,3,4-oxadiazole

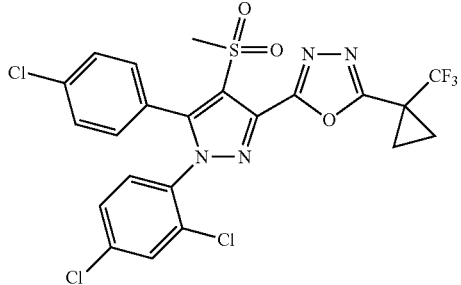

$^1$H NMR (400 MHz, $CDCl_3$) δ 7.46-7.45 (m, 1H), 7.33-7.30 (m, 3H), 7.27-7.23 (m, 3H), 3.62 (s, 3H), 1.80 (m, 2H), 1.68-1.65 (m, 2H).

MH+577.

Example 82

2-(5-(4-chlorophenyl)-1-(2,4-dichlorophenyl)-4-(methylsulfonyl)-1H-pyrazol-3-yl)-5-(1-(trifluoromethyl)cyclobutyl)-1,3,4-oxadiazole

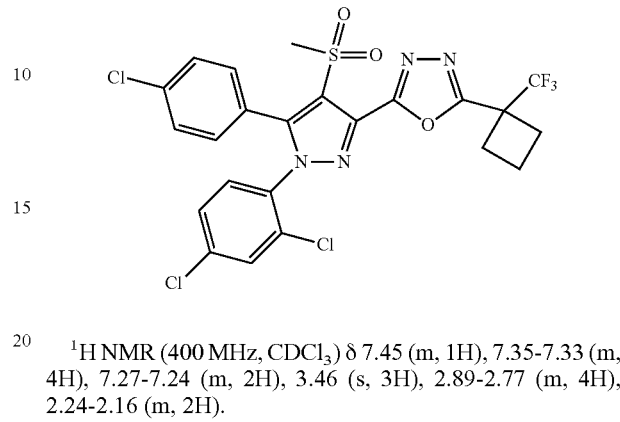

$^1$H NMR (400 MHz, $CDCl_3$) δ 7.45 (m, 1H), 7.35-7.33 (m, 4H), 7.27-7.24 (m, 2H), 3.46 (s, 3H), 2.89-2.77 (m, 4H), 2.24-2.16 (m, 2H).

MH+591.

Example 83

2-(5-(4-chlorophenyl)-1-(2,4-dichlorophenyl)-4-(methylsulfonyl)-1H-pyrazol-3-yl)-5-(1-(4-chlorophenyl)cyclopropyl)-1,3,4-oxadiazole

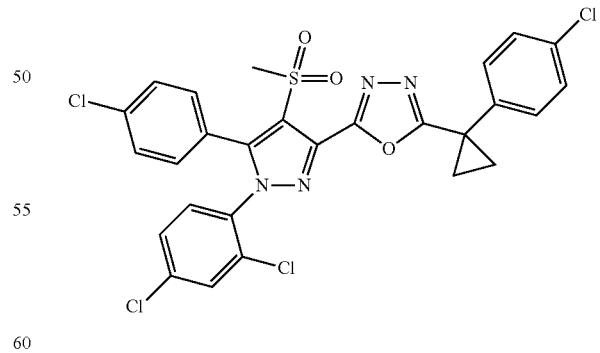

$^1$H NMR (400 MHz, $CDCl_3$) δ 7.44-7.42 (m, 3H), 7.36-7.29 (m, 5H), 7.27-7.26 (m, 1H), 7.23-7.20 (m, 2H), 3.38 (s, 3H), 1.85-1.82 (m, 2H), 1.52-1.49 (m, 2H).

MH+619.

Example 84

2-tert-butyl-5-(1-(2-chlorophenyl)-5-(4-chlorophenyl)-4-(methylsulfonyl)-1H-pyrazol-3-yl)-1,3,4-oxadiazole

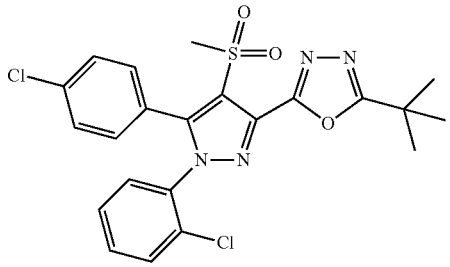

$^1$H NMR (400 MHz, CDCl$_3$) δ 7.44-7.33 (m, 4H), 7.32-7.26 (m, 3H), 7.25 (m, 1H), 3.52 (s, 3H), 1.51 (s, 9H). MH+491.

Example 85

2-(1-(2-chlorophenyl)-5-(4-chlorophenyl)-4-(methylsulfonyl)-1H-pyrazol-3-yl)-5-(1-(trifluoromethyl)cyclopropyl)-1,3,4-oxadiazole

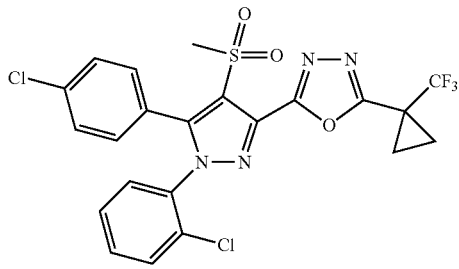

$^1$H NMR (400 MHz, CDCl$_3$) δ 7.44-7.33 (m, 4H), 7.31-7.21 (m, 4H), 3.47 (s, 3H), 1.69-1.67 (m, 2H). MH+543.

Example 86

2-(1-(2-chlorophenyl)-5-(4-chlorophenyl)-4-(methylsulfonyl)-1H-pyrazol-3-yl)-5-(1-(trifluoromethyl)cyclobutyl)-1,3,4-oxadiazole

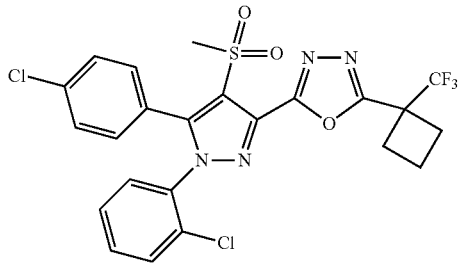

$^1$H NMR (400 MHz, CDCl$_3$) δ 7.45-7.38 (m, 3H), 7.36-7.31 (m, 1H), 7.29-7.25 (m, 4H), 3.46 (s, 3H), 2.89-2.77 (m, 4H), 2.23-2.15 (q, J=8 Hz, 2H). MH+557.

Example 87

2-(1-(2-chlorophenyl)-5-(4-chlorophenyl)-4-(methylsulfonyl)-1H-pyrazol-3-yl)-5-(1-(4-chlorophenyl)cyclopropyl)-1,3,4-oxadiazole

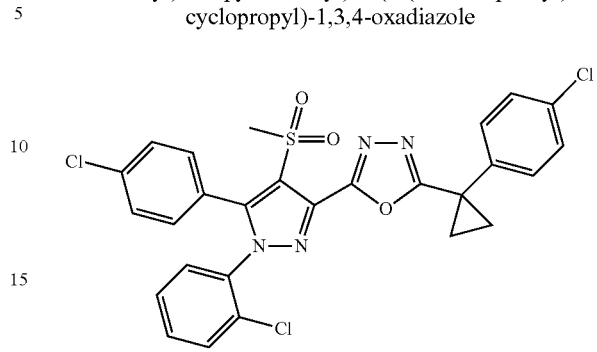

$^1$H NMR (400 MHz, CDCl$_3$) δ 7.44-7.39 (m, 4H), 7.38-7.30 (m, 4H), 7.29-7.22 (m, 4H), 3.39 (s, 3H), 1.84-1.81 (m, 2H), 1.51-1.48 (m, 2H). MH+585.

Example 88

2-(5-(4-bromophenyl)-1-(2,4-dichlorophenyl)-4-(methylsulfonyl)-1H-pyrazol-3-yl)-5-tert-butyl-1,3,4-oxadiazole

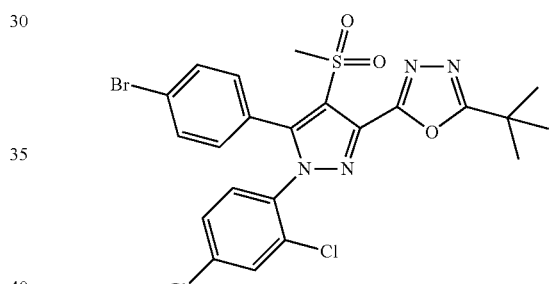

$^1$H NMR (400 MHz, CDCl$_3$) δ 7.49-7.45 (m, 3H), 7.34-7.29 (m, 2H), 7.19-7.17 (m, 2H), 3.51 (s, 3H), 1.51 (s, 9H). MH+569.

Example 89

2-(5-(4-bromophenyl)-1-(2,4-dichlorophenyl)-4-(methylsulfonyl)-1H-pyrazol-3-yl)-5-(1-(trifluoromethyl)cyclopropyl)-1,3,4-oxadiazole

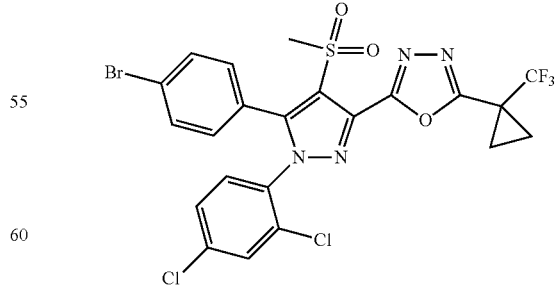

$^1$H NMR (400 MHz, CDCl$_3$) δ 7.50-7.45 (m, 3H), 7.35-7.32 (m, 2H), 7.19-7.17 (m, 2H), 3.46 (s, 3H), 1.72-7.64 (m, 4H). MH+621..

Example 90

2-(5-(4-bromophenyl)-1-(2,4-dichlorophenyl)-4-(methylsulfonyl)-1H-pyrazol-3-yl)-5-(1-(trifluoromethyl)cyclobutyl)-1,3,4-oxadiazole

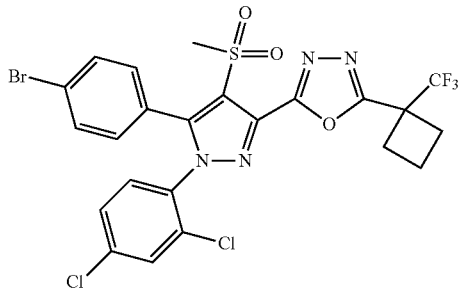

$^1$H NMR (400 MHz, CDCl$_3$) δ 7.50-7.48 (m, 2H), 7.45-7.44 (m, 1H), 7.35-7.32 (m, 2H), 7.20-7.17 (m, 2H), 3.46 (s, 3H), 2.89-2.77 (m, 4H), 2.24-2.16 (m, 2H).
MH+635.

Example 91

2-(5-(4-bromophenyl)-1-(2,4-dichlorophenyl)-4-(methylsulfonyl)-1H-pyrazol-3-yl)-5-(1-(4-chlorophenyl)cyclopropyl)-1,3,4-oxadiazole

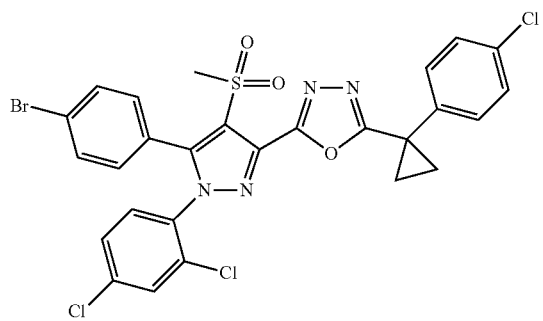

$^1$H NMR (400 MHz, CDCl$_3$) δ 7.48-7.41 (m, 5H), 7.36-7.29 (m, 4H), 7.16-7.14 (m, 2H), 3.37 (s, 3H), 1.84-1.81 (m, 2H), 1.51-1.49 (m, 2H).
MH+663.

Example 92

2-(5-(4-bromophenyl)-1-(2-chlorophenyl)-4-(methylsulfonyl)-1H-pyrazol-3-yl)-5-tert-butyl-1,3,4-oxadiazole

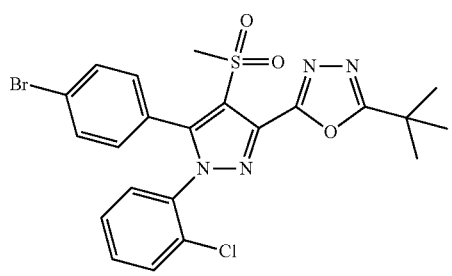

$^1$H NMR (400 MHz, CDCl$_3$) δ 7.46-7.31 (m, 6H), 7.21-7.18 (m, 2H), 3.52 (s, 3H), 1.51 (s, 9H).
MH+535.

Example 93

2-(5-(4-bromophenyl)-1-(2-chlorophenyl)-4-(methylsulfonyl)-1H-pyrazol-3-yl)-5-(1-(trifluoromethyl)cyclopropyl)-1,3,4-oxadiazole

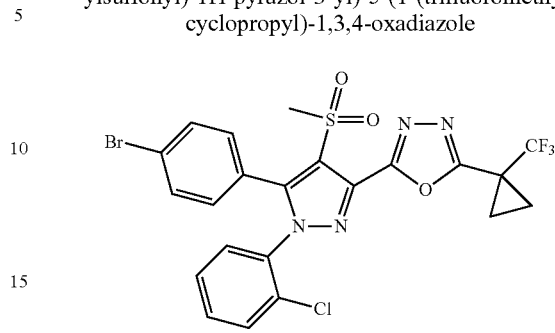

$^1$H NMR (400 MHz, CDCl$_3$) δ 7.47-7.41 (m, 4H), 7.38-7.34 (m, 2H), 7.20-7.18 (m, 2H), 3.47 (s, 3H), 1.69-1.66 (m, 4H).
MH+587.

Example 94

2-(5-(4-bromophenyl)-1-(2-chlorophenyl)-4-(methylsulfonyl)-1H-pyrazol-3-yl)-5-(1-(trifluoromethyl)cyclobutyl)-1,3,4-oxadiazole

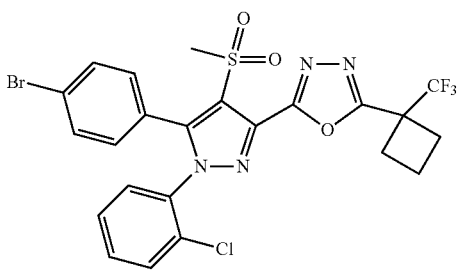

$^1$H NMR (400 MHz, CDCl$_3$) δ 7.47-7.32 (m, 6H), 7.21-7.18 (m, 2H), 3.46 (s, 3H), 2.89-2.77 (m, 4H), 2.24-2.15 (m, 2H).
MH+601.

Example 95

2-(5-(4-bromophenyl)-1-(2-chlorophenyl)-4-(methylsulfonyl)-1H-pyrazol-3-yl)-5-(1-(4-chlorophenyl)cyclopropyl)-1,3,4-oxadiazole

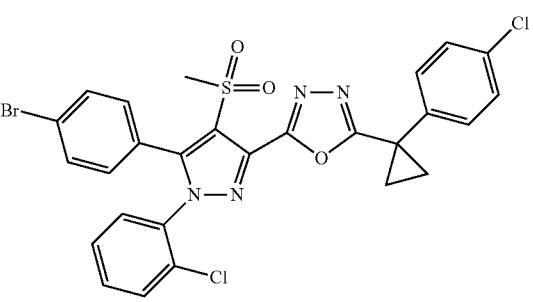

$^1$H NMR (400 MHz, CDCl$_3$) δ 7.45-7.37 (m, 6H), 7.35-7.32 (m, 4H), 7.17-7.15 (m, 2H), 3.39 (s, 3H), 1.84-1.82 (m, 2H), 1.51-1.48 (m, 2H)
MH+629. .

Example 96

2-tert-butyl-5-(5-(4-chlorophenyl)-1-(2,4-dichlorophenyl)-4-(ethylsulfonyl)-1H-pyrazol-3-yl)-1,3,4-oxadiazole

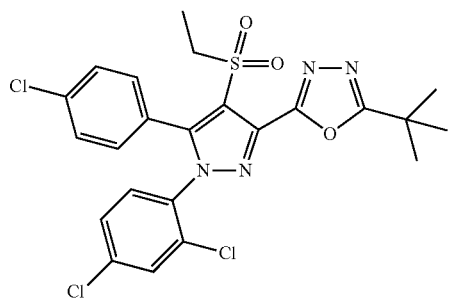

$^1$H NMR (400 MHz, CDCl$_3$) δ 7.45 (bs, 1H), 7.33-7.31 (m, 3H), 7.26-7.24 (m, 3H), 3.70-3.68 (m, 2H), 1.51 (s, 9H), 1.36-1.32 (m, 3H).
MH+539.

Example 97

2-(5-(4-chlorophenyl)-1-(2,4-dichlorophenyl)-4-(ethylsulfonyl)-1H-pyrazol-3-yl)-5-(1-(trifluoromethyl)cyclopropyl)-1,3,4-oxadiazole

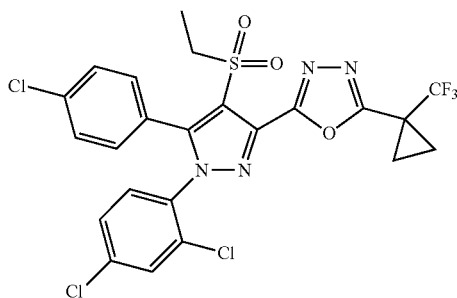

$^1$H NMR (400 MHz, CDCl$_3$) δ 7.46-7.45 (m, 1H), 7.33-7.28 (m, 3H), 7.26-7.24 (m, 3H), 3.63-3.58 (m, 2H), 1.72-1.64 (m, 4H), 1.35-1.31 (m, 3H).
MH+591.

Example 98

2-(5-(4-chlorophenyl)-1-(2,4-dichlorophenyl)-4-(ethylsulfonyl)-1H-pyrazol-3-yl)-5-(1-(trifluoromethyl)cyclobutyl)-1,3,4-oxadiazole

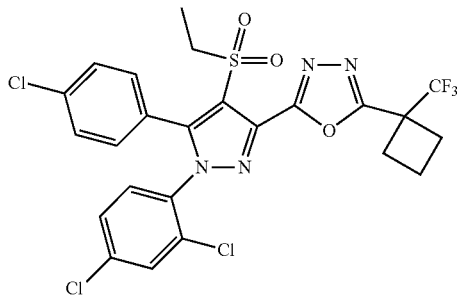

$^1$H NMR (400 MHz, CDCl$_3$) δ 7.46-7.45 (m, 1H), 7.34-7.31 (m, 4H), 7.28-7.25 (m, 2H), 3.62-3.57 (m, 2H), 2.89-2.77 (m, 4H), 2.20 (q, J=8 Hz, 2H), 1.33 (t, J=7.4 Hz, 3H).
MH+605.

Example 99

2-(5-(4-chlorophenyl)-1-(2,4-dichlorophenyl)-4-(ethylsulfonyl)-1H-pyrazol-3-yl)-5-(1-(4-chlorophenyl)cyclopropyl)-1,3,4-oxadiazole

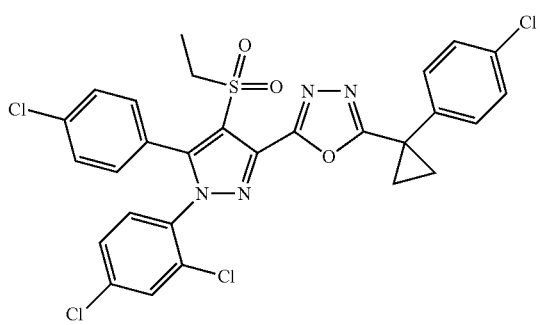

$^1$H NMR (400 MHz, CDCl$_3$) δ 7.44-7.41 (m, 3H), 7.35-7.24 (m, 6H), 7.23-7.22 (m, 2H), 3.53-3.52 (m, 2H), 1.84-1.81 (m, 2H), 1.51-1.48 (m, 2H), 1.26 (t, J=7.4 Hz, 3H).
MH+633.

Example 100

2-tert-butyl-5-(5-(4-chlorophenyl)-1-(2,4-dichlorophenyl)-4-(methylsulfonyl)-1H-pyrazol-3-yl)-1,3,4-thiadiazole (1c-2)

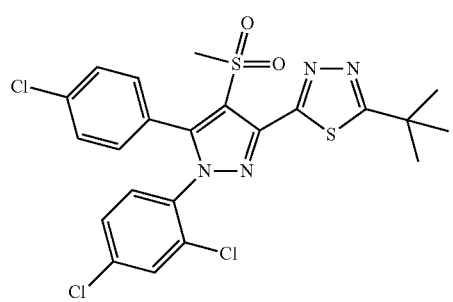

To a solution of 2-tert-Butyl-5-(5-(4-chlorophenyl)-1-(2,4-dichlorophenyl)-4-(methylthio)-1H-pyrazol-3-yl)-1,3,4-thiadiazole (Ia-2) (200 mg, 0.39 mmol) in CH$_2$Cl$_2$ (10 mL) was added m-CPBA (77% Max, 218 mg, 0.97 mmol). The reaction mixture was stirred for 1 hr at room temperature. Saturated NaHCO$_3$ was added to the reaction mixture, then the organic extract was dried over anhydrous MgSO$_4$, filtered, and concentrated in vacuo. The residue was subjected to silica gel column chromatography (eluent: hexane/EtOAc=2/1) to obtain 180 mg (85%) of the title compound as a white solid.

$^1$H NMR (400 MHz, CDCl$_3$) δ 7.46-7.45 (m, 1H), 7.33-7.30 (m, 3H), 7.28-7.24 (m, 3H), 3.68 (s, 3H), 1.56 (s, 9H).
MH+541.

The following compounds of Examples 101 to 119 were obtained by using corresponding starting materials and repeating the procedure of Example 100.

Example 101

2-(5-(4-chlorophenyl)-1-(2,4-dichlorophenyl)-4-(methylsulfonyl)-1H-pyrazol-3-yl)-5-(1-(trifluoromethyl)cyclopropyl)-1,3,4-thiadiazole

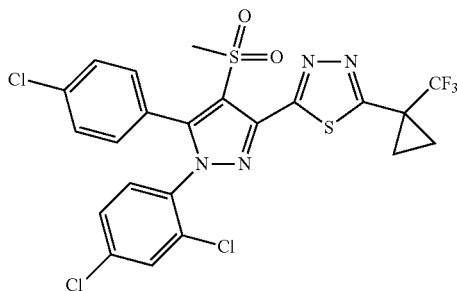

$^1$H NMR (400 MHz, CDCl$_3$) δ 7.46-7.45 (m, 1H), 7.34-7.30 (m, 4H), 7.26-7.24 (m, 2H), 3.46 (s, 3H), 1.72-1.65 (m, 4H).
MH+593.

Example 102

2-(5-(4-chlorophenyl)-1-(2,4-dichlorophenyl)-4-(methylsulfonyl)-1H-pyrazol-3-yl)-5-(1-(trifluoromethyl)cyclobutyl)-1,3,4-thiadiazole

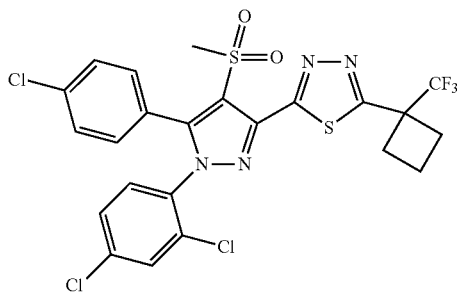

$^1$H NMR (400 MHz, CDCl$_3$) δ 7.46-7.45 (m, 1H), 7.33-7.30 (m, 3H), 7.27-7.24 (m, 3H), 3.66 (s, 3H), 2.88-2.83 (m, 4H), 2.24-2.18 (m, 2H).
MH+607.

Example 103

2-(5-(4-chlorophenyl)-1-(2,4-dichlorophenyl)-4-(methylsulfonyl)-1H-pyrazol-3-yl)-5-(1-(4-chlorophenyl)cyclopropyl)-1,3,4-thiadiazole

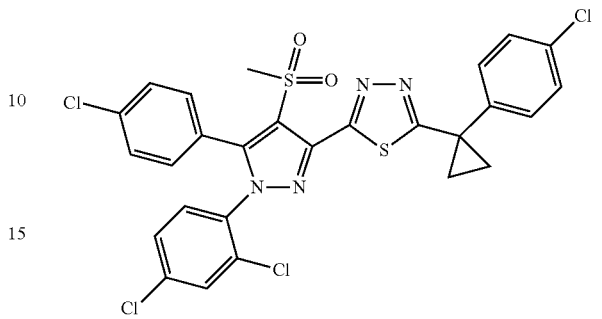

$^1$H NMR (400 MHz, CDCl$_3$) δ 7.44-7.41 (m, 3H), 7.36-7.34 (m, 2H), 7.31-7.26 (m, 3H), 7.22-7.19 (m, 3H), 3.63 (s, 3H), 2.01-1.98 (m, 2H), 1.57-1.54 (m, 2H).
MH+635.

Example 104

2-tert-butyl-5-(1-(2-chlorophenyl)-5-(4-chlorophenyl)-4-(methylsulfonyl)-1H-pyrazol-3-yl)-1,3,4-thiadiazole

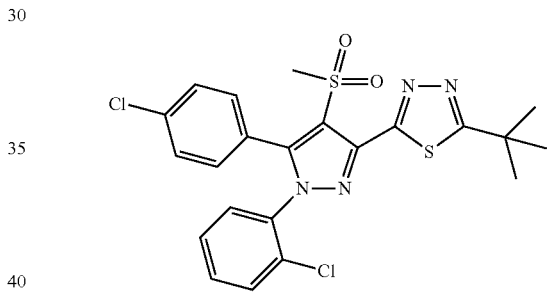

$^1$H NMR (400 MHz, CDCl$_3$) δ 7.44-7.37 (m, 2H), 7.32-7.31 (m, 2H), 7.30-7.24 (m, 4H), 3.68 (s, 3H), 1.55 (s, 9H).
MH+507.

Example 105

2-(1-(2-chlorophenyl)-5-(4-chlorophenyl)-4-(methylsulfonyl)-1H-pyrazol-3-yl)-5-(1-(trifluoromethyl)cyclopropyl)-1,3,4-thiadiazole

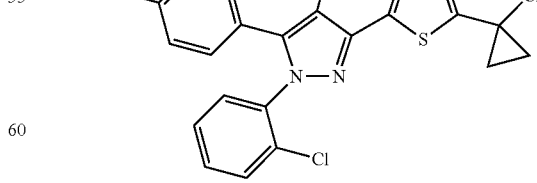

$^1$H NMR (400 MHz, CDCl$_3$) δ 7.45-7.37 (m, 2H), 7.33-7.32 (m, 2H), 7.30-7.24 (m, 4H), 3.63 (s, 3H), 1.81-1.80 (m, 2H), 1.68-1.65 (m, 2H).
MH+559.

Example 106

2-(1-(2-chlorophenyl)-5-(4-chlorophenyl)-4-(methyl-sulfonyl)-1H-pyrazol-3-yl)-5-(1-(trifluoromethyl)cyclobutyl)-1,3,4-thiadiazole

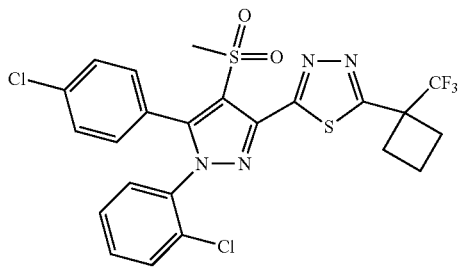

$^1$H NMR (400 MHz, CDCl$_3$) δ 7.45-7.35 (m, 2H), 7.33-7.30 (m, 2H), 7.28-7.25 (m, 4H), 3.67 (s, 3H), 2.91-2.80 (m, 4H), 2.24-2.15 (q, J=8 Hz, 2H).
MH+573.

Example 107

2-(1-(2-chlorophenyl)-5-(4-chlorophenyl)-4-(methyl-sulfonyl)-1H-pyrazol-3-yl)-5-(1-(4-chlorophenyl)cyclopropyl)-1,3,4-thiadiazole

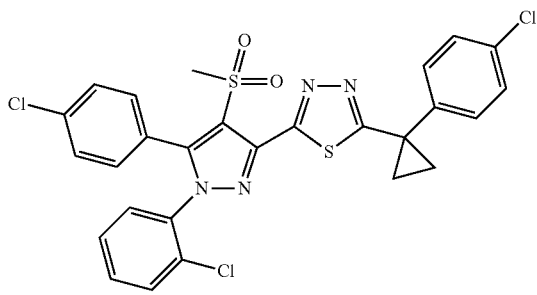

$^1$H NMR (400 MHz, CDCl$_3$) δ 7.44-7.41 (m, 2H), 7.39-7.33 (m, 3H), 7.30-7.22 (m, 7H), 3.64 (s, 3H), 2.00-1.96 (m, 2H), 1.57-1.54 (m, 2H).
MH+601.

Example 108

2-(5-(4-bromophenyl)-1-(2,4-dichlorophenyl)-4-(methylsulfonyl)-1H-pyrazol-3-yl)-5-tert-butyl-1,3,4-thiadiazole

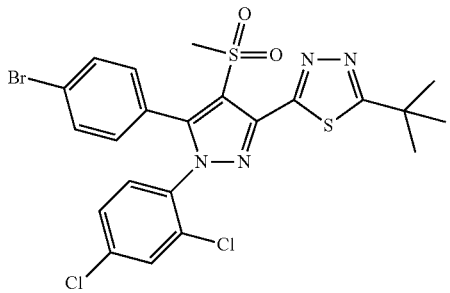

$^1$H NMR (400 MHz, CDCl$_3$) δ 7.48-7.45 (m, 3H), 7.32-7.24 (m, 2H), 7.19-7.16 (m, 2H), 3.67 (s, 3H), 1.55 (s, 9H).
MH+585.

Example 109

2-(5-(4-bromophenyl)-1-(2,4-dichlorophenyl)-4-(methylsulfonyl)-1H-pyrazol-3-yl)-5-(1-(trifluoromethyl)cyclopropyl)-1,3,4-thiadiazole

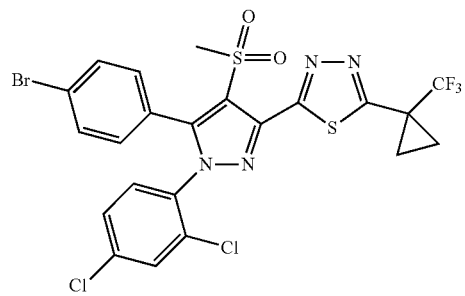

$^1$H NMR (400 MHz, CDCl$_3$) δ 7.49-7.46 (m, 3H), 7.33-7.25 (m, 2H), 7.18-7.16 (m, 2H), 3.62 (s, 3H), 1.82-1.80 (m, 2H), 1.69-1.65 (m, 2H).
MH+637.

Example 110

2-(5-(4-bromophenyl)-1-(2,4-dichlorophenyl)-4-(methylsulfonyl)-1H-pyrazol-3-yl)-5-(1-(trifluoromethyl)cyclobutyl)-1,3,4-thiadiazole

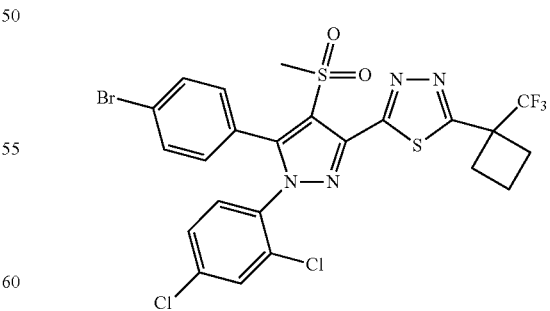

$^1$H NMR (400 MHz, CDCl$_3$) δ 7.47-7.44 (m, 3H), 7.31-7.23 (m, 2H), 7.17-7.15 (m, 2H), 3.64 (s, 3H), 2.86-2.78 (m, 4H), 2.22-2.14 (m, 2H).
MH+651.

Example 111

2-(5-(4-bromophenyl)-1-(2,4-dichlorophenyl)-4-(methylsulfonyl)-1H-pyrazol-3-yl)-5-(1-(4-chlorophenyl)cyclopropyl)-1,3,4-thiadiazole

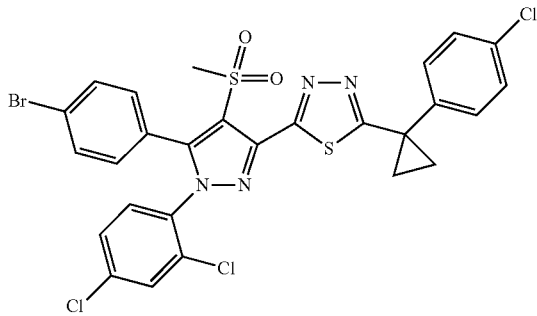

$^1$H NMR (400 MHz, CDCl$_3$) δ 7.47-7.42 (m, 5H), 7.37-7.34 (m, 2H), 7.29-7.26 (m, 1H), 7.22-7.19 (m, 1H), 7.16-7.14 (m, 2H), 3.63 (s, 3H), 2.02-1.99 (m, 2H). 1.60-1.55 (m, 2H).
MH+679.

Example 112

2-(5-(4-bromophenyl)-1-(2-chlorophenyl)-4-(methylsulfonyl)-1H-pyrazol-3-yl)-5-tert-butyl-1,3,4-thiadiazole

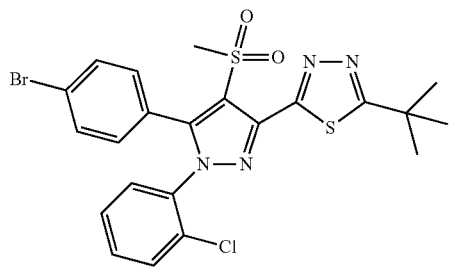

$^1$H NMR (400 MHz, CDCl$_3$) δ 7.45-7.37 (m, 4H), 7.33-7.31 (m, 2H), 7.20-7.17 (m, 2H), 3.68 (s, 3H), 1.55 (s, 9H).
MH+551.

Example 113

2-(5-(4-bromophenyl)-1-(2-chlorophenyl)-4-(methylsulfonyl)-1H-pyrazol-3-yl)-5-(1-(trifluoromethyl)cyclopropyl)-1,3,4-thiadiazole

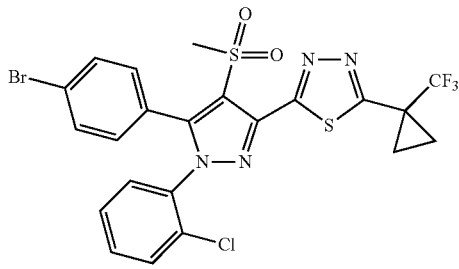

$^1$H NMR (400 MHz, CDCl$_3$) δ 7.45-7.38 (m, 4H), 7.33-7.32 (m, 2H), 7.20-7.18 (m, 2H), 3.63 (s, 3H), 1.80 (bs, 2H), 1.68-1.65 (m, 2H).
MH+603.

Example 114

2-(5-(4-bromophenyl)-1-(2-chlorophenyl)-4-(methylsulfonyl)-1H-pyrazol-3-yl)-5-(1-(trifluoromethyl)cyclobutyl)-1,3,4-thiadiazole

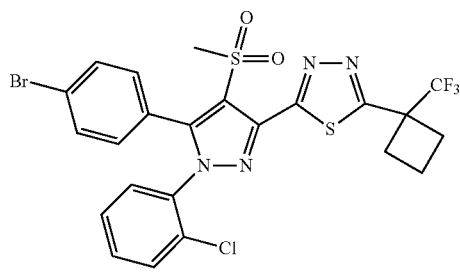

$^1$H NMR (400 MHz, CDCl$_3$) δ 7.46-7.37 (m, 4H), 7.35-7.32 (m, 2H), 7.21-7.18 (m, 2H), 3.67 (s, 3H), 2.91-2.80 (m, 4H), 2.24-2.15 (m, 2H).
MH+617.

Example 115

2-(5-(4-bromophenyl)-1-(2-chlorophenyl)-4-(methylsulfonyl)-1H-pyrazol-3-yl)-5-(1-(4-chlorophenyl)cyclopropyl)-1,3,4-thiadiazole

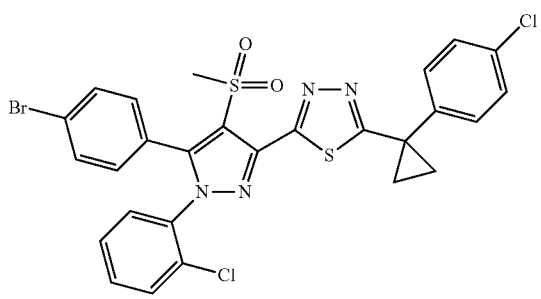

$^1$H NMR (400 MHz, CDCl$_3$) δ 7.45-7.41 (m, 3H), 7.39-7.32 (m, 4H), 7.30-7.27 (m, 3H), 7.18-7.15 (m, 2H), 3.64 (s, 3H), 2.01-1.98 (m, 2H), 1.56-1.53 (m, 2H).
MH+645.

Example 116

2-tert-butyl-5-(5-(4-chlorophenyl)-1-(2,4-dichlorophenyl)-4-(ethylsulfonyl)-1H-pyrazol-3-yl)-1,3,4-thiadiazole

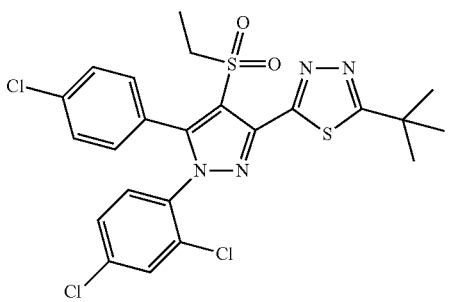

$^1$H NMR (400 MHz, CDCl$_3$) δ 7.45-7.44 (m, 1H), 7.31-7.28 (m, 3H), 7.25-7.23 (m, 3H), 3.92-3.89 (m, 2H), 1.55 (s, 9H), 1.38-1.34 (m, 3H).
MH+555.

Example 117

2-(5-(4-chlorophenyl)-1-(2,4-dichlorophenyl)-4-(ethylsulfonyl)-1H-pyrazol-3-yl)-5-(1-(trifluoromethyl)cyclopropyl)-1,3,4-thiadiazole

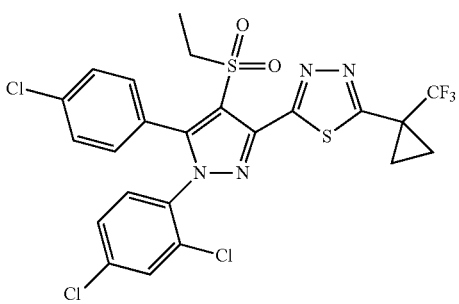

$^1$H NMR (400 MHz, CDCl$_3$) δ 7.46-7.45 (m, 1H), 7.32-7.29 (m, 3H), 7.27-7.24 (m, 3H), 3.87-3.82 (m, 2H), 1.81-1.79 (m, 2H), 1.68-1.56 (m, 2H), 1.37-1.34 (m, 3H).
MH+607.

Example 118

2-(5-(4-chlorophenyl)-1-(2,4-dichlorophenyl)-4-(ethylsulfonyl)-1H-pyrazol-3-yl)-5-(1-(trifluoromethyl)cyclobutyl)-1,3,4-thiadiazole

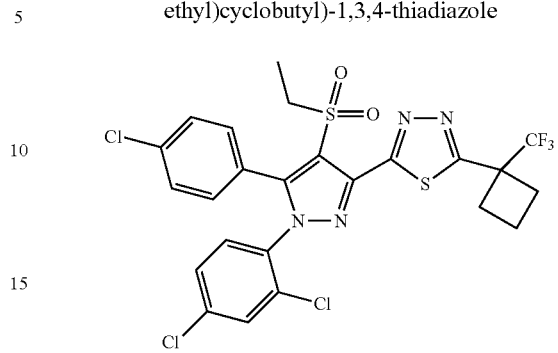

$^1$H NMR (400 MHz, CDCl$_3$) δ 7.46-7.45 (m, 1H), 7.32-7.29 (m, 3H), 7.26-7.24 (m, 3H), 3.93-3.87 (m, 2H), 2.91-2.80 (m, 4H), 2.20 (q, J=8 Hz, 2H), 1.38 (t, J=7.4 Hz, 3H).
MH+621.

Example 119

2-(5-(4-chlorophenyl)-1-(2,4-dichlorophenyl)-4-(ethylsulfonyl)-1H-pyrazol-3-yl)-5-(1-(4-chlorophenyl)cyclopropyl)-1,3,4-thiadiazole

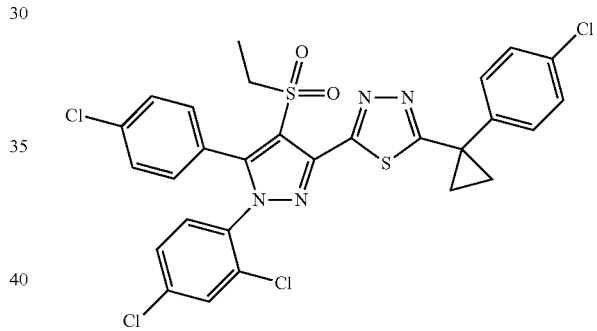

$^1$H NMR (400 MHz, CDCl$_3$) δ 7.44-7.41 (m, 3H), 7.35-7.33 (m, 2H), 7.29-7.18 (m, 6H), 3.88-3.86 (m, 2H), 2.00-1.97 (m, 2H), 1.55-1.53 (m, 2H), 1.32 (t, J=7.4 Hz, 3H).
MH+650.

Pharmacological Test: In Vitro Activity Analysis

The compounds of the present invention were analyzed for their binding characteristics for CB$_1$ and CB$_2$ and the pharmacological activity thereof in accordance with the method disclosed in [Devane W A, Dysarz F A 3$^{rd}$, Johnson M R, Melvin L S and Howlett A C, Determination and characterization of a cannabinoid receptor in rat brain, *Mol. Pharmacol.*, 34(5): 605-13(1998)]. The analysis was performed using [$^3$H]CP-55940 which is a selectively radioactivity-labeled 5-(1,1-dimethyheptyl)-2[5-hydroxy-2-(3-hydroxypropyl)-cyclohexyl]-phenol, purchased from PerkinElmer Life Sciences, Inc. (Boston, Mass., U.S.A.), through a rat CB-1 receptor binding protocol as follows.

The tissue obtained from the brain of SD rats was homogenized with a Dounce homogenate system in TME(50 mM Tris, 3 mM MgCl$_2$ and 1 mM EDTA, pH 7.4) at 4° C., and the homogenate was centrifuged at 48,000 g for 30 min. at 4° C. The pellet was resuspended in 5 ml of TME and the suspension was divided into aliquots and stored at −70° C. until its use in the following assay.

2 μl of the test compound was diluted in dimethylsulphoxide and was added to a deep well of a polypropylene plate, to which 50 μl of [$^3$H]CP-55940 diluted in a ligand buffer solution (0.1% bovine serum albumin(BAS)+TME) was added. The tissue concentrations were determined by Bradford protein analysis, and 148 μl of brain tissue of the required concentration was added to the plate. The plate was covered and placed in a 30° C. incubator for 60 min, and then transformed on GF/B filtermat pretreated in polyethylenimine (PEI) using a cell harvester. Each filter was washed five times and dried at 60° C. for 1 hr. Then, the degree of radioactivity retained by the filter was measured using Wallac Microbeta™ (PerkinElmer Life Sciences, Inc., Massachusetts, U.S.A.) and the activity of the compound for inhibiting $CB_1$ receptor was determined therefrom.

The compounds of the present invention were tested in the rat cannabinoid-1 receptor (CB1R) binding affinity assay, and the results are shown in Table 1 in comparison with that of rimonabant (SR141716). As can be seen from Table 1, the compounds of formula (I) according to the present invention exhibit binding affinities.

TABLE 1

| Example | $IC_{50}$ (nM) |
|---|---|
| 1 | 6.26 |
| 2 | 6.63 |
| 3 | 9.71 |
| 4 | 5.26 |
| 6 | 8.30 |
| 7 | 4.21 |
| 8 | 4.61 |
| 9 | 5.50 |
| 10 | 7.95 |
| 11 | 8.44 |
| 12 | 9.23 |
| 14 | 4.11 |
| 21 | 5.19 |
| 22 | 10.9 |
| 23 | 7.31 |
| 24 | 6.66 |
| 30 | 14.8 |
| 33 | 5.70 |
| 34 | 17.1 |
| 35 | 7.77 |
| 41 | 30.4 |
| 42 | 24.6 |
| 43 | 8.92 |
| 53 | 15.6 |
| 55 | 6.51 |
| 60 | 19.1 |
| 61 | 11.3 |
| 62 | 4.12 |
| 63 | 11.8 |
| 66 | 3.40 |
| 72 | 7.97 |
| 73 | 6.08 |
| 74 | 2.32 |
| 80 | 15.2 |
| 81 | 6.31 |
| 82 | 6.79 |
| 83 | 22.0 |
| 88 | 14.2 |
| 90 | 7.34 |
| 92 | 8.15 |
| 94 | 5.21 |
| 100 | 5.84 |
| 101 | 22.0 |
| 102 | 3.74 |
| 103 | 4.34 |
| 104 | 7.18 |
| 106 | 0.87 |
| 110 | 3.64 |
| 112 | 3.01 |
| 113 | 2.51 |

TABLE 1-continued

| Example | $IC_{50}$ (nM) |
|---|---|
| 114 | 1.08 |
| 115 | 1.40 |
| 119 | 2.06 |
| rimonabant | 5.0 ±0.5 |

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I) or a pharmaceutically acceptable salt thereof:

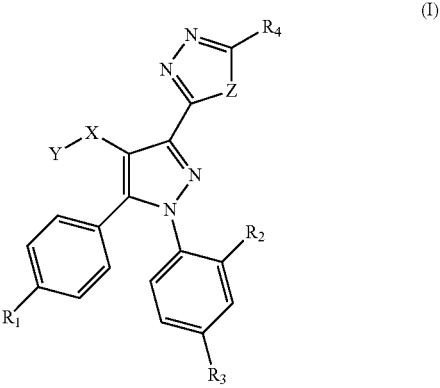

(I)

wherein:
$R_1$ is halogen, $C_{1-3}$ alkyl, $C_{1-3}$ alkoxy or trifluoromethyl;
$R_2$ is halogen, $C_{1-3}$ alkyl, $C_{1-3}$ alkoxy or trifluoromethyl;
$R_3$ is hydrogen or halogen;
$R_4$ is hydrogen, $NR_5R_6$, carbocycle, substituted carbocycle, aryl, substituted aryl, heteroaryl, substituted heteroaryl, heterocycle, substituted heterocycle, $C_{1-8}$ alkyl optionally substituted by alkoxy or halogen, $C_{2-6}$ alkenyl optionally substituted by alkoxy or halogen, $(CH_2)_m$—$C_{3-6}$ carbocycle optionally substituted by alkoxy or halogen, or $(CH_2)_m$—$R_7$, m being 1 or 2;
$R_5$ and $R_6$ are each independently hydrogen, $C_{1-6}$ alkyl, substituted $C_{1-6}$ alkyl, $C_{2-6}$ alkenyl, substituted $C_{2-6}$ alkenyl, $C_{3-7}$ cycloalkyl, substituted $C_{3-7}$ cycloalkyl, aryl, substituted aryl, heteroaryl, substituted heteroaryl, heterocycloalkyl, substituted heterocycloalkyl; or
$R_5$ and $R_6$, together with the nitrogen atom to which they are bonded, form a 4- to 10-membered saturated or unsaturated heterocyclic ring which is optionally substituted by one or more $C_{1-3}$ alkyl, benzyl, phenyl, $C_{1-3}$ alkoxy or halogen;
$R_7$ is phenyl, furanyl, benzofuranyl, thienyl, benzothienyl, pyridinyl, pyrimidinyl, pyrazinyl, pyridizinyl, tetrahydrofuranyl, tetrahydropyranyl, dioxanyl, 1,4-benzodioxanyl or benzo[1,3]dioxolyl, each being optionally substituted by one or more groups consisting of halogen, $C_{1-3}$ alkyl and $C_{1-2}$ alkoxy, each optionally having one to three fluorine substitutes;
X is a sulfur atom, a sulfoxide (S=O) or a sulfone ($SO_2$) moiety;
Y is methyl or ethyl; and
Z is O or S.

2. The compound of claim 1, which is a compound of formula (Ia), (Ib) or (Ic):

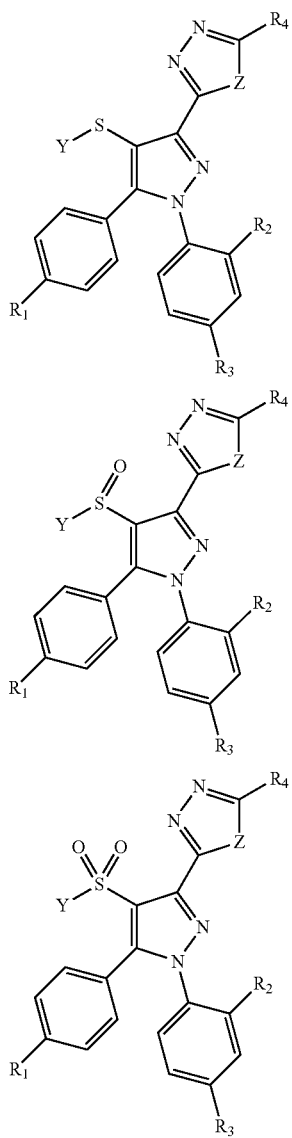

wherein, $R_1$, $R_2$, $R_3$, $R_4$, Y and Z have the same meanings as defined in claim 1.

3. A compound according to claim 1 selected from the group consisting of:
2-tert-butyl-5-(5-(4-chlorophenyl)-1-(2,4-dichlorophenyl)-4-(methylthio)-1H-pyrazol-3-yl)-1,3,4-oxadiazole;
2-(5-(4-chlorophenyl)-1-(2,4-dichlorophenyl)-4-(methylthio)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(methylthio)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(methylthio)-1H-pyrazol-3-yl)-5-(1-(4-chlorophenyl)cyclopropyl)-1,3,4-oxadiazole;
2-tert-butyl-5-(1-(2-chlorophenyl)-5-(4-chlorophenyl)-4-(methylthio)-1H-pyrazol-3-yl)-1,3,4-oxadiazole;
2-(1-(2-chlorophenyl)-5-(4-chlorophenyl)-4-(methylthio)-1H-pyrazol-3-yl)-5-(1-(trifluoromethyl)cyclopropyl)-1,3,4-oxadiazole;
2-(1-(2-chlorophenyl)-5-(4-chlorophenyl)-4-(methylthio)-1H-pyrazol-3-yl)-5-(1-(trifluoromethyl)cyclobutyl)-1,3,4-oxadiazole;
2-(1-(2-chlorophenyl)-5-(4-chlorophenyl)-4-(methylthio)-1H-pyrazol-3-yl)-5-(1-(4-chlorophenyl)cyclopropyl)-1,3,4-oxadiazole;
2-(5-(4-cromophenyl)-1-(2,4-dichlorophenyl)-4-(methylthio)-1H-pyrazol-3-yl)-5-tert-butyl-1,3,4-oxadiazole;
2-(5-(4-bromophenyl)-1-(2,4-dichlorophenyl)-4-(methylthio)-1H-pyrazol-3-yl)-5-(1-(trifluoromethyl)cyclopropyl)-1,3,4-oxadiazole;
2-(5-(4-bromophenyl)-1-(2,4-dichlorophenyl)-4-(methylthio)-1H-pyrazol-3-yl)-5-(1-(trifluoromethyl)cyclobutyl)-1,3,4-oxadiazole;
2-(5-(4-bromophenyl)-1-(2,4-dichlorophenyl)-4-(methylthio)-1H-pyrazol-3-yl)-5-(1-(4-chlorophenyl)cyclopropyl)-1,3,4-oxadiazole;
2-(5-(4-bromophenyl)-1-(2-chlorophenyl)-4-(methylthio)-1H-pyrazol-3-yl)-5-tert-butyl-1,3,4-oxadiazole;
2-(5-(4-bromophenyl)-1-(2-chlorophenyl)-4-(methylthio)-1H-pyrazol-3-yl)-5-(1-(trifluoromethyl)cyclopropyl)-1,3,4-oxadiazole;
2-(5-(4-bromophenyl)-1-(2-chlorophenyl)-4-(methylthio)-1H-pyrazol-3-yl)-5-(1-(trifluoromethyl)cyclobutyl)-1,3,4-oxadiazole;
2-(5-(4-bromophenyl)-1-(2-chlorophenyl)-4-(methylthio)-1H-pyrazol-3-yl)-5-(1-(4-chlorophenyl)cyclopropyl)-1,3,4-oxadiazole;
2-tert-butyl-5-(5-(4-chlorophenyl)-1-(2,4-dichlorophenyl)-4-(ethylthio)-1H-pyrazol-3-yl)-1,3,4-oxadiazole;
2-(5-(4-chlorophenyl)-1-(2,4-dichlorophenyl)-4-(ethylthio)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(ethylthio)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(ethylthio)-1H-pyrazol-3-yl)-5-(1-(4-chlorophenyl)cyclopropyl)-1,3,4-oxadiazole;
2-tert-butyl-5-(5-(4-chlorophenyl)-1-(2,4-dichlorophenyl)-4-(methylthio)-1H-pyrazol-3-yl)-1,3,4-thiadiazole;
2-(5-(4-chlorophenyl)-1-(2,4-dichlorophenyl)-4-(methylthio)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(methylthio)-1H-pyrazol-3-yl)-5-(1-(trifluoromethyl)cyclobutyl)-1,3,4-thiadiazole;
2-(5-(4-chlorophenyl)-1-(2,4-dichlorophenyl)-4-(methylthio)-1H-pyrazol-3-yl)-5-(1-(4-chlorophenyl)cyclopropyl)-1,3,4-thiadiazole;
2-tert-butyl-5-(1-(2-chlorophenyl)-5-(4-chlorophenyl)-4-(methylthio)-1H-pyrazol-3-yl)-1,3,4-thiadiazole;
2-(1-(2-chlorophenyl)-5-(4-chlorophenyl)-4-(methylthio)-1H-pyrazol-3-yl)-5-(1-(trifluoromethyl)cyclopropyl)-1,3,4-thiadiazole;
2-(1-(2-chlorophenyl)-5-(4-chlorophenyl)-4-(methylthio)-1H-pyrazol-3-yl)-5-(1-(trifluoromethyl)cyclobutyl)-1,3,4-thiadiazole;
2-(1-(2-chlorophenyl)-5-(4-chlorophenyl)-4-(methylthio)-1H-pyrazol-3-yl)-5-(1-(4-chlorophenyl)cyclopropyl)-1,3,4-thiadiazole;
2-(5-(4-bromophenyl)-1-(2,4-dichlorophenyl)-4-(methylthio)-1H-pyrazol-3-yl)-5-tert-butyl-1,3,4-thiadiazole;
2-(5-(4-bromophenyl)-1-(2,4-dichlorophenyl)-4-(methylthio)-1H-pyrazol-3-yl)-5-(1-(trifluoromethyl)cyclopropyl)-1,3,4-thiadiazole;
2-(5-(4-bromophenyl)-1-(2,4-dichlorophenyl)-4-(methylthio)-1H-pyrazol-3-yl)-5-(1-(trifluoromethyl)cyclobutyl)-1,3,4-thiadiazole;

2-(5-(4-bromophenyl)-1-(2,4-dichlorophenyl)-4-(methylthio)-1H-pyrazol-3-yl)-5-(1-(4-chlorophenyl)cyclopropyl)-1,3,4-thiadiazole;
2-(5-(4-bromophenyl)-1-(2-chlorophenyl)-4-(methylthio)-1H-pyrazol-3-yl)-5-tert-butyl-1,3,4-thiadiazole;
2-(5-(4-bromophenyl)-1-(2-chlorophenyl)-4-(methylthio)-1H-pyrazol-3-yl)-5-(1-(trifluoromethyl)cyclopropyl)-1,3,4-thiadiazole;
2-(5-(4-bromophenyl)-1-(2-chlorophenyl)-4-(methylthio)-1H-pyrazol-3-yl)-5-(1-(trifluoromethyl)cyclobutyl)-1,3,4-thiadiazole;
2-(5-(4-bromophenyl)-1-(2-chlorophenyl)-4-(methylthio)-1H-pyrazol-3-yl)-5-(1-(4-chlorophenyl)cyclopropyl)-1,3,4-thiadiazole;
2-tert-butyl-5-(5-(4-chlorophenyl)-1-(2,4-dichlorophenyl)-4-(ethylthio)-1H-pyrazol-3-yl)-1,3,4-thiadiazole;
2-(5-(4-chlorophenyl)-1-(2,4-dichlorophenyl)-4-(ethylthio)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(ethylthio)-1H-pyrazol-3-yl)-5-(1-(trifluoromethyl)cyclobutyl)-1,3,4-thiadiazole;
2-(5-(4-chlorophenyl)-1-(2,4-dichlorophenyl)-4-(ethylthio)-1H-pyrazol-3-yl)-5-(1-(4-chlorophenyl)cyclopropyl)-1,3,4-thiadiazole;
2-tert-butyl-5-(5-(4-chlorophenyl)-1-(2,4-dichlorophenyl)-4-(methylsulfinyl)-1H-pyrazol-3-yl)-1,3,4-oxadiazole;
2-(5-(4-chlorophenyl)-1-(2,4-dichlorophenyl)-4-(methylsulfinyl)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(methylsulfinyl)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(methylsulfinyl)-1H-pyrazol-3-yl)-5-(1-(4-chlorophenyl)cyclopropyl)-1,3,4-oxadiazole;
2-tert-butyl-5-(1-(2-chlorophenyl)-5-(4-chlorophenyl)-4-(methylsulfinyl)-1H-pyrazol-3-yl)-1,3,4-oxadiazole;
2-(1-(2-chlorophenyl)-5-(4-chlorophenyl)-4-(methylsulfinyl)-1H-pyrazol-3-yl)-5-(1-(trifluoromethyl)cyclopropyl)-1,3,4-oxadiazole;
2-(1-(2-chlorophenyl)-5-(4-chlorophenyl)-4-(methylsulfinyl)-1H-pyrazol-3-yl)-5-(1-(trifluoromethyl)cyclobutyl)-1,3,4-oxadiazole;
2-(1-(2-chlorophenyl)-5-(4-chlorophenyl)-4-(methylsulfinyl)-1H-pyrazol-3-yl)-5-(1-(4-chlorophenyl)cyclopropyl)-1,3,4-oxadiazole;
2-(5-(4-bromophenyl)-1-(2,4-dichlorophenyl)-4-(methylsulfinyl)-1H-pyrazol-3-yl)-5-tert-butyl-1,3,4-oxadiazole;
2-(5-(4-bromophenyl)-1-(2,4-dichlorophenyl)-4-(methylsulfinyl)-1H-pyrazol-3-yl)-5-(1-(trifluoromethyl)cyclopropyl)-1,3,4-oxadiazole;
2-(5-(4-bromophenyl)-1-(2,4-dichlorophenyl)-4-(methylsulfinyl)-1H-pyrazol-3-yl)-5-(1-(trifluoromethyl)cyclobutyl)-1,3,4-oxadiazole;
2-(5-(4-bromophenyl)-1-(2,4-dichlorophenyl)-4-(methylsulfinyl)-1H-pyrazol-3-yl)-5-(1-(4-chlorophenyl)cyclopropyl)-1,3,4-oxadiazole;
2-(5-(4-bromophenyl)-1-(2-chlorophenyl)-4-(methylsulfinyl)-1H-pyrazol-3-yl)-5-tert-butyl-1,3,4-oxadiazole;
2-(5-(4-bromophenyl)-1-(2-chlorophenyl)-4-(methylsulfinyl)-1H-pyrazol-3-yl)-5-(1-(trifluoromethyl)cyclopropyl)-1,3,4-oxadiazole;
2-(5-(4-bromophenyl)-1-(2-chlorophenyl)-4-(methylsulfinyl)-1H-pyrazol-3-yl)-5-(1-(trifluoromethyl)cyclobutyl)-1,3,4-oxadiazole;
2-tert-butyl-5-(5-(4-chlorophenyl)-1-(2,4-dichlorophenyl)-4-(ethylsulfinyl)-1H-pyrazol-3-yl)-1,3,4-oxadiazole;
2-(5-(4-chlorophenyl)-1-(2,4-dichlorophenyl)-4-(ethylsulfinyl)-1H-pyrazol-3-yl)-5-(1-(trifluoromethyl)cyclopropyl)-1,3,4-oxadiazole;
2-(5-(4-chlorophenyl)-1-(2,4-dichlorophenyl)-4-(ethylsulfinyl)-1H-pyrazol-3-yl)-5-(1-(trifluoromethyl)cyclobutyl)-1,3,4-oxadiazole;
2-(5-(4-chlorophenyl)-1-(2,4-dichlorophenyl)-4-(ethylsulfinyl)-1H-pyrazol-3-yl)-5-(1-(4-chlorophenyl)cyclopropyl)-1,3,4-oxadiazole;
2-tert-butyl-5-(5-(4-chlorophenyl)-1-(2,4-dichlorophenyl)-4-(methylsulfinyl)-1H-pyrazol-3-yl)-1,3,4-thiadiazole;
2-(5-(4-chlorophenyl)-1-(2,4-dichlorophenyl)-4-(methylsulfinyl)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(methylsulfinyl)-1H-pyrazol-3-yl)-5-(1-(trifluoromethyl)cyclobutyl)-1,3,4-thiadiazole;
2-(5-(4-chlorophenyl)-1-(2,4-dichlorophenyl)-4-(methylsulfinyl)-1H-pyrazol-3-yl)-5-(1-(4-chlorophenyl)cyclopropyl)-1,3,4-thiadiazole;
2-tert-butyl-5-(1-(2-chlorophenyl)-5-(4-chlorophenyl)-4-(methylsulfinyl)-1H-pyrazol-3-yl)-1,3,4-thiadiazole;
2-(1-(2-chlorophenyl)-5-(4-chlorophenyl)-4-(methylsulfinyl)-1H-pyrazol-3-yl)-5-(1-(trifluoromethyl)cyclopropyl)-1,3,4-thiadiazole;
2-(1-(2-chlorophenyl)-5-(4-chlorophenyl)-4-(methylsulfinyl)-1H-pyrazol-3-yl)-5-(1-(trifluoromethyl)cyclobutyl)-1,3,4-thiadiazole;
2-(1-(2-chlorophenyl)-5-(4-chlorophenyl)-4-(methylsulfinyl)-1H-pyrazol-3-yl)-5-(1-(4-chlorophenyl)cyclopropyl)-1,3,4-thiadiazole;
2-(5-(4-bromophenyl)-1-(2,4-dichlorophenyl)-4-(methylsulfinyl)-1H-pyrazol-3-yl)-5-tert-butyl-1,3,4-thiadiazole;
2-(5-(4-bromophenyl)-1-(2,4-dichlorophenyl)-4-(methylsulfinyl)-1H-pyrazol-3-yl)-5-(1-(trifluoromethyl)cyclopropyl)-1,3,4-thiadiazole;
2-(5-(4-bromophenyl)-1-(2,4-dichlorophenyl)-4-(methylsulfinyl)-1H-pyrazol-3-yl)-5-(1-(trifluoromethyl)cyclobutyl)-1,3,4-thiadiazole;
2-(5-(4-bromophenyl)-1-(2,4-dichlorophenyl)-4-(methylsulfinyl)-1H-pyrazol-3-yl)-5-(1-(4-chlorophenyl)cyclopropyl)-1,3,4-thiadiazole;
2-(5-(4-bromophenyl)-1-(2-chlorophenyl)-4-(methylsulfinyl)-1H-pyrazol-3-yl)-5-tert-butyl-1,3,4-thiadiazole;
2-(5-(4-bromophenyl)-1-(2-chlorophenyl)-4-(methylsulfinyl)-1H-pyrazol-3-yl)-5-(1-(trifluoromethyl)cyclopropyl)-1,3,4-thiadiazole;
2-(5-(4-bromophenyl)-1-(2-chlorophenyl)-4-(methylsulfinyl)-1H-pyrazol-3-yl)-5-(1-(trifluoromethyl)cyclobutyl)-1,3,4-thiadiazole;
2-(5-(4-bromophenyl)-1-(2-chlorophenyl)-4-(methylsulfinyl)-1H-pyrazol-3-yl)-5-(1-(4-chlorophenyl)cyclopropyl)-1,3,4-thiadiazole;
2-tert-butyl-5-(5-(4-chlorophenyl)-1-(2,4-dichlorophenyl)-4-(ethylsulfinyl)-1H-pyrazol-3-yl)-1,3,4-thiadiazole;
2-(5-(4-chlorophenyl)-1-(2,4-dichlorophenyl)-4-(ethylsulfinyl)-1H-pyrazol-3-yl)-5-(1-(trifluoromethyl)cyclopropyl)-1,3,4-thiadiazole;
2-(5-(4-chlorophenyl)-1-(2,4-dichlorophenyl)-4-(ethylsulfinyl)-1H-pyrazol-3-yl)-5-(1-(trifluoromethyl)cyclobutyl)-1,3,4-thiadiazole;

2-(5-(4-chlorophenyl)-1-(2,4-dichlorophenyl)-4-(ethylsulfinyl)-1H-pyrazol-3-yl)-5-(1-(4-chlorophenyl)cyclopropyl)-1,3,4-thiadiazole;

2-tert-butyl-5-(5-(4-chlorophenyl)-1-(2,4-dichlorophenyl)-4-(methylsulfonyl)-1H-pyrazol-3-yl)-1,3,4-oxadiazole;

2-(5-(4-chlorophenyl)-1-(2,4-dichlorophenyl)-4-(methylsulfonyl)-1H-pyrazol-3-yl)-5-(1-(trifluoromethyl)cyclopropyl)-1,3,4-oxadiazole;

2-(5-(4-chlorophenyl)-1-(2,4-dichlorophenyl)-4-(methylsulfonyl)-1H-pyrazol-3-yl)-5-(1-(trifluoromethyl)cyclobutyl)-1,3,4-oxadiazole;

2-(5-(4-chlorophenyl)-1-(2,4-dichlorophenyl)-4-(methylsulfonyl)-1H-pyrazol-3-yl)-5-(1-(4-chlorophenyl)cyclopropyl)-1,3,4-oxadiazole;

2-tert-butyl-5-(1-(2-chlorophenyl)-5-(4-chlorophenyl)-4-(methylsulfonyl)-1H-pyrazol-3-yl)-1,3,4-oxadiazole;

2-(1-(2-chlorophenyl)-5-(4-chlorophenyl)-4-(methylsulfonyl)-1H-pyrazol-3-yl)-5-(1-(trifluoromethyl)cyclopropyl)-1,3,4-oxadiazole;

2-(1-(2-chlorophenyl)-5-(4-chlorophenyl)-4-(methylsulfonyl)-1H-pyrazol-3-yl)-5-(1-(trifluoromethyl)cyclobutyl)-1,3,4-oxadiazole;

2-(1-(2-chlorophenyl)-5-(4-chlorophenyl)-4-(methylsulfonyl)-1H-pyrazol-3-yl)-5-(1-(4-chlorophenyl)cyclopropyl)-1,3,4-oxadiazole;

2-(5-(4-bromophenyl)-1-(2,4-dichlorophenyl)-4-(methylsulfonyl)-1H-pyrazol-3-yl)-5-tert-butyl-1,3,4-oxadiazole;

2-(5-(4-bromophenyl)-1-(2,4-dichlorophenyl)-4-(methylsulfonyl)-1H-pyrazol-3-yl)-5-(1-(trifluoromethyl)cyclopropyl)-1,3,4-oxadiazole;

2-(5-(4-bromophenyl)-1-(2,4-dichlorophenyl)-4-(methylsulfonyl)-1H-pyrazol-3-yl)-5-(1-(trifluoromethyl)cyclobutyl)-1,3,4-oxadiazole;

2-(5-(4-bromophenyl)-1-(2,4-dichlorophenyl)-4-(methylsulfonyl)-1H-pyrazol-3-yl)-5-(1-(4-chlorophenyl)cyclopropyl)-1,3,4-oxadiazole;

2-(5-(4-bromophenyl)-1-(2-chlorophenyl)-4-(methylsulfonyl)-1H-pyrazol-3-yl)-5-tert-butyl-1,3,4-oxadiazole;

2-(5-(4-bromophenyl)-1-(2-chlorophenyl)-4-(methylsulfonyl)-1H-pyrazol-3-yl)-5-(1-(trifluoromethyl)cyclopropyl)-1,3,4-oxadiazole;

2-(5-(4-bromophenyl)-1-(2-chlorophenyl)-4-(methylsulfonyl)-1H-pyrazol-3-yl)-5-(1-(trifluoromethyl)cyclobutyl)-1,3,4-oxadiazole;

2-(5-(4-bromophenyl)-1-(2-chlorophenyl)-4-(methylsulfonyl)-1H-pyrazol-3-yl)-5-(1-(4-chlorophenyl)cyclopropyl)-1,3,4-oxadiazole;

2-tert-butyl-5-(5-(4-chlorophenyl)-1-(2,4-dichlorophenyl)-4-(ethylsulfonyl)-1H-pyrazol-3-yl)-1,3,4-oxadiazole;

2-(5-(4-chlorophenyl)-1-(2,4-dichlorophenyl)-4-(ethylsulfonyl)-1H-pyrazol-3-yl)-5-(1-(trifluoromethyl)cyclopropyl)-1,3,4-oxadiazole;

2-(5-(4-chlorophenyl)-1-(2,4-dichlorophenyl)-4-(ethylsulfonyl)-1H-pyrazol-3-yl)-5-(1-(trifluoromethyl)cyclobutyl)-1,3,4-oxadiazole;

2-(5-(4-chlorophenyl)-1-(2,4-dichlorophenyl)-4-(ethylsulfonyl)-1H-pyrazol-3-yl)-5-(1-(4-chlorophenyl)cyclopropyl)-1,3,4-oxadiazole;

2-tert-butyl-5-(5-(4-chlorophenyl)-1-(2,4-dichlorophenyl)-4-(methylsulfonyl)-1H-pyrazol-3-yl)-1,3,4-thiadiazole;

2-(5-(4-chlorophenyl)-1-(2,4-dichlorophenyl)-4-(methylsulfonyl)-1H-pyrazol-3-yl)-5-(1-(trifluoromethyl)cyclopropyl)-1,3,4-thiadiazole;

2-(5-(4-chlorophenyl)-1-(2,4-dichlorophenyl)-4-(methylsulfonyl)-1H-pyrazol-3-yl)-5-(1-(trifluoromethyl)cyclobutyl)-1,3,4-thiadiazole;

2-(5-(4-chlorophenyl)-1-(2,4-dichlorophenyl)-4-(methylsulfonyl)-1H-pyrazol-3-yl)-5-(1-(4-chlorophenyl)cyclopropyl)-1,3,4-thiadiazole;

2-tert-butyl-5-(1-(2-chlorophenyl)-5-(4-chlorophenyl)-4-(methylsulfonyl)-1H-pyrazol-3-yl)-1,3,4-thiadiazole;

2-(1-(2-chlorophenyl)-5-(4-chlorophenyl)-4-(methylsulfonyl)-1H-pyrazol-3-yl)-5-(1-(trifluoromethyl)cyclopropyl)-1,3,4-thiadiazole;

2-(1-(2-chlorophenyl)-5-(4-chlorophenyl)-4-(methylsulfonyl)-1H-pyrazol-3-yl)-5-(1-(trifluoromethyl)cyclobutyl)-1,3,4-thiadiazole;

2-(1-(2-chlorophenyl)-5-(4-chlorophenyl)-4-(methylsulfonyl)-1H-pyrazol-3-yl)-5-(1-(4-chlorophenyl)cyclopropyl)-1,3,4-thiadiazole;

2-(5-(4-bromophenyl)-1-(2,4-dichlorophenyl)-4-(methylsulfonyl)-1H-pyrazol-3-yl)-5-tert-butyl-1,3,4-thiadiazole;

2-(5-(4-bromophenyl)-1-(2,4-dichlorophenyl)-4-(methylsulfonyl)-1H-pyrazol-3-yl)-5-(1-(trifluoromethyl)cyclopropyl)-1,3,4-thiadiazole;

2-(5-(4-bromophenyl)-1-(2,4-dichlorophenyl)-4-(methylsulfonyl)-1H-pyrazol-3-yl)-5-(1-(trifluoromethyl)cyclobutyl)-1,3,4-thiadiazole;

2-(5-(4-bromophenyl)-1-(2,4-dichlorophenyl)-4-(methylsulfonyl)-1H-pyrazol-3-yl)-5-(1-(4-chlorophenyl)cyclopropyl)-1,3,4-thiadiazole;

2-(5-(4-bromophenyl)-1-(2-chlorophenyl)-4-(methylsulfonyl)-1H-pyrazol-3-yl)-5-tert-butyl-1,3,4-thiadiazole;

2-(5-(4-bromophenyl)-1-(2-chlorophenyl)-4-(methylsulfonyl)-1H-pyrazol-3-yl)-5-(1-(trifluoromethyl)cyclopropyl)-1,3,4-thiadiazole;

2-(5-(4-bromophenyl)-1-(2-chlorophenyl)-4-(methylsulfonyl)-1H-pyrazol-3-yl)-5-(1-(trifluoromethyl)cyclobutyl)-1,3,4-thiadiazole;

2-(5-(4-bromophenyl)-1-(2-chlorophenyl)-4-(methylsulfonyl)-1H-pyrazol-3-yl)-5-(1-(4-chlorophenyl)cyclopropyl)-1,3,4-thiadiazole;

2-tert-butyl-5-(5-(4-chlorophenyl)-1-(2,4-dichlorophenyl)-4-(ethylsulfonyl)-1H-pyrazol-3-yl)-1,3,4-thiadiazole;

2-(5-(4-chlorophenyl)-1-(2,4-dichlorophenyl)-4-(ethylsulfonyl)-1H-pyrazol-3-yl)-5-(1-(trifluoromethyl)cyclopropyl)-1,3,4-thiadiazole;

2-(5-(4-chlorophenyl)-1-(2,4-dichlorophenyl)-4-(ethylsulfonyl)-1H-pyrazol-3-yl)-5-(1-(trifluoromethyl)cyclobutyl)-1,3,4-thiadiazole; and 2-(5-(4-chlorophenyl)-1-(2,4-dichlorophenyl)-4-(ethylsulfonyl)-1H-pyrazol-3-yl)-5-(1-(4-chlorophenyl)cyclopropyl)-1,3,4-thiadiazole.

4. A method for preparing the compound of formula (Ia), which comprises (i) reacting a compound of formula (7) with a compound of formula (8) in the presence of a coupling reagent in a solvent to obtain a compound of formula (9); and (ii) cyclizing the compound of formula (9) using a dehydrat ing agent or sulfurating agent to obtain the compound of formula (Ia):

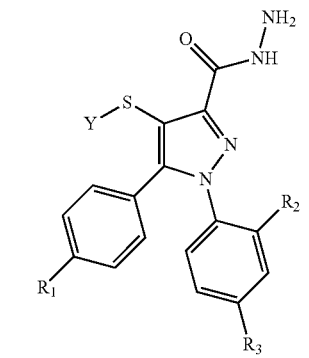
(7)

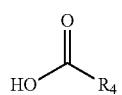
(8)

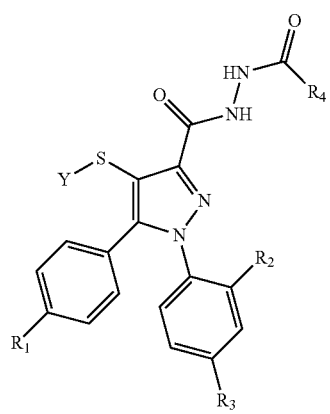
(9)

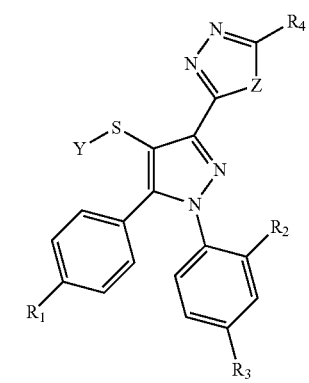
(Ia)

wherein, $R_1$, $R_2$, $R_3$, $R_4$, Y and Z have the same meanings as defined in claim 1.

5. A method for preparing the compound of formula (Ib), which comprises oxidizing the compound of formula (Ia) with 1 to 1.5 equivalents of meta-chloroperbenzoic acid (m-CPBA) in a solvent to obtain the compound of formula (Ib):

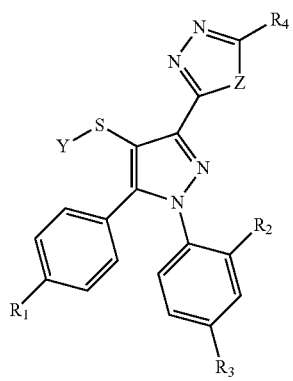
(Ia)

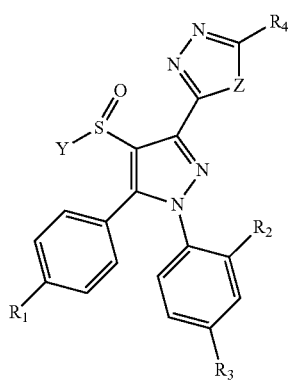
(Ib)

wherein, $R_1$, $R_2$, $R_3$, $R_4$, Y and Z have the same meanings as defined in claim 1.

6. A method for preparing the compound of formula (Ic), which comprises reacting the compound of formula (Ia) with 2 or more equivalents of meta-chloroperbenzoic acid (m-CPBA) in a solvent to obtain the compound of formula (Ic):

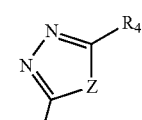
(Ia)

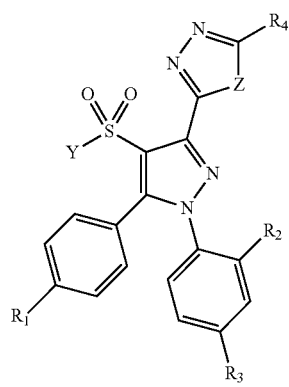
(Ic)

wherein, $R_1$, $R_2$, $R_3$, $R_4$, Y and Z have the same meanings as defined in claim 1.

7. A pharmaceutical composition comprising the compound of formula (I) of claim 1 as an active ingredient and a pharmaceutically acceptable carrier.

* * * * *